US010604743B2

(12) United States Patent
Boer et al.

(10) Patent No.: US 10,604,743 B2
(45) Date of Patent: Mar. 31, 2020

(54) UDP-GLYCOSYLTRANSFERASES

(71) Applicant: DSM IP ASSETS B.V., Heerlen (NL)

(72) Inventors: Viktor Marius Boer, Echt (NL); Johannes Gustaaf Ernst Van Leeuwen, Echt (NL); Priscilla Zwartjens, Echt (NL); Catharina Petronella Antonia Maria Kolen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/558,133

(22) PCT Filed: Mar. 16, 2016

(86) PCT No.: PCT/EP2016/055734
§ 371 (c)(1),
(2) Date: Sep. 13, 2017

(87) PCT Pub. No.: WO2016/146711
PCT Pub. Date: Sep. 22, 2016

(65) Prior Publication Data

US 2018/0044645 A1 Feb. 15, 2018

Related U.S. Application Data

(60) Provisional application No. 62/133,606, filed on Mar. 16, 2015.

(51) Int. Cl.
*C12N 1/14* (2006.01)
*C12N 1/16* (2006.01)
(Continued)

(52) U.S. Cl.
CPC .............. *C12N 9/1048* (2013.01); *A23L 2/60* (2013.01); *A23L 27/36* (2016.08); *C12N 1/14* (2013.01);
(Continued)

(58) Field of Classification Search
None
See application file for complete search history.

(56) References Cited

U.S. PATENT DOCUMENTS

| | | | |
|---|---|---|---|
| 9,738,890 | B2 | 8/2017 | Roubos et al. |
| 2013/0076280 | A1 | 3/2013 | Yoo |

(Continued)

FOREIGN PATENT DOCUMENTS

| | | | |
|---|---|---|---|
| EP | 1499708 | B1 | 1/2006 |
| WO | 03/062430 | A1 | 7/2003 |

(Continued)

OTHER PUBLICATIONS

Database Geneseq [Online] (Mar. 12, 2015), "S. Rebaudiana Derived Polypeptide (UGT2 4) SEQ:106.", XP-002760405, retrieved from EBI accession No. GSP:BBU04074, Database accession No. BBU04074 L: Sequence information for W02015007748; sequence.

(Continued)

*Primary Examiner* — Richard C Ekstrom
(74) *Attorney, Agent, or Firm* — McBee Moore Vanik IP, LLC

(57) ABSTRACT

The present invention relates to a recombinant host comprising a recombinant nucleic acid sequence encoding a polypeptide having at least about: a. 85% identity to the amino acid sequence set forth in SEQ ID NO: 1; b. 85% identity to the amino acid sequence set forth in SEQ ID NO: 3; c. 85% identity to the amino acid sequence set forth in SEQ ID NO: 6; d. 85% identity to the amino acid sequence set forth in SEQ ID NO: 9; e. 85% identity to the amino acid sequence set forth in SEQ ID NO: 11; f. 85% identity to the amino acid sequence set forth in SEQ ID NO: 14; g. 85% identity to the amino acid sequence set forth in SEQ ID NO: 17; h. 85% identity to the amino acid sequence set forth in SEQ ID NO: 20; i. 85% identity to the amino acid sequence (Continued)

set forth in SEQ ID NO: 22; or j. 85% identity to the amino acid sequence set forth in SEQ ID NO: 25.

19 Claims, 32 Drawing Sheets

Specification includes a Sequence Listing.

(51) Int. Cl.

| | |
|---|---|
| ***C12N 1/20*** | (2006.01) |
| ***C12N 9/10*** | (2006.01) |
| ***C12P 5/00*** | (2006.01) |
| ***C12P 19/56*** | (2006.01) |
| ***A23L 27/30*** | (2016.01) |
| ***A23L 2/60*** | (2006.01) |

(52) U.S. Cl.

CPC ................. *C12N 1/16* (2013.01); *C12N 1/20* (2013.01); *C12N 9/1051* (2013.01); *C12P 5/007* (2013.01); *C12P 19/56* (2013.01); *C12Y 204/01017* (2013.01)

(56) References Cited

U.S. PATENT DOCUMENTS

| | | | | |
|---|---|---|---|---|
| 2014/0329281 | A1* | 11/2014 | Houghton-Larsen | C12N 9/0071 435/78 |
| 2015/0037892 | A1 | 2/2015 | Wiessenhaan et al. | |
| 2015/0128306 | A1* | 5/2015 | Ono | C12P 19/44 800/298 |
| 2015/0159188 | A1* | 6/2015 | Ono | C07H 15/256 424/93.7 |
| 2015/0218533 | A1* | 8/2015 | Ono | C12N 15/8245 800/298 |
| 2015/0252401 | A1* | 9/2015 | Wang | C12P 19/56 435/78 |
| 2016/0010133 | A1* | 1/2016 | Park | C12P 19/56 536/18.1 |
| 2016/0153017 | A1 | 6/2016 | Van Der Hoeven et al. | |
| 2016/0186225 | A1* | 6/2016 | Mikkelsen | A23L 2/60 426/590 |
| 2016/0251635 | A1* | 9/2016 | Mao | A23G 3/38 426/3 |
| 2017/0218419 | A1* | 8/2017 | Kishore | C12P 19/56 |
| 2017/0275666 | A1* | 9/2017 | Prakash | C12P 19/56 |
| 2017/0314011 | A1 | 11/2017 | Roubos et al. | |
| 2017/0332673 | A1* | 11/2017 | Philippe | A23L 2/60 |

FOREIGN PATENT DOCUMENTS

| | | | | |
|---|---|---|---|---|
| WO | 2004/099381 | A2 | 11/2004 | |
| WO | 2006/009434 | A1 | 1/2006 | |
| WO | 2006096130 | A1 | 9/2006 | |
| WO | WO-2011153378 | A1 * | 12/2011 | C12N 15/8243 |
| WO | 2013/022989 | A2 | 2/2013 | |
| WO | 2013/076280 | A1 | 5/2013 | |
| WO | 2013/110673 | A1 | 8/2013 | |
| WO | 2013/135728 | A1 | 9/2013 | |
| WO | 2013/144257 | A1 | 10/2013 | |
| WO | 2014/191581 | A2 | 12/2014 | |
| WO | 2014191580 | A1 | 12/2014 | |
| WO | 2015/007748 | A1 | 1/2015 | |
| WO | 2015/014969 | A1 | 2/2015 | |

OTHER PUBLICATIONS

Database Geneseq [Online] (Sep. 12, 2013), "Stevia Rebaudiana UGT2 gene, SEQ: 87.", XP002757289, retrieved from EBI accession No. GSN:BAR69149 Database accession No. BAR69149, L: Sequence Information for W02013/110673; sequence.

Database Geneseq [Online] (Sep. 12, 2013), "Stevia Rebaudiana UGT2 protein, SEQ: 88.", XP002757288, retrieved from EBI accession No. GSP:BAR69150, Database accession No. BAR69150 L: Sequence Information for W02013/110673; sequence.

Database Geneseq [Online] (Apr. 11, 2013), "Stevia rebaudiana UGT 91d2e polypeptide, SEQ ID:5.", XP002757294, retrieved from EBI accession No. GSP:BAK52046, Database accession No. BAK52046 L: Sequence Information for W02013/022989; sequence.

Database Geneseq [Online] (Jan. 29, 2015), "Stevia rebaudiana UDP-glycosyltransferase (UGT) protein (UGT2 la) SEQ 88.", XP002757290, retrieved from EBI accession No. GSP:BBQ97923 Database accession No. BBQ97923 L: Sequence Information for W02014/191580; sequence.

Database Geneseq [Online] (Jan. 29, 2015), "S. rebaudiana UDP-glycosyltransferase (UGT) protein (UGT2 Ib), SEQ 100.", XP002757291, retrieved from EBI accession No. GSP:BBQ97935, Database accession No. BBQ97935 L: Sequence Information for W02014/191580; sequence.

Database Geneseq [Online] (Jan. 29, 2015), "Stevia rebaudiana UGT2 protein, SEQ: 88.", XP002757293, retrieved from EBI accession No. GSP:BBR03844 Database accession No. BBR03844 L: Sequence Information for W02014/191581; sequence.

Database Geneseq [Online] (Mar. 26, 2015), "Stevia rebaudiana UDP-glycosyltransferase (UGT) protein, SEQ ID 100.", XP002757292, retrieved from EBI accession No. GSP:BBU39053 Database accession No. BBU39053 L: Sequence Information for W02015/014969; sequence.

Praveen Guleria et al: "Insights into Steviol Glycoside Biosynthesis Pathway Enzymes Through Structural Homology Modeling", American Journal of Biochemistry and Molecular Biology, vol. 3, No. 1, (Oct. 4, 2012), pp. 1-19, XP055270235.

Praveen Guleria et al: "Agrobacterium Mediated Transient Gene Silencing (AMTS) in Stevia rebaudiana: Insights into Steviol Glycoside Biosynthesis Pathway", Plos One, vol. 8, No. 9, (Sep. 4, 2013), p. e74731, XP055269932.

Csernetics et al. "Expression of three isoprenoid biosynthesis genes and their effects on the carotenoid production of the zygomycete Mucor circinelloides", Fungal Genetics and Biology, No. 24 (2011) pp. 696-703.

Velayos et al. "Expression of the carG gene, encoding geranylgeranyl pyrophosphate synthase, is up-regulated by blue light in Mucor circinelloides", Curr Genet (2003) vol. 43, pp. 112-120.

Gueldener, Ulrich et al., "A new efficient gene disruption cassette for repeated use in budding yeast", Nucleic Acids Research, 1996, pp. 2519-2524, vol. 24, No. 13.

Lambert, Jolanda M. et al., "Cre-Iox-Based System for Multiple Gene Deletions and Selectable-Marker Removal in Lactobacillus plantarum", Applied and Environmental Microbiology, Feb. 2007, pp. 1126-1135, vol. 73, No. 4.

* cited by examiner

Steviol

Steviol-19-O-glucoside

Steviol-13-O-glucoside

Rubusoside

Steviolbioside

Rebaudioside

Stevioside

Rebaudioside A

Rebaudioside E

Rebaudioside D

Rebaudioside M

UDP-GLYCOSYLTRANSFERASES

FIELD OF THE INVENTION

The present invention relates to a recombinant host comprising a recombinant nucleic acid sequence encoding a variant UDP-glycosyltransferase (UGT) polypeptide. The invention also relates to a process for the preparation of a glycosylated diterpene using such a recombinant host and to a fermentation broth which may be the result of such a process. The invention further relates to a glycosylated diterpene obtained by such a process or obtainable from such a fermentation broth and to a composition comprising two or more such glycosylated diterpenes. In addition the invention relates to a foodstuff, feed or beverage which comprises such a glycosylated diterpene or a such composition. The invention also relates to a method for converting a first glycosylated diterpene into a second glycosylated diterpene using the above-mentioned recombinant host. Furthermore, the invention relates to variant UGT polypeptides, to nucleic acid sequences encoding such polypeptides, to a nucleic acid construct comprising such a polynucleotide sequence and to a method for producing the variant UGT polypeptides using the above-mentioned recombinant host.

BACKGROUND TO THE INVENTION

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic dipterepene steviol, which then proceeds through a multi-step glycosylation pathway to form the various steviol glycosides. However, yields may be variable and affected by agriculture and environmental conditions. Also, *Stevia* cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A and rebaudioside D.

Further improvement of such microoganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

SUMMARY OF THE INVENTION

In *Stevia rebaudiana*, steviol is synthesized from GGPP, which is formed by the deoxyxylulose 5-phosphate pathway. The activity of two diterpene cyclases (−)-copalyl diphosphate synthase (CPS) and (−)-kaurene synthase (KS) results in the formation of (−)-Kaurene which is then oxidized in a three step reaction by (−)-kaurene oxidase (KO) to form (−)-kaurenoic acid.

In *Stevia rebaudiana* leaves, (−)-kaurenoic acid is then hydroxylated, by ent-kaurenoic acid 13-hydroxylase (KAH) to form steviol. Steviol is then glycosylated by a series of UDP-glycosyltransferases (UGTs) leading to the formation of a number of steviol glycosides. Specifically, these molecules can be viewed as a steviol molecule, with its carboxyl hydrogen atom replaced by a glucose molecule to form an ester, and an hydroxyl hydrogen with combinations of glucose and rhamnose to form an acetal.

These pathways may be reconstructed in recombinant hosts, for example yeasts such as *Saccharomyces* and *Yarrowia*.

The invention relates to the identification of new variant UDP-glycosyltransferase (UGT) polypeptides, typically having improved properties in comparison to those that are currently known. These polypeptides may be used to generate recombinant hosts that produce higher amounts of steviol glycosides and/or additional or new steviol glycosides and/or higher amounts of specific steviol glycosides and/or mixtures of steviol glycosides having desired ratios of different steviol glycosides.

Thus, the invention also relates to a recombinant host capable of producing a glycosylated diterpene (i.e. a diterpene glycoside such as a steviol glycoside), such as steviolmonoside, steviolbioside, stevioside, rebaudioside A, rebaudioside B, rebaudioside C, rebaudioside D, rebaudioside E, rebaudioside F, rebaudiosideM, rubusoside, dulcoside A, steviol-13-monoside, steviol-19-monoside or 13-[(β-D-Glucopyranosyl)oxy)kaur-16-en-18-oic acid 2-O-β-D-glucopyranosyl-β-D-glucopyranosyl ester steviol-19-diside, Accordingly, the invention relates to a recombinant host comprising a recombinant nucleic acid sequence, typically having UDP-glycosyltransferase (UGT) activity such as UGT2 activity, encoding a polypeptide having at least about:

a. 85% identity to the amino acid sequence set forth in SEQ ID NO: 1;
b. 85% identity to the amino acid sequence set forth in SEQ ID NO: 3;
c. 85% identity to the amino acid sequence set forth in SEQ ID NO: 6;
d. 85% identity to the amino acid sequence set forth in SEQ ID NO: 9;
e. 85% identity to the amino acid sequence set forth in SEQ ID NO: 11;
f. 85% identity to the amino acid sequence set forth in SEQ ID NO: 14;
g. 85% identity to the amino acid sequence set forth in SEQ ID NO: 17;
h. 85% identity to the amino acid sequence set forth in SEQ ID NO: 20;

i. 85% identity to the amino acid sequence set forth in SEQ ID NO: 22; or j. 85% identity to the amino acid sequence set forth in SEQ ID NO: 25.

The invention also relates to:

a process for the preparation of a glycosylated diterpene which comprises fermenting a recombinant host of the invention in a suitable fermentation medium, and optionally recovering the glycosylated diterpene;

a fermentation broth comprising a glycosylated diterpene obtainable by the process of the invention;

a glycosylated diterpene obtained by such a process or obtainable from such a fermentation broth;

a composition comprising two or more such diterpenes;

a foodstuff, feed or beverage which comprises such a glycosylated diterpene;

a method for converting a first glycosylated diterpene into a second glycosylated diterpene, which method comprises:

contacting said first glycosylated diterpene with a recombinant host of the invention, a cell free extract derived from such a recombinant host or an enzyme preparation derived from either thereof;

thereby to convert the first glycosylated diterpene into the second glycosylated diterpene.

a polypeptide having UGT2 activity, wherein said polypeptide is selected from the group consisting of:

(a) a polypeptide comprising an amino acid sequence as set out in any one of SEQ ID NOs: 1, 3, 6, 9, 11, 14, 17, 20, 22 or 25; or (b) a polypeptide comprising an amino acid sequence having at least about 85% sequence identity with the amino acid sequence of any one of SEQ ID NOs: 1, 3, 6, 9, 11, 14, 17, 20, 22 or 25; or (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or (d) a polypeptide encoded by a polynucleotide comprising a polynucleotide sequence having at least 50% sequence identity to the polypeptide coding sequence in any one SEQ ID NOs: 2, 4, 5, 7, 8, 10, 12, 13, 15, 16, 18, 19, 21, 23, 24 or 26; or (e) a polypeptide encoded by a polynucleotide which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or (f) a polypeptide encoded by a polynucleotide which hybridises, preferably under at least low stringency conditions, with the complementary strand of a polynucleotide having at least 50% sequence identity to any one SEQ ID NOs: 2, 4, 5, 7, 8, 10, 12, 13, 15, 16, 18, 19, 21, 23, 24 or 26; or (g) a fragment of a polypeptide as defined in (a), (b), (c), (d), (e) or (f).

a polynucleotide sequence coding for such a polypeptide;

a nucleic acid construct comprising such a polynucleotide sequence; and a method of producing the polypeptide of the invention, comprising:

(a) cultivating a recombinant host of the invention under conditions conducive to the production of the polypeptide by the host cell, and optionally, (b) recovering the polypeptide.

BRIEF DESCRIPTION OF THE DRAWINGS

FIG. 12 sets out the production of rebaudiosideM in *Saccharomyces* strains expressing different variants of UGT2, as a percentage of the rebaudioside M production in a *Saccharomyces* strain expressing UGT2_1a.

FIG. 13 sets out the map of plasmid MB6969, carrying genes tHMG and UGT2_1a

FIG. 29 sets out the production of rebaudioside M in *Yarrowia* strains expressing different variants of UGT2, as a percentage of the rebaudioside M production in a *Yarrowia* strain expressing UGT2_1a.

DESCRIPTION OF THE SEQUENCE LISTING

Figure 1:
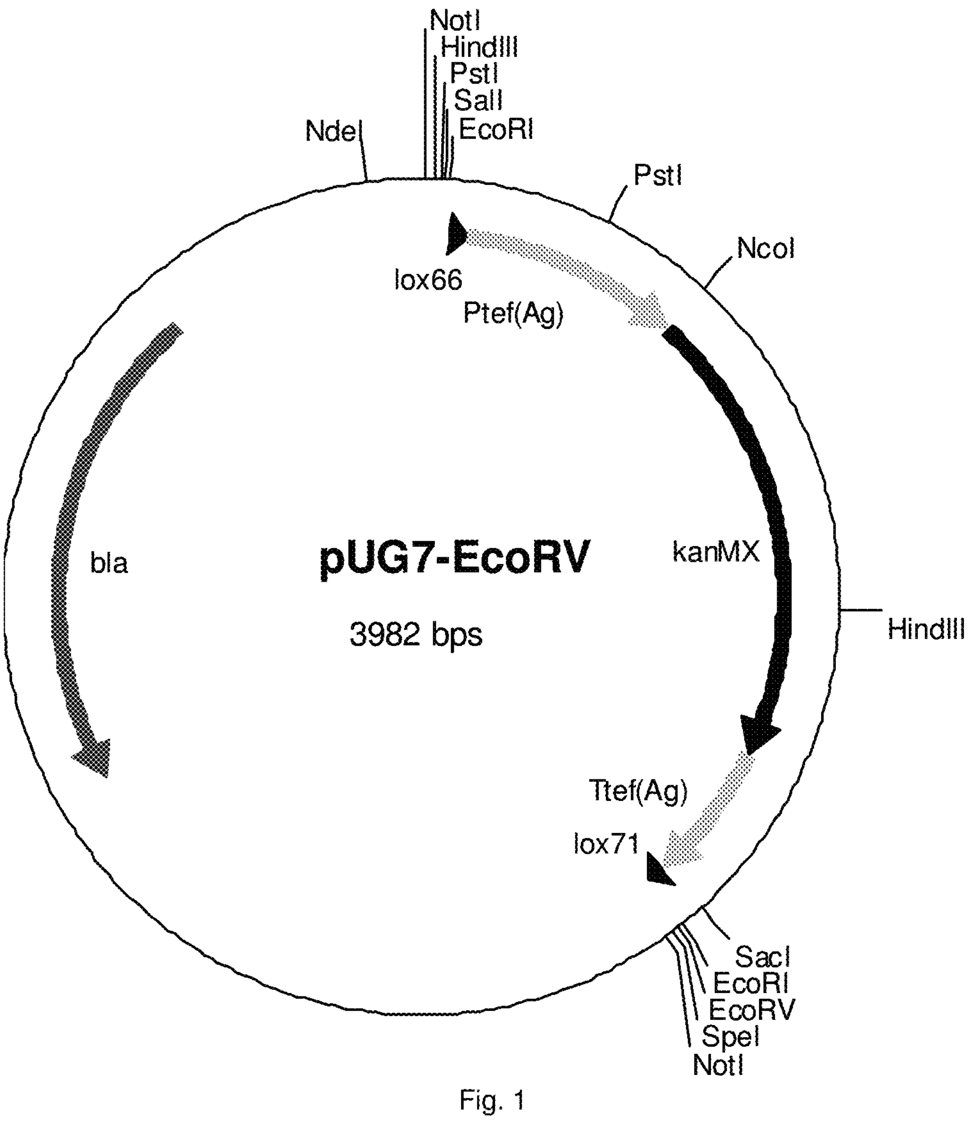
FIG. 1 sets out a schematic representation of the plasmid pUG7-EcoRV.

A description of the sequences is set out in Table 13. Sequences described herein may be defined with reference to the sequence listing or with reference to any database accession numbers set out herein, for example in Table 13.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Herein, "rebaudioside" may be shortened to "reb". That is rebaudioside A and rebA, for example, are intended to indicate the same molecule.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. The term "recombinant" is synonymous with "genetically modified".

The invention relates to new variant polypeptides having UDP-glycosyltransferase (UGT) activity. For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose). A polypeptide of the invention typically has UGT activity and a polynucleotide sequence of the invention typically encodes such a polypeptide. Typically, the polypeptides of the invention are variant polypeptides having UGT2-type activity.

According to the invention, there is thus provided a polypeptide, typically one having UGT activity, wherein said polypeptide is selected from the group consisting of:

(a) a polypeptide comprising an amino acid sequence as set out in any one of SEQ ID NOs: 1, 3, 6, 9, 11, 14, 17, 20, 22 or 25; or (b) a polypeptide comprising an amino acid sequence having at least about 85% sequence identity with the amino acid sequence of any one of SEQ ID NOs: 1, 3, 6, 9, 11, 14, 17, 20, 22 or 25; or (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or (d) a polypeptide encoded by a polynucleotide comprising a polynucleotide sequence having at least 50% sequence identity to the polypeptide coding sequence in any one SEQ ID NOs: 2, 4, 5, 7, 8, 10, 12, 13, 15, 16, 18, 19, 21, 23, 24 or 26; or (e) a polypeptide encoded by a polynucleotide which hybridizes, preferably under at least low stringency conditions, with the complementary strand of any one SEQ ID NOs: 2, 4, 5, 7, 8, 10, 12, 13, 15, 16, 18, 19, 21, 23, 24 or 26; or (f) a polypeptide encoded by a polynucleotide which hybridizes, preferably under at least low stringency conditions, with the complementary strand of a polynucleotide having at least 50% sequence identity to any one SEQ ID NOs: 2, 4, 5, 7, 8, 10, 12, 13, 15, 16, 18, 19, 21, 23, 24 or 26; or (g) a fragment of a polypeptide as defined in (a), (b), (c), (d), (e) or (f).

Such a polypeptide may comprise an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to any one of SEQ ID NOs: 1, 3, 6, 9, 11, 14, 17, 20, 22 or 25.

Thus, the invention relates to:

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 1;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO 3;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 6;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 9;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 11;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 14;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 17;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 20;

a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 22; and a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 25.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide of the invention may comprise a signal peptide and/or a propeptide sequence. In the event that a polypeptide of the invention comprises a signal peptide and/or a propeptide, sequence identity may be calculated over the mature polypeptide sequence.

Figure 31:
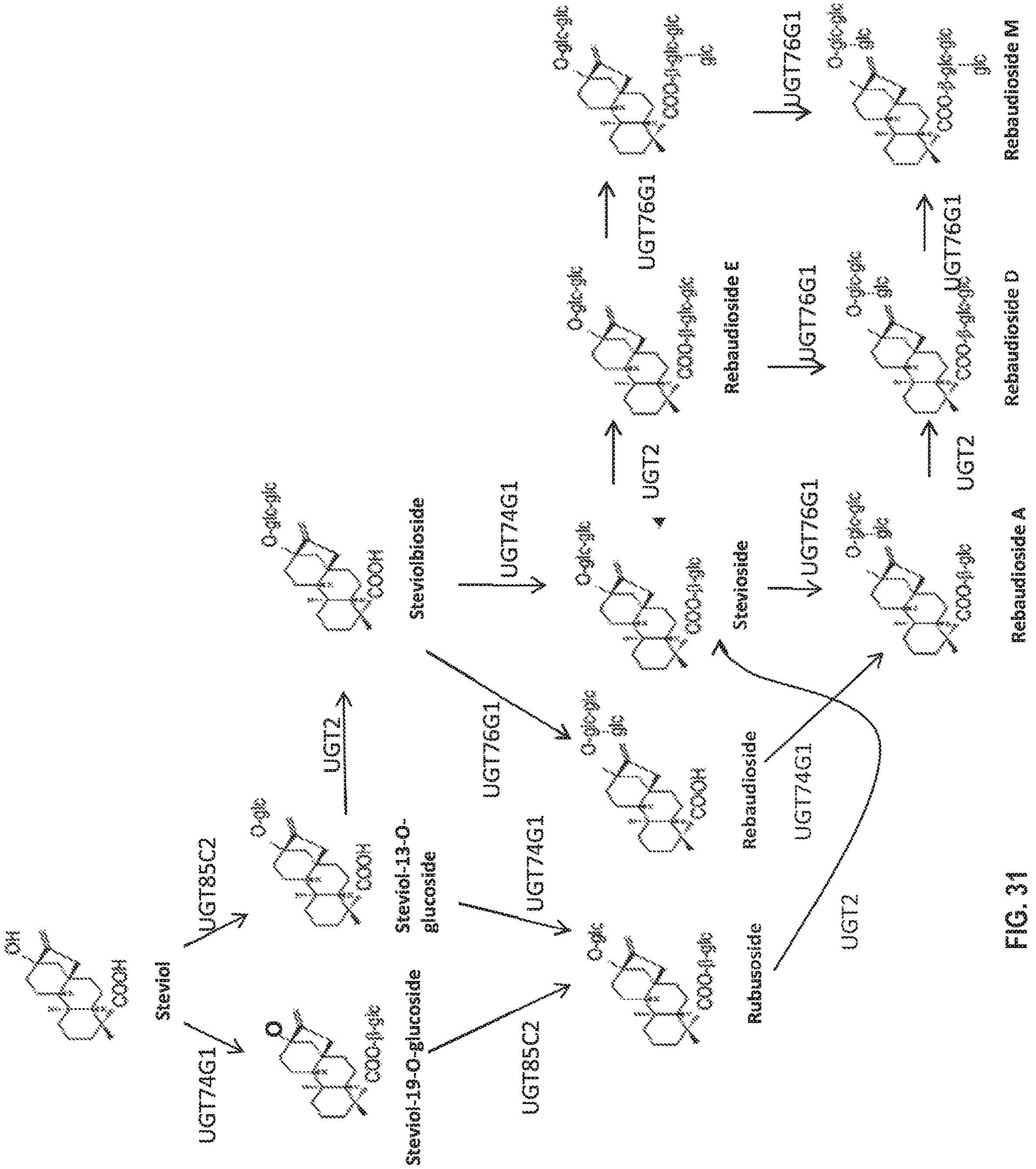
FIG. 31 sets out sets out a schematic diagram of the potential pathways leading to biosynthesis of steviol glycosides.
Figure 32:
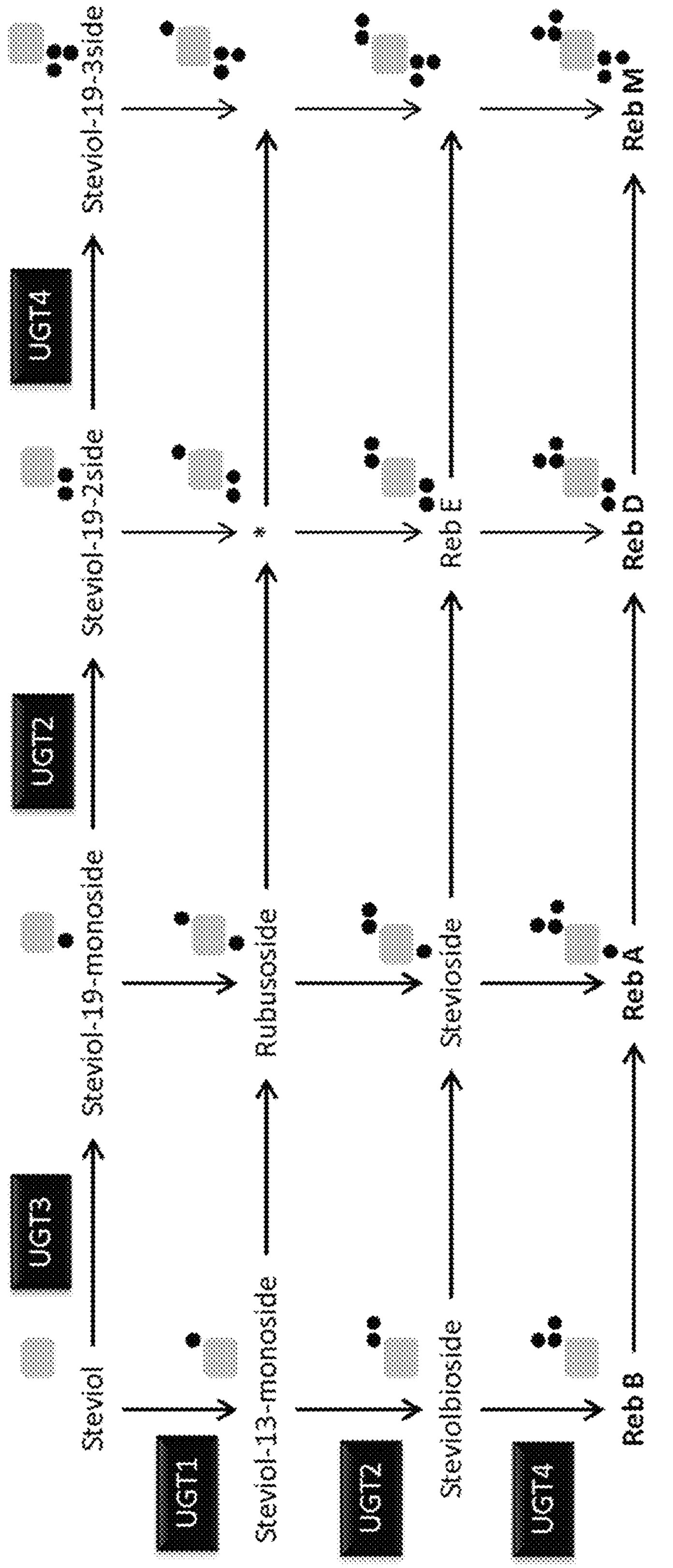
FIG. 32 sets out sets out a schematic diagram of the potential pathways leading to biosynthesis of steviol glycosides. The compound shown with an asterisk is 13-[(β-D-Glucopyranosyl)oxy)kaur-16-en-18-oic acid 2-O-β-D-glucopyranosyl-β-D-glucopyranosyl ester

A polypeptide of the invention typically has UGT activity and more preferably has UGT2 activity. FIGS. 31 and 32 illustrate a non-exhaustive list of reactions that may be catalyzed by a polypeptide having UGT2.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., a functional UGT2 polypeptide may utilize stevioside as a substrate, transferring a glucose moiety to the C-2' of the 19-O-glucose residue to produce rebaudioside E. A functional UGT2 polypeptide may also utilize rebaudioside A as a substrate, transferring a glucose moiety to the C-2' of the 19-O-glucose residue to produce rebaudioside D.

A polypeptide having UGT2 activity may also catalyze reactions that utilize steviol-19-glucoside or rubusoside as a substrate, e.g., a functional UGT2 polypeptide may utilize steviol-19-glucoside or rubusoside as a substrate, transferring a glucose moiety to the 19 position to produce steviol-19-2side or 13-[(β-D-Glucopyranosyl)oxy)kaur-16-en-18-oic acid 2-O-β-D-glucopyranosyl-β-D-glucopyranosyl ester respectively.

However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-O-glucoside transferase, transferring a rhamnose moiety to the C-2' of the 13-O-glucose of the acceptor molecule, steviol.

One or more of the above-described activities may be used to define a polypeptide having UGT2 activity. A polypeptide of the invention may have improved UGT2 activity in respect of one or more of the above-described activities in comparison with the UGT2_1a polypeptide (SEQ ID NO: 27).

A polypeptide of the invention may be used to steer production of steviol glycosides in a recombinant cell to a desired steviol glycoside, such as rebaudioside A, rebaudioside D or rebaudioside M. For example, a UGT2 polypeptide which preferentially catalyzes conversion of steviol-13-monoside to steviolbioside and/or conversion of rubusoside to stevioside may help to steer production towards rebaudiosideA, whereas a UGT2 polypeptide which preferentially catalyzes conversion of stevioside to rebE or rubusoside to a compound with an additional sugar at the 19 position may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M.

The invention further provides a polynucleotide sequence coding for a polypeptide as described herein.

Such a polynucleotide sequence may be selected from the group consisting of:

(a) a polynucleotide sequence comprising any one of SEQ ID NOs: 2, 4, 5, 7, 8, 10, 12, 13, 15, 16, 18, 19, 21, 23, 24 or 26 or comprising a polynucleotide sequence having at least 30% sequence identity with the polynucleotide sequence of any one of SEQ ID NOs: 2, 4, 5, 7, 8, 10, 12, 13, 15, 16, 18, 19, 21, 23, 24 or 26; or (b) a polynucleotide sequence which hybridizes, preferably under at least low stringency conditions, with the complementary strand of any one SEQ ID NOs: 2, 4, 5, 7, 8, 10, 12, 13, 15, 16, 18, 19, 21, 23, 24 or 26.; or (c) a polynucleotide sequence which hybridizes, preferably under at least low stringency conditions with the complementary strand of a polynucleotide having at least 30% sequence identity to any one of any one SEQ ID NOs: 2, 4, 5, 7, 8, 10, 12, 13, 15, 16, 18, 19, 21, 23, 24 or 26;

(d) a polynucleotide sequence which is degenerate as a result of the degeneracy of the genetic code to a polynucleotide sequence as defined in any one of (a), (b) or (c); or (e) a polynucleotide sequence which is the complement of a nucleotide sequence as defined in (a), (b), (c) or (d).

A polynucleotide sequence of the invention may have a sequence identity of at least 40%, at least 50%, at least 60%, preferably at least 70%, more preferably at least 80%, most preferably at-least 90%, most preferably at least 93%, most preferably at least about 95%, most preferably at least about 96%, most preferably at least about 97%, even most preferably at least about 98%, and even more preferred at least 99% to any one of any one SEQ ID NOs: 2, 4, 5, 7, 8, 10, 12, 13, 15, 16, 18, 19, 21, 23, 24 or 26.

The term "nucleic acid" as used in the present invention refers to a nucleotide polymer including at least 5 nucleotide units. A nucleic acid refers to a ribonucleotide polymer (RNA), deoxynucleotide polymer (DNA) or a modified form of either type of nucleic acid or synthetic form thereof or mixed polymers of any of the above. Nucleic acids may include either or both naturally-occurring and modified nucleic acids linked together by naturally-occurring and/or non-naturally occurring nucleic acid linkages. The nucleic acid molecules may be modified chemically or biochemically or may contain non-natural or derivatized nucleic acid bases, as will be readily appreciated by those of skill in the art. Such modifications include, for example, labels, methylation, substitution of one or more of the naturally occurring nucleic acids with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term nucleic acid is also intended to include any topological conformation, including single-stranded (sense strand and antisense strand), double-stranded, partially duplexed, triplex, hairpinned, circular and padlocked conformations. Also included are synthetic molecules that mimic nucleic acids in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers. The term "nucleic acid", "polynucleotide" and "polynucleotide sequence" can be used interchangeably herein.

As used herein, the term "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleotide bases (nucleotides) of the strands of oligomeric compounds. For example, adenine and thymine are complementary nucleic acids which pair through the formation of hydrogen bonds. Hybridization can occur under varying circumstances. "Stringency hybridization" or "hybridizes under low stringency, medium stringency, high stringency, or very high stringency conditions" is used herein to describe conditions for hybridization and washing, more specifically conditions under which an oligomeric compound will hybridize to its target sequence, but to a minimal number of other sequences. So, the oligomeric compound will hybridize to the target sequence to a detectably greater degree than to other sequences. Guidance for performing hybridization reactions can be found in Current Protocols in Molecular Biology, John Wiley & Sons, N.Y. (1989), 6.3.1-6:3.6. Aqueous and non-aqueous methods are described in that reference and either can be used. Stringency conditions are sequence-dependent and will be different in different circumstances. Generally, stringency conditions are selected to be about 5° C. lower than the thermal melting point ($T_m$) for the oligomeric compound at a defined ionic strength and pH. The $T_m$ is the temperature (under defined ionic strength and pH) at which 50% of an oligomeric compound hybridizes to a perfectly matched probe. Stringency conditions may also be achieved with the addition of destabilizing agents such as formamide.

Examples of specific hybridization conditions are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

In general, high stringency conditions, such as high hybridization temperature and optionally low salt concentrations, permit only hybridization between sequences that are highly similar, whereas low stringency conditions, such as low hybridization temperature and optionally high salt concentrations, allow hybridization when the sequences are less similar.

The invention also provides a nucleic acid construct comprising the polynucleotide sequence of the invention.

The term "nucleic acid construct" refers to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

A nucleic acid of the invention may be an expression vector, wherein a polynucleotide sequence of the invention is operably linked to at least one control sequence for the expression of the polynucleotide sequence in a host cell.

The term "operably linked" as used herein refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

An expression vector comprises a polynucleotide coding for a polypeptide of the invention, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. A vector of the invention may comprise one or more selectable markers, which permit easy selection of transformed cells.

The invention also provides a recombinant host which comprises a recombinant nucleic acid sequence encoding a polypeptide of the invention.

That is to say, a recombinant host of the invention may comprise, for example, a recombinant nucleic acid sequence encoding a polypeptide having at least about:

a. 85% identity to the amino acid sequence set forth in SEQ ID NO: 1;
b. 85% identity to the amino acid sequence set forth in SEQ ID NO: 3;
c. 85% identity to the amino acid sequence set forth in SEQ ID NO: 6;
d. 85% identity to the amino acid sequence set forth in SEQ ID NO: 9;
e. 85% identity to the amino acid sequence set forth in SEQ ID NO: 11;
f. 85% identity to the amino acid sequence set forth in SEQ ID NO: 14;
g. 85% identity to the amino acid sequence set forth in SEQ ID NO: 17;
h. 85% identity to the amino acid sequence set forth in SEQ ID NO: 20;
i. 85% identity to the amino acid sequence set forth in SEQ ID NO: 22; or
j. 85% identity to the amino acid sequence set forth in SEQ ID NO: 25.

A recombinant host of the invention may comprise any polynucleotide encoding a polypeptide of the invention as described herein. A recombinant host of the invention is typically capable of expressing a polypeptide of the invention.

Typically, a recombinant host of the invention is capable of producing a glycosylated diterpene, such as a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A recombinant host according to the invention may comprise one or more recombinant nucleotide sequence(s) encoding one of more of:

- a polypeptide having ent-copalyl pyrophosphate synthase activity;
- a polypeptide having ent-Kaurene synthase activity;
- a polypeptide having ent-Kaurene oxidase activity; and
- a polypeptide having kaurenoic acid 13-hydroxylase activity.

For the purposes of this invention, a polypeptide having ent-copalyl pyrophosphate synthase (EC 5.5.1.13) is capable of catalyzing the chemical reaction:

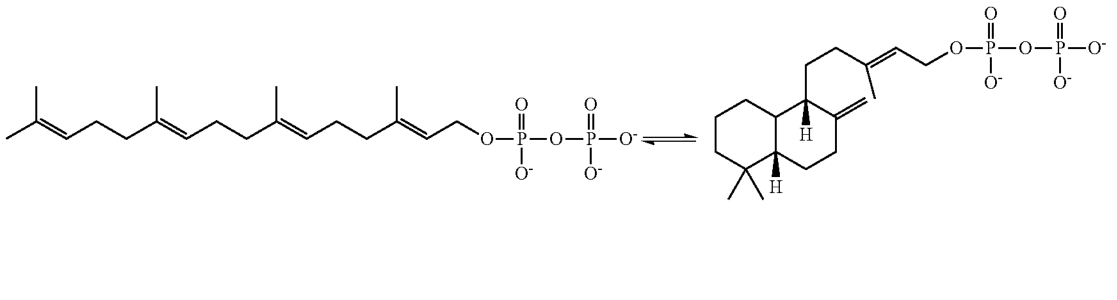

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

$$\text{ent-copalyl diphosphate} \rightleftharpoons \text{ent-kaurene+diphosphate}$$

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and $O_2$. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the invention may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

A recombinant host according to any one of the preceding claims which comprises a one or more recombinant nucleic acid sequences encoding one or more of:

(i) a polypeptide having UGT74G1 activity (UGT3 activity);

(ii) a polypeptide having UGT85C2 activity (UGT1 activity); and (iii) a polypeptide having UGT76G1 activity (UGT4 activity).

FIGS. 31 and 32 set out schematic diagram of the potential pathways leading to biosynthesis of steviol glycosides.

A recombinant host of the invention will typically comprise at least one recombinant nucleic acid encoding a polypeptide having UGT1 activity, at least one recombinant nucleic acid encoding a polypeptide having UGT2 activity, at least one recombinant nucleic acid encoding a polypeptide having UGT3 activity and at least one recombinant nucleic acid encoding a polypeptide having UGT4 activity. One nucleic acid may encode two or more of such polypeptides.

A nucleic acid encoding a polypeptide of the invention may be used to steer production of steviol glycosides in a recombinant cell to a desired steviol glycoside, such as rebaudioside A, rebaudioside D or rebaudioside M. For example, a recombinant nucleic acid which encodes a UGT2 polypeptide which preferentially catalyzes conversion of steviol-13-monoside to steviolbioside and/or conversion of rubusoside to stevioside may help to steer production towards rebaudiosideA, whereas a recombinant nucleic acid which encodes a UGT2 polypeptide which preferentially catalyzes conversion of stevioside to rebE or rubusoside to a compound with an additional sugar at the 19 position may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M.

A recombinant host of the invention may comprises a nucleotide sequence encoding a polypeptide capable of catalyzing the addition of a C-13-glucose to steviol. That is to say, a recombinant host of the invention may comprise a UGT which is capable of catalyzing a reaction in which steviol is converted to steviolmonoside.

Such a recombinant host of the invention may comprise a nucleotide sequence encoding a polypeptide having the activity shown by UDP-glycosyltransferase (UGT) UGT85C2, whereby the nucleotide sequence upon transformation of the host confers on that host the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant host of the invention may comprise a nucleotide sequence encoding a polypeptide having UGT activity may comprise a nucleotide sequence encoding a polypeptide capable of catalyzing the addition of a C-13-glucose to steviol or steviolmonoside. That is to say, a recombinant of the invention may comprise a UGT which is capable of catalyzing a reaction in which steviolmonoside is converted to steviolbioside. Accordingly, such a recombinant host may be capable of converting steviolmonoside to steviolbioside. Expression of such a nucleotide sequence may confer on the host the ability to produce at least steviolbioside.

A recombinant microorganism of the invention also comprises a nucleotide sequence encoding a polypeptide having UGT activity may comprise a nucleotide sequence encoding a polypeptide capable of catalyzing the addition of a C-19-glucose to steviolbioside. That is to say, a microorganism of the invention may comprise a UGT which is capable of catalyzing a reaction in which steviolbioside is converted to stevioside. Accordingly, such a microorganism may be capable of converting steviolbioside to stevioside. Expression of such a nucleotide sequence may confer on the microorganism the ability to produce at least stevioside.

A microorganism of the invention may thus also comprise a nucleotide sequence encoding a polypeptide having the activity shown by UDP-glycosyltransferase (UGT) UGT74G1, whereby the nucleotide sequence upon transformation of the microorganism confers on the cell the ability to convert steviolbioside to stevioside.

Suitable UGT74G1 polypeptides may be capable of transferring a glucose unit to the 13-OH or the 19-COOH, respectively, of steviol. A suitable UGT74G1 polypeptide may function as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant host of the invention may comprise a nucleotide sequence encoding a polypeptide capable of catalyzing glucosylation of the C-3' of the glucose at the C-13 position of stevioside. That is to say, a recombinant host of the invention may comprise a UGT which is capable of catalyzing a reaction in which stevioside to rebaudioside A. Accordingly, such a recombinant host may be capable of converting stevioside to rebaudioside A. Expression of such a nucleotide sequence may confer on the host the ability to produce at least rebaudioside A.

A recombinant microorganism of the invention may thus also comprise a nucleotide sequence encoding a polypeptide having the activity shown by UDP-glycosyltransferase (UGT) UGT76G1, whereby the nucleotide sequence upon transformation of the microorganism confers on the cell the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3' glucosyl transferase and a uridine 5'-diphospho glucosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences.

A recombinant host of the invention typically comprises nucleotide sequences encoding polypeptides having all four UGT activities described above. A given nucleic acid may encode a polypeptide having one or more of the above activities. For example, a nucleic acid encode for a polypeptide which has two, three or four of the activities set out above. Preferably, a recombinant host of the invention comprises UGT1, UGT2 and UGT3 and UGT4 activity. Suitable UGT1, UGT3 and UGT4 sequences are described in Table 1 of WO2015/007748.

A recombinant host of the invention may comprise a recombinant nucleic acid sequence encoding an additional polypeptide having UGT2 activity. That is to say, a recombinant host of the invention may comprise a nucleic acid sequence encoding a variant UGT2 of the invention and one or more additional, different, variant of the invention or any another, different, UGT2.

Use of a nucleic acid sequence encoding a UGT2_1b, UGT2_2b, UGT2_3b, UGT2_4b, UGT2_5b, UGT2_6b, UGT2_7b, UGT2_8b, UGT2_9b or UGT2_10b polypeptide (or related polypeptide as described herein) may be useful in improving rebA production.

Use of a nucleic acid sequence encoding a UGT2_7b polypeptide (or related polypeptide as described herein) may be useful in improving rebM production.

In a recombinant host of the invention, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host of the invention may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of the microorganism confer(s) on the microorganism the ability to produce elevated levels of GGPP. Thus, a recombinant host according to the invention may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant host of the invention may comprise nucleic acid sequences encoding one or more of:

a polypeptide having hydroxymethylglutaryl-CoA reductase activity;

a polypeptide having farnesyl-pyrophosphate synthetase activity;

a polypeptide having geranylgeranyl diphosphate synthase activity.

A host or host cell as defined herein is an organism suitable for genetic manipulation and one which may be cultured at cell densities useful for industrial production of a target product. A suitable host may be a microorganism, for example one which may be maintained in a fermentation device. A host cell may be a host cell found in nature or a host cell derived from a parent host cell after genetic manipulation or classical mutagenesis.

As used herein, a recombinant host is one which is genetically modified or transformed/transfected with one or more of the nucleotide sequences as defined herein. The presence of the one or more such nucleotide sequences alters the ability of the microorganism to produce diterpene glycosides, in particular one or more steviol glycosides. A non-recombinant host, i.e. one that is not transformed/transfected or genetically modified, typically does not comprise one or more of the nucleotide sequences enabling the cell to produce a diterpene glycoside. Hence, a non-recombinant host is typically a host that does not naturally produce a diterpene glycoside, although a host which naturally produces a diterpene or diterpene glycoside and which has been modified according to the invention (and which thus has an altered ability to produce a diterpene glycoside) is considered a recombinant host according to the invention.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase and NADPH-cytochrome p450 reductase are native to the host and that transformation with one or more of the nucleotide sequences encoding these enzymes may not be required to confer the host cell the ability to produce a diterpene glycoside. A preferred host according to the present invention may be a recombinant host which is naturally capable of producing GGPP (i.e. in its non-recombinant form).

Further improvement of diterpene glycoside production by the host microorganism may be obtained by classical strain improvement.

A host cell may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. “Fungi” include all species of the subdivision *Eumycotina* (Alexopoulos, C. J., 1962, In: Introductory Mycology, John Wiley & Sons, Inc., New York). The term fungus thus includes among others filamentous fungi and yeast.

“Filamentous fungi” are herein defined as eukaryotic microorganisms that include all filamentous forms of the subdivision *Eumycotina* and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*,), *Acinetobacter, Nocardia, Xanthobacter, Escherichia* (e.g., *E. coli* (e.g., strains DH 1 OB, StbI2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellii*)).

Host cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

The invention further provides a method for producing a polypeptide of the invention comprising:

(a) cultivating a recombinant host cell of the invention under conditions conducive to the production of the polypeptide by the host cell, and optionally, (b) recovering the polypeptide.

A recombinant host according to the present invention may be able to grow on any suitable carbon source known in the art and convert it to a glycosylated diterpene, e.g. a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the invention also provides a process for the preparation of a glycosylated diterpene, such as a steviol glycoside, which comprises fermenting a recombinant host of the invention which is capable of producing at least one glycosylated diterpene in a suitable fermentation medium, and optionally recovering the glycosylated diterpene.

The glycosylated terpene, for example a steviol glycoside, may be stevio-19-monoside, steviol-19-diside, steviol-19-3side, steviol-13-monoside, rubusoside, 13-[(β-D-Glucopyranosyl)oxy)kaur-16-en-18-oic acid 2-O-β-D-glucopyranosyl-β-D-glucopyranosyl ester, steviolbioside, stevioside, rebaudioside E, rebaudioside B, rebaudioside A, rebaudioside D or rebaudioside M. Thus, the invention provides a process for the production of one or more such steviol glycosides.

The fermentation medium used in the process for the production of a glycosylated diterpene may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as urea, or an ammonium salt such as ammonium sulphate, ammonium chloride, ammonium nitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicellulose or pectin is used as a carbon source in the fermentation process, where it may be necessary to add hydrolytic enzymes, such as cellulases, hemicellulases or pectinases to hydrolyse the substrate.

The recombinant host used in the process for the preparation of a glycosylated diterpene may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host according to the present invention may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a glycosylated diterpene according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a glycosylated diterpene in the process according to the present invention may occur during the growth phase of the host cell, during the stationary (steady state) phase or during both phases. It may be possible to run the fermentation process at different temperatures.

The process for the production of a glycosylated diterpene may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a glycosylated diterpene according to the present invention may be carried out at any suitable pH value. If the recombinant host is a yeast, the pH in the fermentation medium preferably has a value of below 6, preferably below 5.5, preferably below 5, preferably below 4.5, preferably below 4, preferably below pH 3.5 or below pH 3.0, or below pH 2.5, preferably above pH 2. An advantage of carrying out the fermentation at these low pH values is that growth of contaminant bacteria in the fermentation medium may be prevented.

Such a process may be carried out on an industrial scale. The product of such a process is one or more glycosylated diterpenes, such as one or more steviol glycosides, for example one or more of 13-[(β-D-Glucopyranosyl)oxy) kaur-16-en-18-oic acid 2-O-β-D-glucopyranosyl-β-D-glucopyranosyl ester, steviolbioside, stevioside, rebaudioside E, rebaudioside B, rebaudioside A, rebaudioside D or rebaudioside M.

Recovery of glycosylated diterpene(s) from the fermentation medium may be performed by known methods in the art, for instance by distillation, vacuum extraction, solvent extraction, or evaporation.

In the process for the production of a glycosylated diterpene according to the invention, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, for example above 20 g/l, but usually up to a concentration of about 200 g/l, such as up to about 150 g/l, such as up to about 100 g/l, for example up to about 70 g/l. Such concentrations may be concentration of the total broth or of the supernatant.

The invention further provides a fermentation broth comprising a glycosylated diterpene obtainable by the process of the invention for the preparation of a glycosylated diterpene.

In the event that one or more glycosylated diterpenes is expressed within the microorganism, such cells may need to be treated so as to release them. Preferentially, at least one glycosylated diterpene, such as a steviol glycoside, for example rebA or rebM, is produced extracellularly.

The invention also provides a glycosylated diterpene obtained by a process according to the invention for the preparation of a glycosylated diterpene or obtainable from a fermentation broth of the invention. Such a glycosylated diterpene may be a non-naturally occurring glycosylated diterpene, that is to say one which is not produced in plants.

Also provided is a composition comprising two or more glycosylated diterpenes obtainable by a process of the invention for the preparation of a glycosylated diterpene or obtainable from a fermentation broth of the invention. In such a composition, one or more of the glycosylated diterpenes may be a non-naturally occurring glycosylated diterpene, that is to say one which is not produced in plants.

Furthermore, the invention provides a method for converting a first glycosylated diterpene into a second glycosylated diterpene, which method comprises:

contacting said first glycosylated diterpene with a recombinant host of the invention, a cell free extract derived from such a recombinant host or an enzyme preparation derived from either thereof;

thereby to convert the first glycosylated diterpene into the second glycosylated diterpene.

In such a method, the second glycosylated diterpene may be steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

In such a method, the first glycosylated diterpene may be steviol-13-monoside, steviol-19-monoside, rubusoside, stevioside, rebaudioside A or 13-[(β-D-Glucopyranosyl)oxy) kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

These are the first and second steviol glycosides in relation to a reaction catalysed by a polypeptide of the invention having UGT2 activity.

That is to say, the invention relates to a method of bioconversion or biotransformation.

A steviol glycoside or composition produced by the fermentation process according to the present invention may be used in any application known for such compounds. In particular, they may for instance be used as a sweetener, for example in a food or a beverage. According to the invention therefore, there is provided a foodstuff, feed or beverage which comprises a glycosylated diterpene such as a steviol glycoside or a composition of the invention.

For example a glycosylated diterpene or a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a glycosylated diterpene or a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a diterpene or glycosylated prepared according to a process of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

The glycosylated diterpene, for example a steviol glycoside, or a composition of the invention can be used in dry or liquid forms. It can be added before or after heat treatment of food products. The amount of the sweetener depends on the purpose of usage. It can be added alone or in the combination with other compounds.

Compounds produced according to the method of the invention may be blended with one or more further non-calorific or calorific sweeteners. Such blending may be used to improve flavour or temporal profile or stability. A wide range of both non-calorific and calorific sweeteners may be suitable for blending with a glycosylated diterpene or a composition of the invention. For example, non-calorific sweeteners such as mogroside, monatin, aspartame, acesulfame salts, cyclamate, sucralose, saccharin salts or erythritol. Calorific sweeteners suitable for blending with a glycosylated diterpene or a composition of the invention include sugar alcohols and carbohydrates such as sucrose, glucose, fructose and HFCS. Sweet tasting amino acids such as glycine, alanine or serine may also be used.

A glycosylated diterpene or a composition of the invention can be used in the combination with a sweetener suppressor, such as a natural sweetener suppressor. It may be combined with an umami taste enhancer, such as an amino acid or a salt thereof.

A glycosylated diterpene or a composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition with a glycosylated diterpene or a composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A glycosylated diterpene or a composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a glycosylated diterpene or a composition of the invention may be used as a sweetener not only for drinks, foodstuffs, and other products dedicated for human consumption, but also in animal feed and fodder with improved characteristics.

The examples of products where a glycosylated diterpene or a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

A glycosylated diterpene or a composition of the invention can be used in dry or liquid forms. It can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present invention can be made by any method known to those skilled in the art that provide homogenous even or homogeneous mixtures of the ingredients. These methods include dry blending, spray drying, agglomeration, wet granulation, compaction, co-crystallization and the like.

In solid form a glycosylated diterpene or a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

The composition may include various bulking agents, functional ingredients, colorants, flavors.

The terms “sequence homology” or “sequence identity” are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, word length=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov.

Embodiments of the Invention

1. A recombinant host comprising a recombinant nucleic acid sequence encoding a polypeptide having at least about:
   a. 85% identity to the amino acid sequence set forth in SEQ ID NO: 1;
   b. 85% identity to the amino acid sequence set forth in SEQ ID NO: 3;
   c. 85% identity to the amino acid sequence set forth in SEQ ID NO: 6;
   d. 85% identity to the amino acid sequence set forth in SEQ ID NO: 9;
   e. 85% identity to the amino acid sequence set forth in SEQ ID NO: 11;
   f. 85% identity to the amino acid sequence set forth in SEQ ID NO: 14;
   g. 85% identity to the amino acid sequence set forth in SEQ ID NO: 17;
   h. 85% identity to the amino acid sequence set forth in SEQ ID NO: 20;
   i. 85% identity to the amino acid sequence set forth in SEQ ID NO: 22; or
   j. 85% identity to the amino acid sequence set forth in SEQ ID NO: 25.
2. A recombinant host according to embodiment 1 which is capable of producing a glycosylated diterpene, such as a steviol glycoside.
3. A recombinant host according to embodiment 1 or 2 which comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.
4. A recombinant host according to any one of the preceding embodiments, which comprises a recombinant nucleic acid sequence encoding a polypeptide having NADPH-cytochrome p450 reductase activity.
5. A recombinant host according to any one of the preceding embodiments which comprises a recombinant nucleic acid sequence encoding one or more of:
   (i) a polypeptide having UGT74G1 (UGT3) activity;
   (ii) a polypeptide having UGT85C2 (UGT1) activity; and
   (iii) a polypeptide having UGT76G1 (UGT4) activity.
6. A recombinant host according to any one of the preceding embodiments which comprises a recombinant nucleic acid sequence encoding an additional polypeptide having UGT2 activity.
7. A recombinant host according to any one of the preceding embodiments, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.
8. A recombinant host according to embodiment 7, wherein the recombinant host is a *Saccharomyces cerevisiae* cell, a *Yarrowia lipolitica* cell, a *Candida krusei* cell, an *Issatchenkia orientalis* or an *Escherichia coli* cell.
9. A recombinant host according to any one of the preceding embodiments, wherein the ability of the host to produce geranylgeranyl diphosphate (GGPP) is upregulated.
10. A recombinant host according to any one of the preceding embodiments, comprising one or more recombinant nucleic acid sequence(s) encoding hydroxymethylglutaryl-CoA reductase, farnesyl-pyrophosphate synthetase and geranylgeranyl diphosphate synthase.
11. A recombinant host according to any one of the preceding embodiments which comprises a nucleic acid sequence encoding one or more of:
    a polypeptide having hydroxymethylglutaryl-CoA reductase activity;
    a polypeptide having farnesyl-pyrophosphate synthetase activity;
    a polypeptide having geranylgeranyl diphosphate synthase activity.
12. A process for the preparation of a glycosylated diterpene which comprises fermenting a recombinant host according to any one of embodiments 2 to 11 in a suitable fermentation medium, and optionally recovering the glycosylated diterpene.
13. A process according to any one of embodiment 12 for the preparation of a glycosylated diterpene, wherein the process is carried out on an industrial scale.
14. A fermentation broth comprising a glycosylated diterpene obtainable by the process according to embodiment 12 or 13.
15. A glycosylated diterpene obtained by a process according to embodiment 12 or 13 or obtainable from a fermentation broth according to embodiment 14.
16. A composition comprising two or more glycosylated diterpenes obtained by a process according to embodiment 12 or 13 or obtainable from a fermentation broth according to embodiment 14.
17. A foodstuff, feed or beverage which comprises a glycosylated diterpene according to embodiment 15 or a composition according to embodiment 16.
18. A method for converting a first glycosylated diterpene into a second glycosylated diterpene, which method comprises:
    contacting said first glycosylated diterpene with a recombinant host according to any one of embodiments 1 to 11, a cell free extract derived from such a recombinant host or an enzyme preparation derived from either thereof;
    thereby to convert the first glycosylated diterpene into the second glycosylated diterpene.
19. A method according to embodiment 18, wherein the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

20. A method according to claim 19, wherein the first glycosylated diterpene is steviol-13-monoside, steviol-19-monoside, rubusoside, stevioside, rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

21. A polypeptide having UGT2 activity, wherein said polypeptide is selected from the group consisting of:
   (a) a polypeptide comprising an amino acid sequence as set out in any one of SEQ ID NOs: 1, 3, 6, 9, 11, 14, 17, 20, 22 or 25; or
   (b) a polypeptide comprising an amino acid sequence having at least about 85% sequence identity with the amino acid sequence of any one of SEQ ID NOs: 1, 3, 6, 9, 11, 14, 17, 20, 22 or 25; or
   (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or
   (d) a polypeptide encoded by a polynucleotide comprising a polynucleotide sequence having at least 30% sequence identity to the polypeptide coding sequence in any one SEQ ID NOs: 2, 4, 5, 7, 8, 10, 12, 13, 15, 16, 18, 19, 21, 23, 24 or 26; or
   (e) a polypeptide encoded by a polynucleotide which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or
   (f) a polypeptide encoded by a polynucleotide which hybridises, preferably under at least low stringency conditions, with the complementary strand of a polynucleotide having at least 30% sequence identity to any one SEQ ID NOs: 2, 4, 5, 7, 8, 10, 12, 13, 15, 16, 18, 19, 21, 23, 24 or 26; or
   (g) a fragment of a polypeptide as defined in (a), (b), (c), (d), (e) or (f).

22. A polypeptide according to embodiment 21, comprising a polypeptide having an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to any one of SEQ ID NOs: 1, 3, 6, 9, 11, 14, 17, 20, 22 or 25.

23. A polynucleotide sequence coding for a polypeptide according to embodiment 21 or 22.

24. A polynucleotide sequence according to embodiment 23, wherein the polynucleotide sequence is selected from the group consisting of:
   (a) a polynucleotide sequence comprising any one of SEQ ID NOs: 2, 4, 5, 7, 8, 10, 12, 13, 15, 16, 18, 19, 21, 23, 24 or 26 or comprising a polynucleotide sequence having at least 30% sequence identity with the polynucleotide sequence of any one of SEQ ID NOs: 2, 4, 5, 7, 8, 10, 12, 13, 15, 16, 18, 19, 21, 23, 24 or 26; or
   (b) a polynucleotide sequence which hybridises, preferably under at least low stringency conditions, with the complementary strand of any one SEQ ID NOs: 2, 4, 5, 7, 8, 10, 12, 13, 15, 16, 18, 19, 21, 23, 24 or 26.; or
   (c) a polynucleotide sequence which hybridises, preferably under at least low stringency conditions with the complementary strand of a polynucleotide having at least 30% sequence identity to any one of any one SEQ ID NOs: 2, 4, 5, 7, 8, 10, 12, 13, 15, 16, 18, 19, 21, 23, 24 or 26;
   (d) a polynucleotide sequence which is degenerate as a result of the degeneracy of the genetic code to a polynucleotide sequence as defined in any one of (a), (b) or (c); or
   (e) a polynucleotide sequence which is the complement of a nucleotide sequence as defined in (a), (b), (c) or (d).

25. A polynucleotide sequence according to embodiment 5, having a sequence identity of at least 60%, preferably at least 70%, more preferably at least 80%, most preferably at least 90%, most preferably at least 93%, most preferably at least about 95%, most preferably at least about 96%, most preferably at least about 97%, even most preferably at least about 98%, and even more preferred at least 99% to any one of any one SEQ ID NOs: 2, 4, 5, 7, 8, 10, 12, 13, 15, 16, 18, 19, 21, 23, 24 or 26.

26. A nucleic acid construct comprising the polynucleotide sequence of any one of embodiments 23 to 25.

27. A nucleic acid construct according to embodiment 26 which is an expression vector, wherein the polynucleotide sequence according to any one of embodiments 23 to 25 is operably linked to at least one control sequence for the expression of the polynucleotide sequence in a host cell.

28. A method of producing the polypeptide of embodiment 21 or 22, comprising:
   (a) cultivating a host cell according to embodiment 1 under conditions conducive to the production of the polypeptide by the host cell, and optionally,
   (b) recovering the polypeptide.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Example 1: Over-Expression of ERG20, BTS1 and tHMG in *S. Cerevisiae*

For over-expression of ERG20, BTS1 tHMG1, expression cassettes were designed to be integrated in one locus using technology described in WO2013/076280. To amplify the 5' and 3' integration flanks for the integration locus, suitable primers and genomic DNA from a CEN.PK yeast strain (van Dijken et al. Enzyme and Microbial Technology 26 (2000) 706-714) was used. The different genes were ordered as cassettes (containing homologous sequence, promoter, gene, terminator, homologous sequence) at DNA2.0. The genes in these cassettes were flanked by constitutive promoters and terminators. See Table 1. Plasmid DNA from DNA2.0 containing the ERG20, tHMG1 and BTS1 cassettes were dissolved to a concentration of 100 ng/μl. In a 50 μl PCR mix 20 ng template was used together with 20 pmol of the primers. The material was dissolved to a concentration of 0.5 μg/μl.

TABLE 1

| Composition of the over-expression constructs | | |
|---|---|---|
| Promoter | ORF | Terminator |
| Eno2 (SEQ ID NO: 30) | ERG20 (SEQ ID NO: 31) | Adh1 (SEQ ID NO: 32) |
| Fba1 (SEQ ID NO: 33) | tHMG1 (SEQ ID NO: 34) | Adh2 (SEQ ID NO: 35) |
| Tef1 (SEQ ID NO: 36) | BTS1 (SEQ ID NO: 37) | Gmp1 (SEQ ID NO: 38) |

For amplification of the selection marker, the pUG7-EcoRV construct (FIG. 1) and suitable primers were used. The KanMX fragment was purified from gel using the Zymoclean Gel DNA Recovery kit (ZymoResearch). Yeast strain Cen.PK113-3C was transformed with the fragments listed in Table 2.

TABLE 2

| DNA fragments used for transformation of ERG20, tHMG1 and BTS1 Fragment |
|---|
| 5'YPRcTau3 |
| ERG20 cassette |
| tHMG1 cassette |
| KanMX cassette |
| BTS1 cassette |
| 3'YPRcTau3 |

Figure 2:
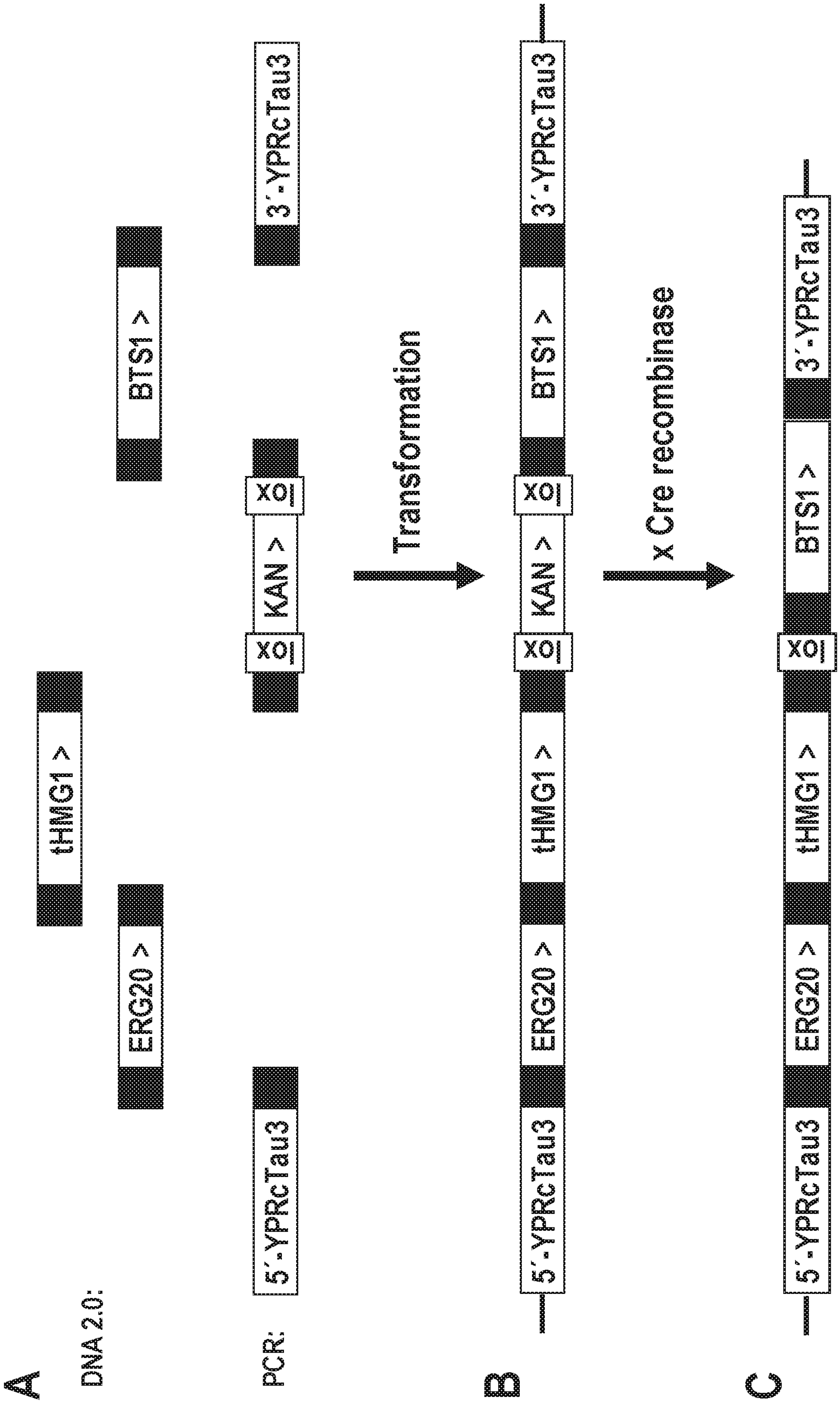
FIG. 2 sets out a schematic representation of the method by which the ERG20, tHMG1 and BTS1 over-expression cassettes are designed (A) and integrated (B) into the yeast genome. (C) shows the final situation after removal of the KANMX marker by the Cre recombinase.

After transformation and recovery for 2.5 hours in YEPhD (yeast extract phytone peptone glucose; BBL Phytone Peptone from BD) at 30° C. the cells were plated on YEPhD agar with 200 μg/ml G418 (Sigma). The plates were incubated at 30° C. for 4 days. Correct integration was established with diagnostic PCR and sequencing. Over-expression was confirmed with LC/MS on the proteins. The schematic of the assembly of ERG20, tHMG1 and BTS1 is illustrated in FIG. 2. This strain is named STV002.

Expression of CRE-recombinase in this strain led to out-recombination of the KanMX marker. Correct out-recombination, and presence of ERG20, tHMG and BTS1 was established with diagnostic PCR.

Example 2: Knock Down of Erg9

For reducing the expression of Erg9, an Erg9 knock down construct was designed and used that contains a modified 3' end, that continues into the TRP1 promoter driving TRP1 expression.

Figure 3:
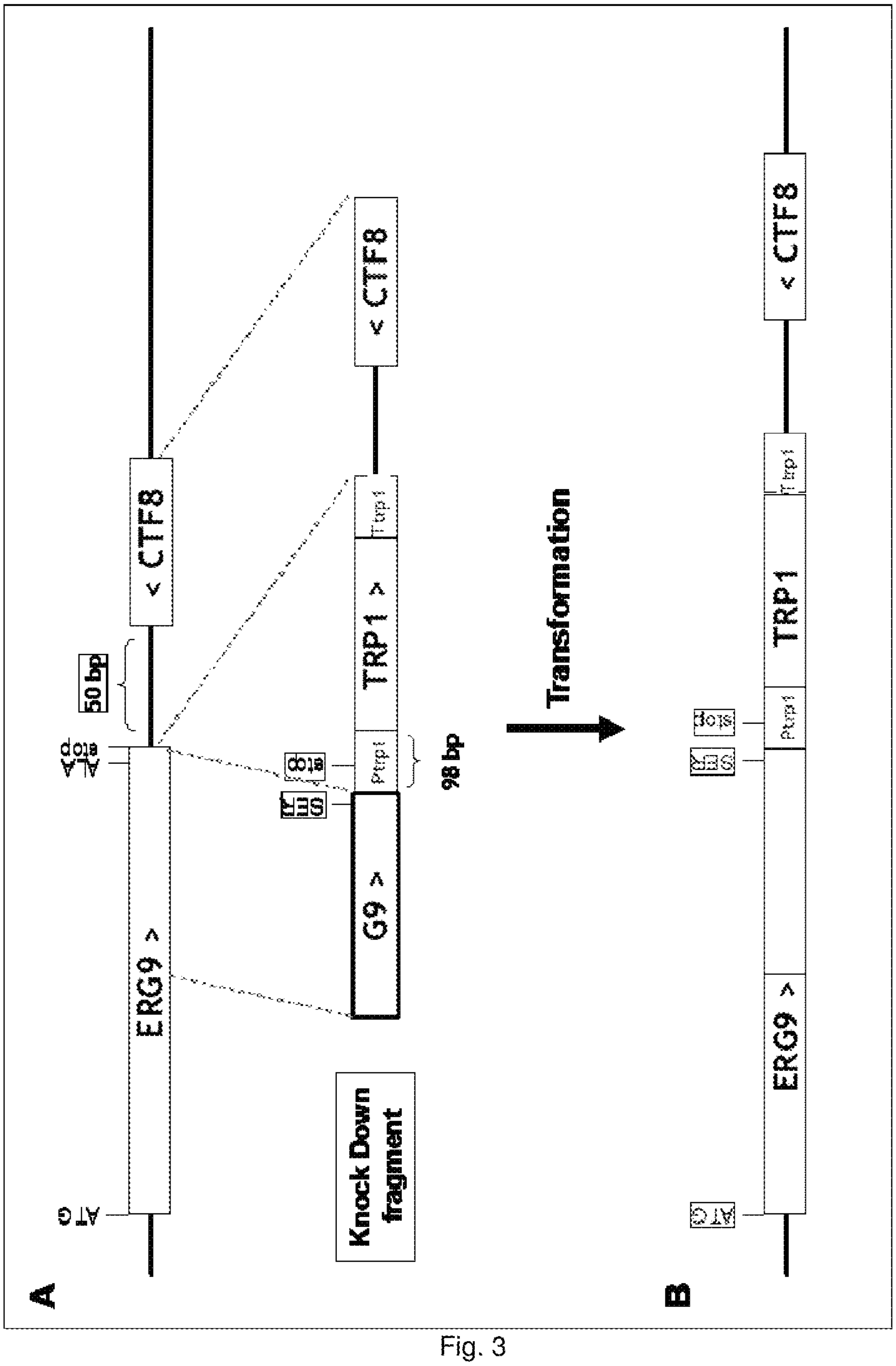
FIG. 3 sets out a schematic representation of the ERG9 knock down construct. This consists of a 500 bp long 3' part of ERG9, 98 bp of the TRP1 promoter, the TRP1 open reading frame and terminator, followed by a 400 bp long downstream sequence of ERG9. Due to introduction of a XbaI site at the end of the ERG9 open reading frame the last amino acid changes into Ser and the stop codon into Arg. A new stop codon is located in the TPR1 promoter, resulting in an extension of 18 amino acids.

The construct containing the Erg9-KD fragment was transformed to *E. coli* TOP10 cells. Transformants were grown in 2PY (2 times Phytone peptone Yeast extract), sAMP medium. Plasmid DNA was isolated with the QIAprep Spin Miniprep kit (Qiagen) and digested with SalI-HF (New England Biolabs). To concentrate, the DNA was precipitated with ethanol. The fragment was transformed to *S. cerevisiae*, and colonies were plated on mineral medium (Verduyn et al, 1992. Yeast 8:501-517) agar plates without tryptophan. Correct integration of the Erg9-KD construct was confirmed with diagnostic PCR and sequencing. The schematic of performed transformation of the Erg9-KD construct is illustrated in FIG. 3. The strain was named STV003.

Example 3: Over-Expression of UGT2_1a

For over-expression of UGT2_1a, technology was used as described in patent application nos. WO2013/076280 and WO2013/144257. The UGT2_1a was ordered as a cassette (containing homologous sequence, promoter, gene, terminator, homologous sequence) at DNA2.0. For details, see Table 3. To obtain the fragments containing the marker and Cre-recombinase, technology was used as described in patent application no. WO2013/135728. The NAT marker, conferring resistance to nourseothricin was used for selection.

TABLE 3

| Composition of the over-expression construct | | |
|---|---|---|
| Promoter | ORF | Terminator |
| Pgk1 (SEQ ID NO: 39) | UGT2_1a (SEQ ID NO: 28) | Adh2 (SEQ ID NO: 35) |

Suitable primers were used for amplification. To amplify the 5' and 3' integration flanks for the integration locus, suitable primers and genomic DNA from a CEN.PK yeast strain was used.

*S. cerevisiae* yeast strain STV003 was transformed with the fragments listed in Table 4, and the transformation mix was plated on YEPhD agar plates containing 50 μg/ml nourseothricin (Lexy NTC from Jena Bioscience).

TABLE 4

| DNA fragments used for transformation of UGT2_1a Fragment |
|---|
| 5'Chr09.01 |
| UGT2_1a cassette |
| NAT-CR |
| RE |
| 3'Chr09.01 |

Figure 4:
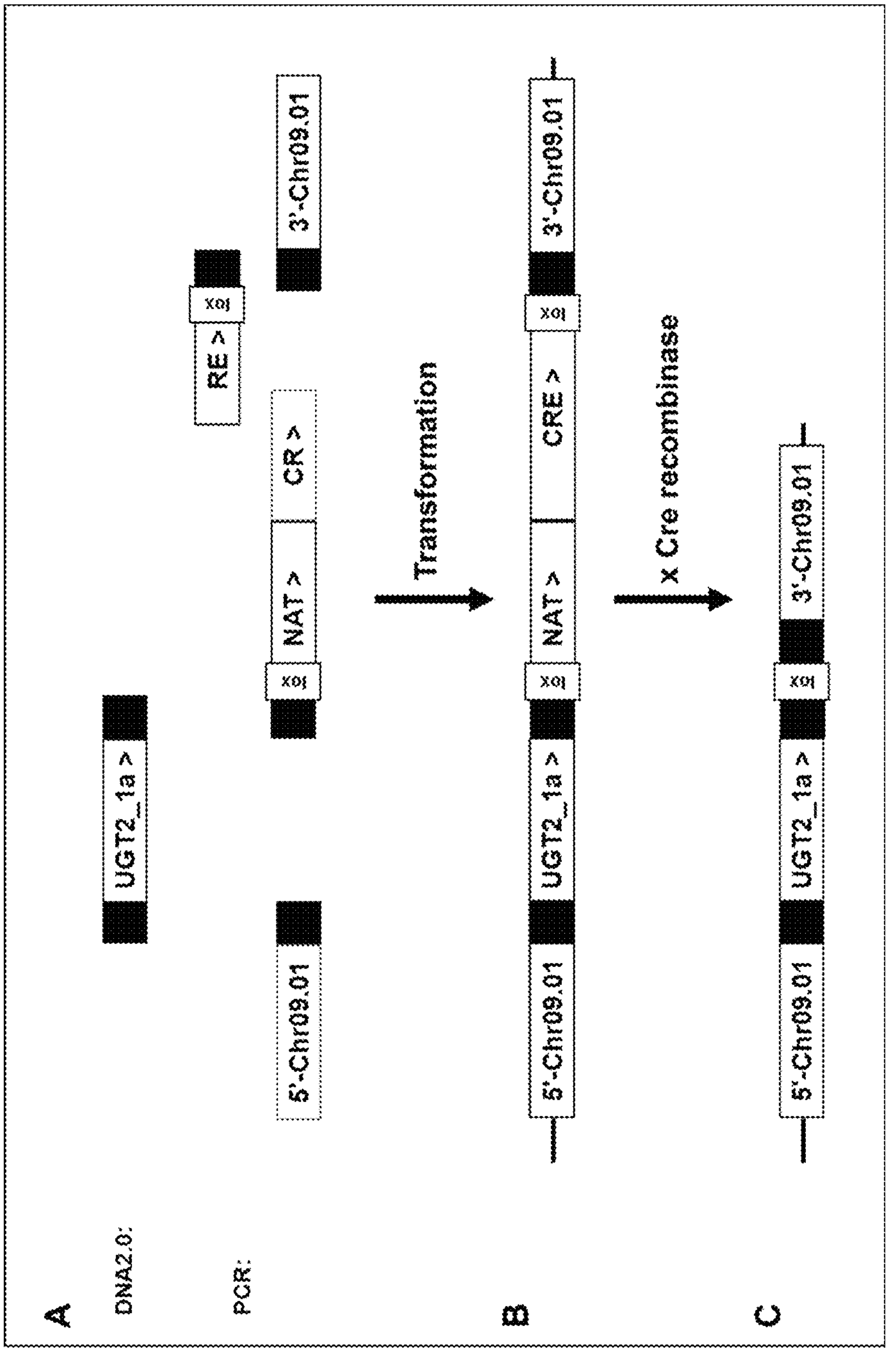
FIG. 4 sets out a schematic representation of how UGT2 is integrated into the genome. A. different fragments used in transformation; B. situation after integration; C. situation after expression of Cre recombinase).

Expression of the CRE recombinase is activated by the presence of galactose. To induce the expression of the CRE recombinase, transformants were restreaked on YEPh Galactose medium. This resulted in out-recombination of the marker(s) located between lox sites. Correct integration of the UGT2_1a and out-recombination of the NAT marker was confirmed with diagnostic PCR. The resulting strain was named STV004. The schematic of the performed transformation of the UGT2_1a construct is illustrated in FIG. 4.

Example 4: Over-Expression of Production Pathway to RebA: CPS, KS, KO, KAH, CPR, UGT1, UGT3 and UGT4

All pathway genes leading to the production of RebA were designed to be integrated in one locus using technology described in patent application nos. WO2013/076280 and WO2013/144257. To amplify the 5' and 3' integration flanks for the integration locus, suitable primers and genomic DNA from a CEN.PK yeast strain was used. The different genes were ordered as cassettes (containing homologous sequence, promoter, gene, terminator, homologous sequence) at DNA2.0 (see Table 5 for overview). The DNA from DNA2.0 was dissolved to 100 ng/μl. This stock solution was further diluted to 5 ng/μl, of which 1 μl was used in a 50 μl-PCR mixture. The reaction contained 25 pmol of each primer. After amplification, DNA was purified with the NucleoSpin 96 PCR Clean-up kit (Macherey-Nagel) or alternatively concentrated using ethanol precipitation.

TABLE 5

| Sequences used for production pathway to RebA | | | |
|---|---|---|---|
| Promoter | ORF | SEQ ID | Terminator |
| Kl prom 12.pro (SEQ ID NO: 40) | trCPS_SR | 41 | Sc ADH2.ter (SEQ ID NO: 35) |
| Sc PGK1.pro (SEQ ID NO: 39) | trKS_SR | 42 | Sc TAL1.ter (SEQ ID NO: 43) |
| Sc ENO2.pro (SEQ ID NO: 30) | KO_Gibfu | 44 | Sc TPI1.ter (SEQ ID NO: 45) |
| Ag lox_TEF1.pro (SEQ ID NO: 46) | KANMX | 47 | Ag TEF1_lox.ter (SEQ ID NO: 48) |
| Sc TEF1.pro (SEQ ID NO: 36) | KAH_4 | 49 | Sc GPM1.ter (SEQ ID NO: 38) |
| Kl prom 6.pro (SEQ ID NO: 50) | CPR_3 | 51 | Sc PDC1.ter (SEQ ID NO: 52) |
| Kl prom 3.pro (SEQ ID NO: 53) | UGT1_SR | 54 | Sc TDH1.ter (SEQ ID NO: 55) |
| Kl prom 2.pro (SEQ ID NO: 56) | UGT3_SR | 57 | Sc ADH1.ter (SEQ ID NO: 32) |
| Sc FBA1.pro (SEQ ID NO: 33) | UGT4_SR | 58 | Sc ENO1.ter (SEQ ID NO: 59) |

All fragments for the pathway to RebA, the marker and the flanks (see overview in Table 6) were transformed to *S. cerevisiae* yeast strain STV004. After overnight recovery in YEPhD at 20° C. the transformation mixes were plated on YEPhD agar containing 200 μg/ml G418. These were incubated 3 days at 25° C. and one night at RT.

TABLE 6

| DNA fragments used for transformation of CPS, KS, KO, KanMX, KAH, CPR, UGT1, UGT3 and UGT4<br>Fragment |
|---|
| 5'INT1 |
| CPS cassette |
| KS cassette |
| KO cassette |
| KanMX cassette |
| KAH cassette |
| CPR cassette |
| UGT1 cassette |
| UGT3 cassette |
| UGT4 cassette |
| 3'INT1 |

Figure 5:
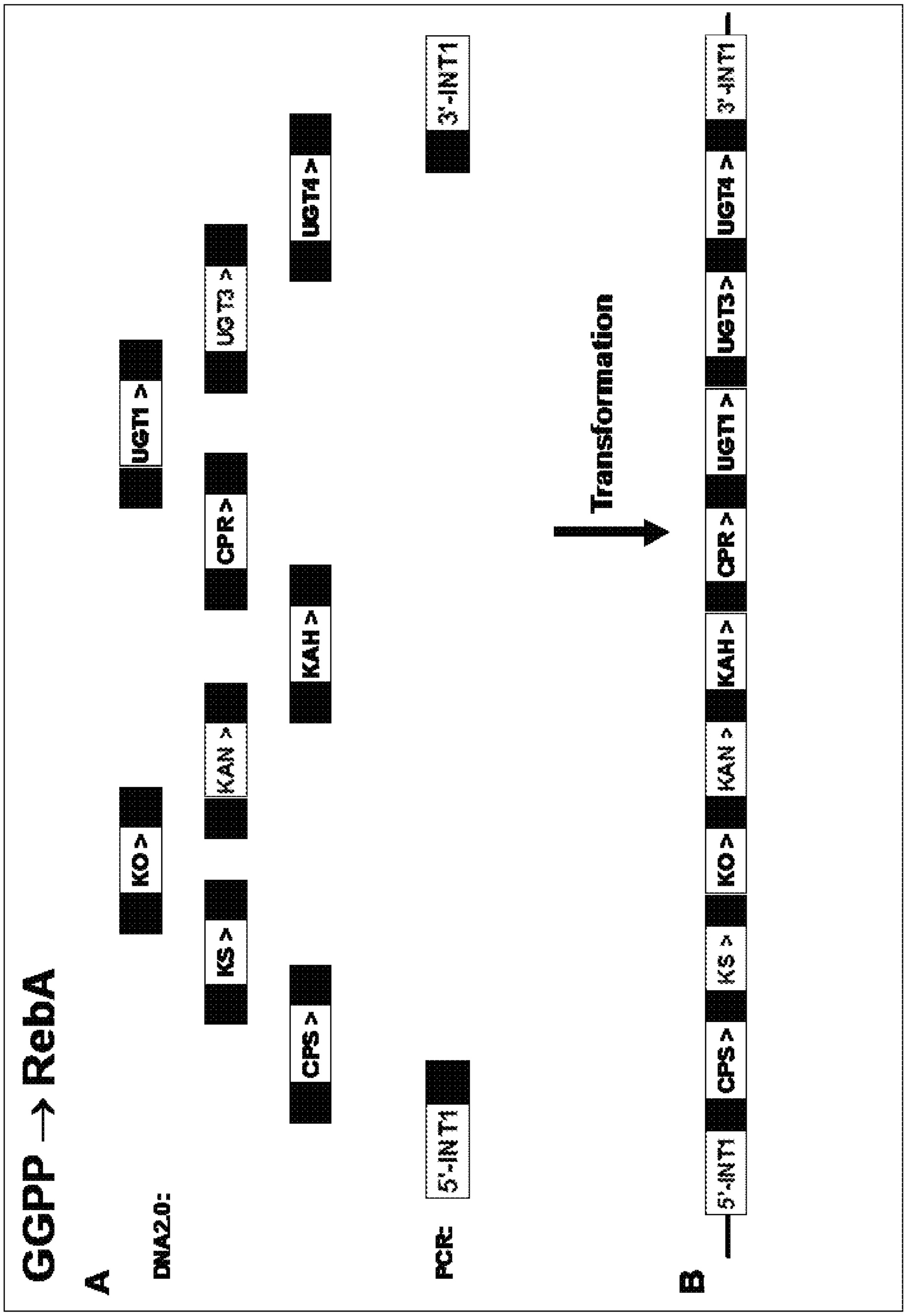
FIG. 5 sets out a schematic representation of how the pathway from GGPP to Steviol is integrated into the genome. A. different fragments used in transformation; B. situation after integration.

Correct integration was confirmed with diagnostic PCR and sequence analysis (3500 Genetic Analyzer, Applied Biosystems). The sequence reactions were done with the BigDye Terminator v3.1 Cycle Sequencing kit (Life Technologies). Each reaction (10 μl) contained 50 ng template and 3.2 pmol primer. The products were purified by ethanol/EDTA precipitation, dissolved in 10 μl HiDi formamide and applied onto the apparatus. The strain was named STV006. The schematic of how the pathway from GGPP to RebA is integrated into the genome is illustrated in FIG. 5. Table 7 sets out the strains used in Examples 1 to 5.

TABLE 7

| Table of strains | | |
|---|---|---|
| Strain | Background | Genotype |
| Cen.PK113-3C | — | MATa URA3 HIS3 LEU2 trp1-289 MAL2-8C SUC2 |
| STV002 | Cen.PK113-3C | MATa URA3 HIS3 LEU2 trp1-289 MAL2-8C SUC2 YPRcTau3::ERG20, tHMG1, KanMX, BTS1 |

TABLE 7-continued

| Table of strains | | |
|---|---|---|
| Strain | Background | Genotype |
| STV003 | STV002 | MATa URA3 HIS3 LEU2 trp1-289 MAL2-8C SUC2 YPRcTau3::ERG20, tHMG1, KanMX, BTS1 ERG9::ERG9-KD TRP1 |
| STV004 | STV003 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a |
| STV006 | STV004 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a INT1::CPS, KS, KO, KanMX, KAH, CPR, UGT1, UGT3, UGT4 |

Example 5: Removal of the KanMX Selection Marker of STV006

Figure 6:
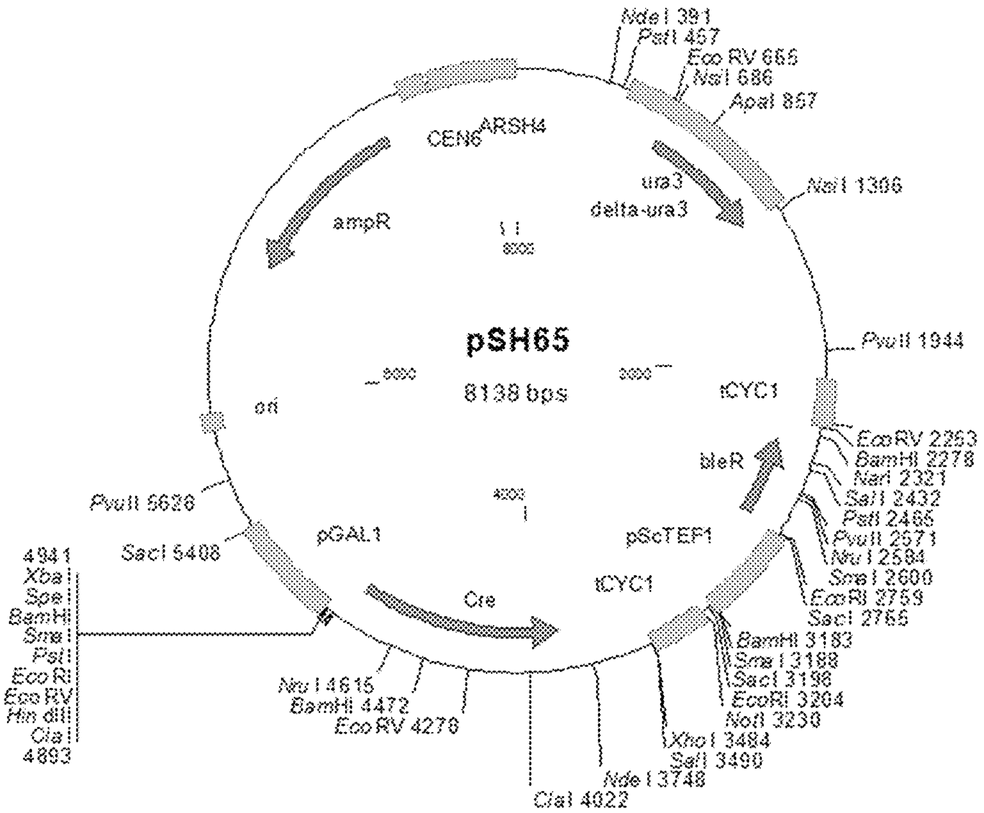
FIG. 6 sets out the pSH65 plasmid, carrying the CRE gene, which is used for removal of the antibiotic marker.

To remove the KanMX marker present in the strain, the plasmid pSH65, containing CRE recombinase (FIG. 6), was transformed to STV006. Transformants were first selected on YEPD containing 20 μg/ml Phleomycin (Invitrogen) and then restreaked on YEP Galactose medium to induce CRE recombinase expression. Correct out-recombination of the marker was established by diagnostic PCR. RebA production of this marker-free strain was confirmed in a production experiment. The marker free version of STV006 was called STV008.

Example 6: Removal of UGT2_1a in STV008 by the NAT Selection Marker

Figure 7:
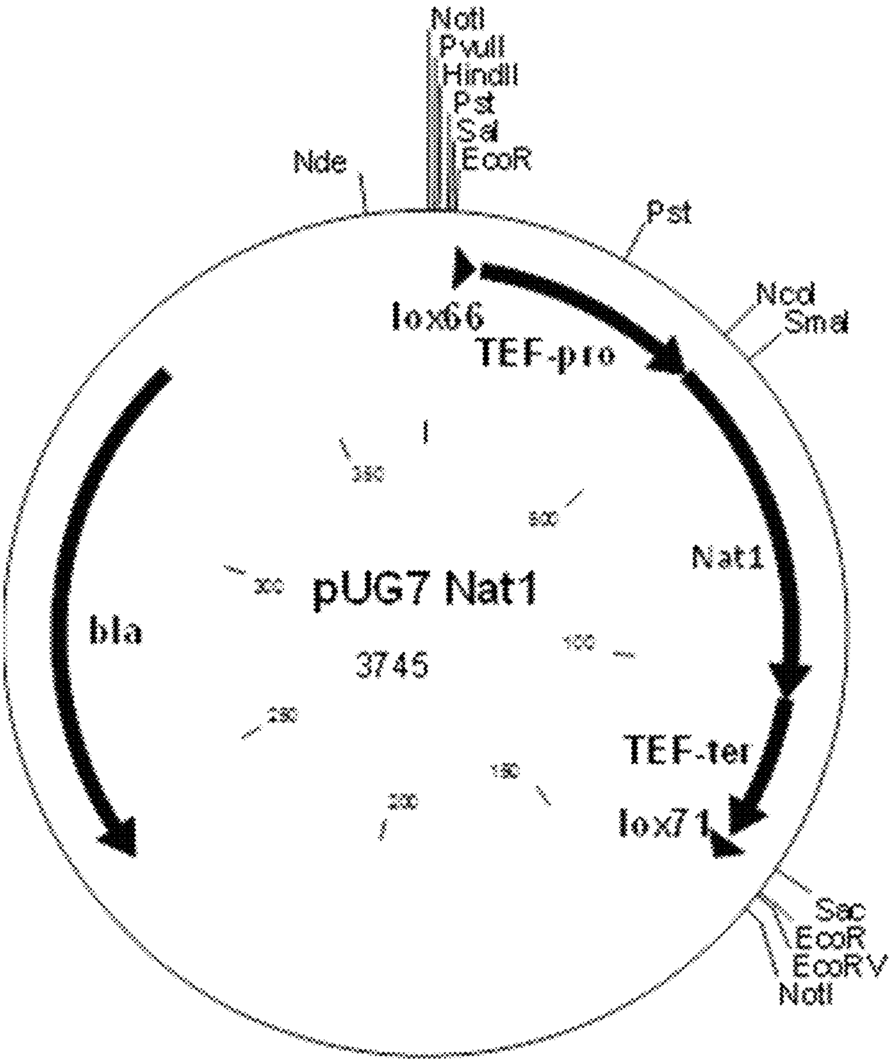
FIG. 7 sets out the map of plasmid pUG7-NAT.
Figure 8:
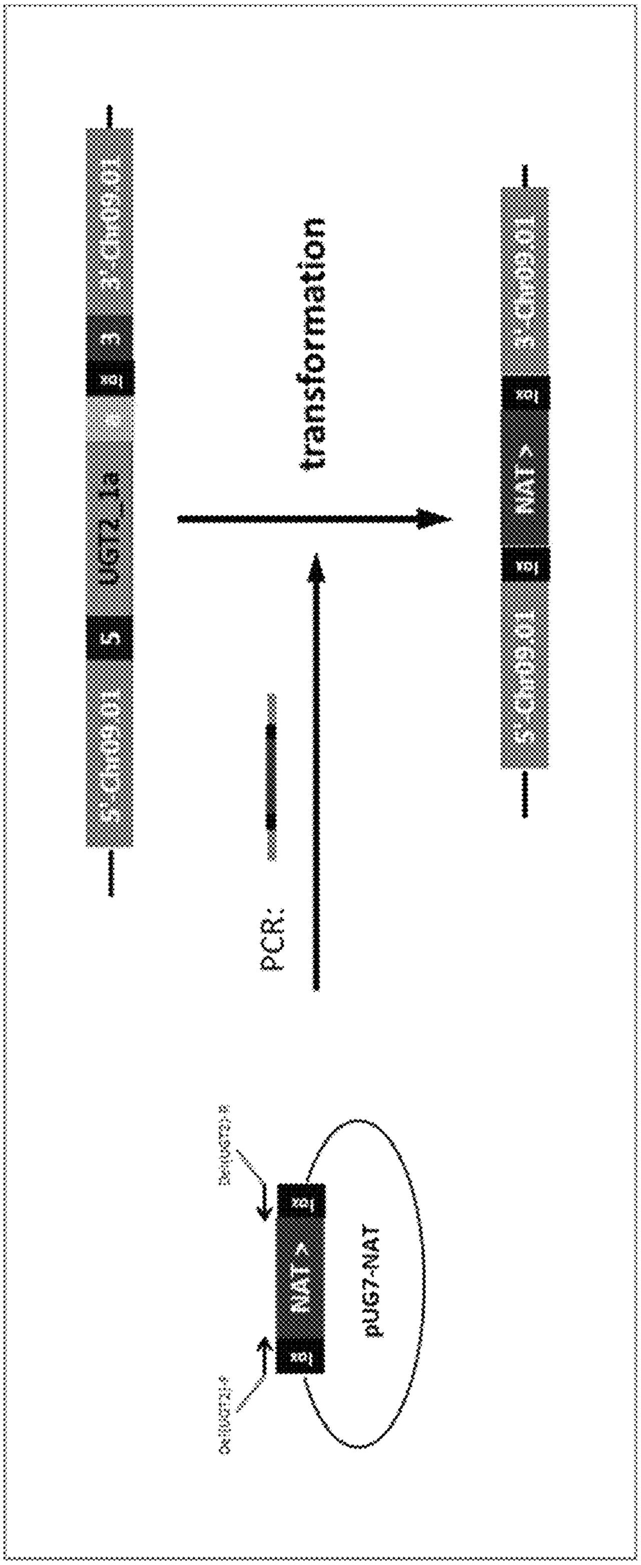
FIG. 8 sets out the replacement of UGT2_1a from STV008 with the Nat selection marker.

To remove the UGT2_1a, located at the Chr09.01 locus of STV008, the nourseothricin selection (NAT) marker and surrounding lox sites were amplified from the plasmid pUG7-NAT (FIG. 7) with primers containing additional 50 nt sequences homologous to the Chr09.01 integration flanks (FIG. 8). The PCR product was purified with the NucleoSpin Gel and PCR Clean-up kit (Macherey-Nagel) and transformed to STV008. Transformants were selected on YEPD containing 50 μg/ml nourseothricin (Lexy NTC from Jena Bioscience). Correct integration of the NAT marker and absence of UGT2_1a was confirmed by diagnostic PCR. This new strain was named STV009.

Example 7: Removal of the Nat Selection Marker of STV009

Figure 9:
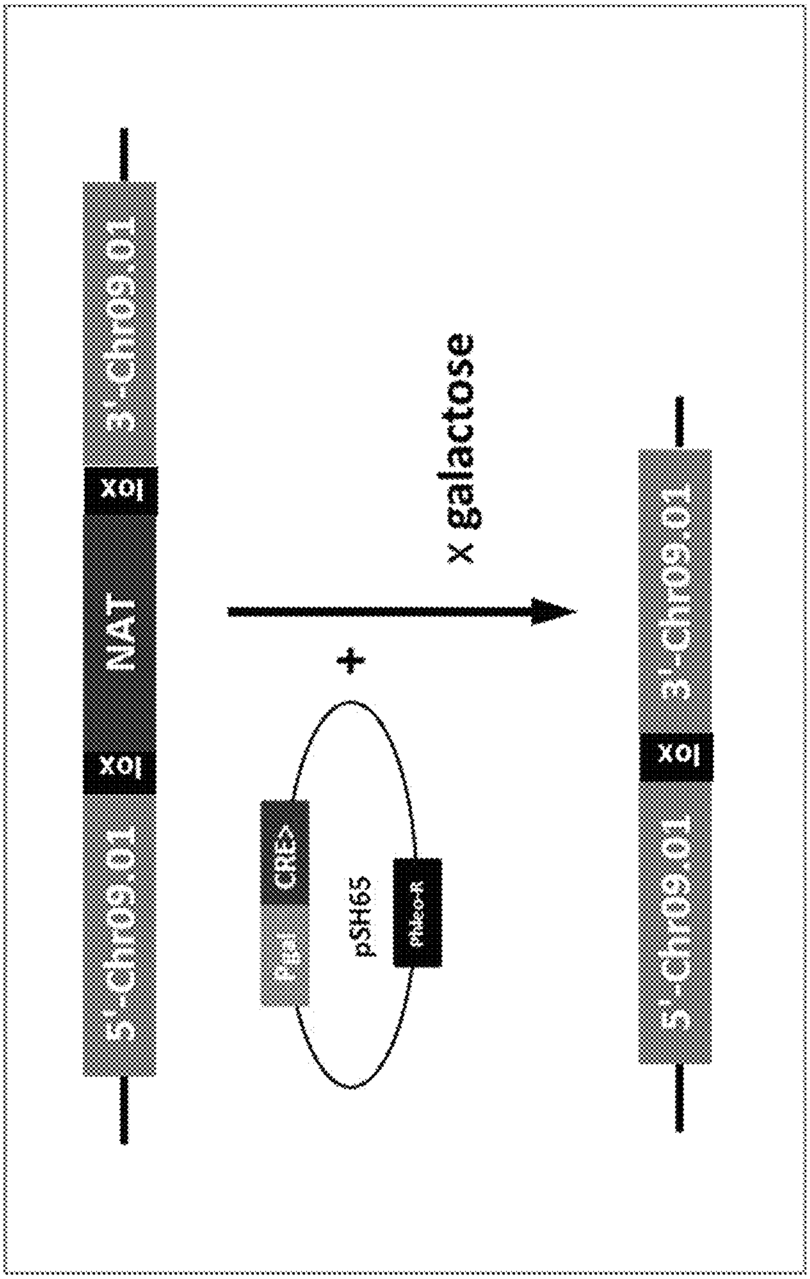
FIG. 9 sets out the removal of the NAT marker from STV008.

To be able to use the same integration locus for testing the UGT2 variants the NAT marker had to be removed from strain STV009 (FIG. 9). Therefore the CRE recombinase, located on the plasmid pSH65, was transformed to STV009 and transformants selected on YEPD containing 20 μg/ml Phleomycin. Colonies were restreaked on YEP Galactose agar plates. The plates were incubated at 30° C. Removal of the NAT marker by CRE recombinase was demonstrated by diagnostic PCR. In a production experiment it was shown that the STV009ΔNAT strain accumulates the same amount of rubusoside as its parent, STV009. The new strain was called STV053.

Example 8: Integration of UGT2 Gene Variants at the Chr09.01 Locus

Figure 10:
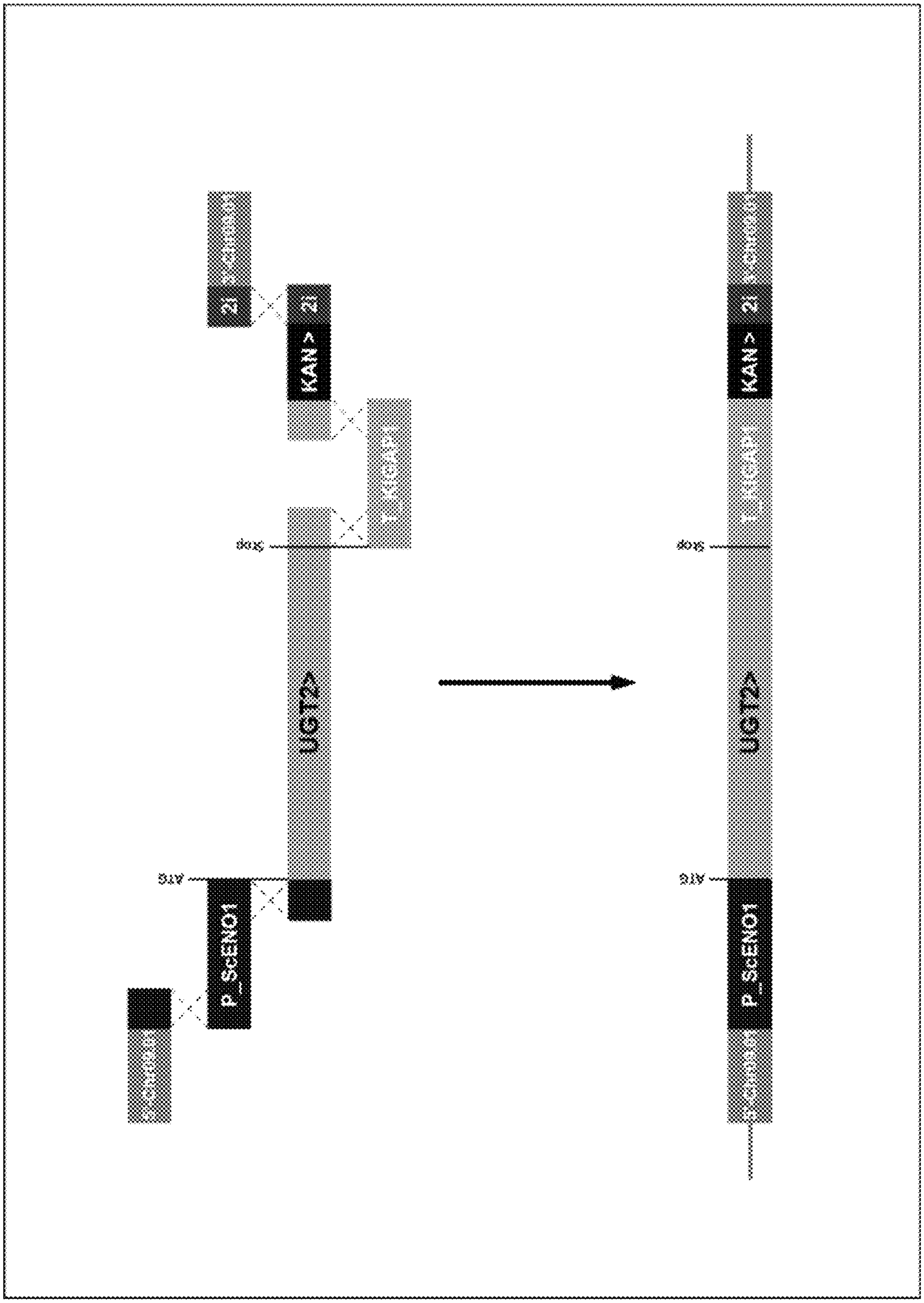
FIG. 10 sets out the integration of UGT2 genes at the Chr09.01 locus.

Different gene variants encoding UGT2 activity (SEQ ID NOs: 4, 7, 10, 12, 15, 18, 21, 23 and 28) were each separately integrated into the Chr09.01 locus by using several separate DNA fragments, containing 50 bp flanking homology segments for recombination (FIG. 10).

The 5'- and 3'-Chr09.01 integration flanks were amplified with suitable primers from genomic DNA from a CEN.PK yeast strain (van Dijken et al. Enzyme and Microbial Technology 26 (2000) 706-714). For the 5'-flank the reverse primer contained an extended 50 bp sequence homologous to promoter sequence to be used, namely the ScENO1 promoter (SEQ ID NO: 60). The forward primer for the 3'-flank contained a 50 bp linker extension.

The KanMX selection marker was amplified from the pUG7-EcoRV construct. The forward primer contained an additional 50 bp sequence homologous to the KlGAP1 (SEQ ID NO: 61) terminator. The reverse primer also possessed a 50 bp linker extension.

The different UGT2 gene variants were ordered at SGI-DNA. Their open reading frame was upstream flanked by 50 bp of the pScENO1 promoter (SEQ ID NO: 60) and downstream by 50 bp of the Klgap1T terminator (SEQ ID NO: 61). The genes were amplified from the SGI-DNA constructs by using primers annealing to these promoter and terminator sequences.

The PCR products were purified using the NucleoSpin 96 PCR Clean-up kit (Macherey-Nagel). Equimolar amounts of 5'-Chr09.01 flank, ENO1 promoter, UGT2 gene, KlGAP1 terminator, KanMX selection marker and 3'-Chr09.01 flank were combined for each UGT2 variant to be tested. One additional mixture was made containing the UGT2_1a. These mixtures were transformed to STV053 and plated on YEPD containing 200 µg/ml G418.

For each UGT2 variant, several replicate transformants were tested in a production experiment.

Example 9: Production of Rebaudioside A with *S. Cerevisiae*

A pre-culture was inoculated with colony material from YEPD agar. The pre-culture was grown in 200 µl mineral medium with glucose as carbon source. The pre-culture was incubated 72 hours in an Infors incubator at 27° C., 750 rpm and 80% humidity.

40 µl of pre-culture was used to inoculate 2.5 ml mineral medium with glucose as carbon source. The main cultures were incubated 120 hours in an Infors incubator at 27° C., 550 rpm, 80% humidity. The cultures were well homogenized by pipetting up and down and 1 ml of culture was transferred to a 96-well plate. The 96-well plate was incubated for 15 minutes at 95° C. in a waterbath and cooled down to room temperature. To each well 0.5 ml of acetonitril was added and homogenized by pipetting up and down. The cell debris was pelleted by centrifugation at 3000×g for 10 minutes. The supernatant was diluted 200 times in 33% acetonitril.

Figure 11:
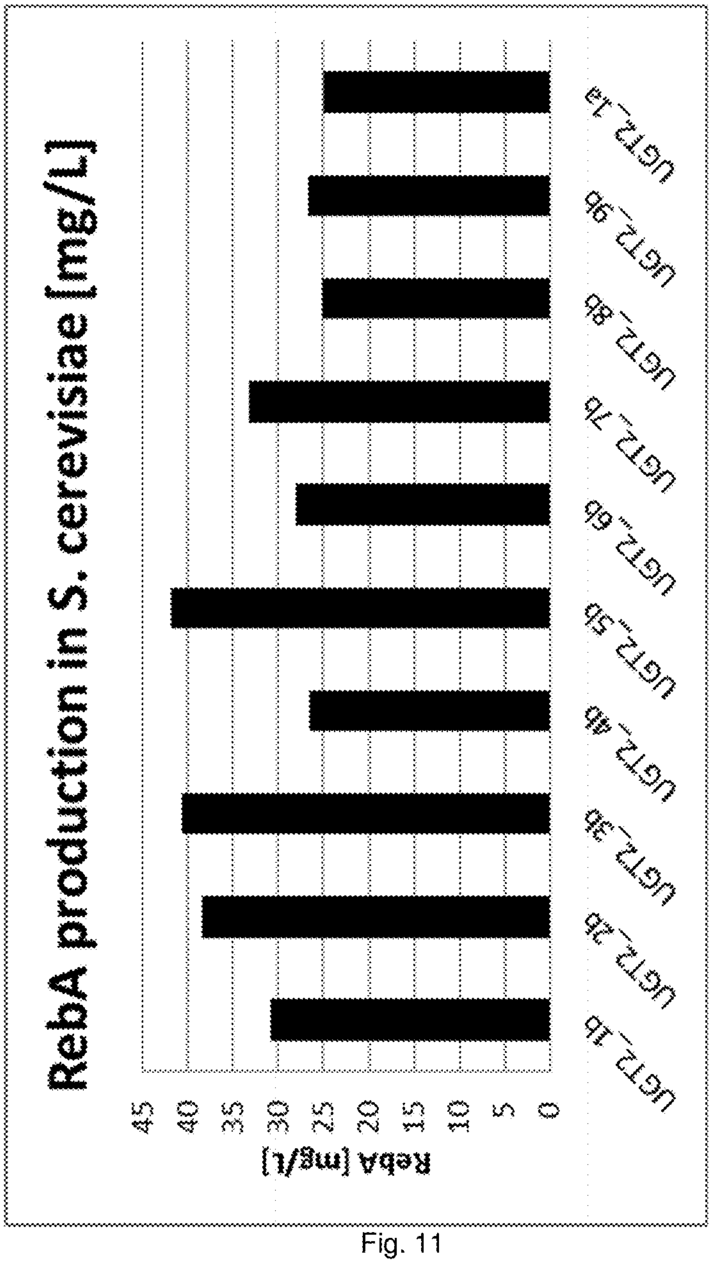
FIG. 11 sets out the production of rebaudioside A in *Saccharomyces* strains carrying different variants of UGT2

Samples were analyzed for RebA using LC/MS. RebA (RV0141-94, DAE Pyung Co. Ltd) was used as standard. We found that the strains that had the particular UGT2 gene variants as described, produced higher titers of RebA compared to the strain containing the UGT2_1a as set out in Table 8 and FIG. 11.

TABLE 8

Rebaudioside A production in *Saccharomyces* strains expressing UGT2 variant enzymes

| UGT2 variant | RebA (mg/L) |
|---|---|
| UGT2_1b | 30.8 |
| UGT2_2b | 38.4 |
| UGT2_3b | 40.6 |
| UGT2_4b | 26.5 |
| UGT2_5b | 41.8 |
| UGT2_6b | 28.1 |
| UGT2_7b | 33.3 |
| UGT2_8b | 25.2 |
| UGT2_9b | 26.7 |
| UGT2_1a | 25.0 |

Example 10: Production of Rebaudioside M with *S. Cerevisiae*

A pre-culture was inoculated with colony material from YEPD agar. The pre-culture was grown in 200 µl mineral medium with glucose as carbon source. The pre-culture was incubated 72 hours in an Infors incubator at 27° C., 750 rpm and 80% humidity.

40 µl of pre-culture was used to inoculate 2.5 ml mineral medium with glucose as carbon source. The main cultures were incubated 120 hours in an Infors incubator at 27° C., 550 rpm, 80% humidity. The cultures were well homogenized by pipetting up and down and 1 ml of culture was transferred to a 96-well plate. The 96-well plate was incubated for 15 minutes at 95° C. in a waterbath and cooled down to room temperature. To each well 0.5 ml of acetonitril was added and homogenized by pipetting up and down. The cell debris was pelleted by centrifugation at 3000×g for 10 minutes. The supernatant was diluted 200 times in 33% acetonitril.

The presence of RebM was confirmed by LC and MS analyzed with a LTQ orbitrap (Thermo), equipped with a Acella LC and a Waters Acquity UPLC BEH amide 1.7 µm 2.1*150 mm column. Eluentia used for the separation were A: 10 mM Ammonium acetate in MilliQ water, B: Acetonitrile, and the gradient started at 65% A and was kept here for 1.5 minutes, then increased to 95% B in 0.5 minutes and kept here for 0.5 minutes before regeneration for 1.5 min at 65% A. The flow-rate was 0.6 ml/min and the column temperature was kept at 50 C. Mass spectral analysis was performed in electrospray negative ionization mode, scanning from m/z 100-1800 at a resolution of 7500. Reb M elutes at tr=0.72 min, just after reb D at tr=0.63. Reb M is characterized by a deprotonated molecule of m/z 1289.5286. The elemental composition could be estimated using accurate mass analysis.

Figure 12:
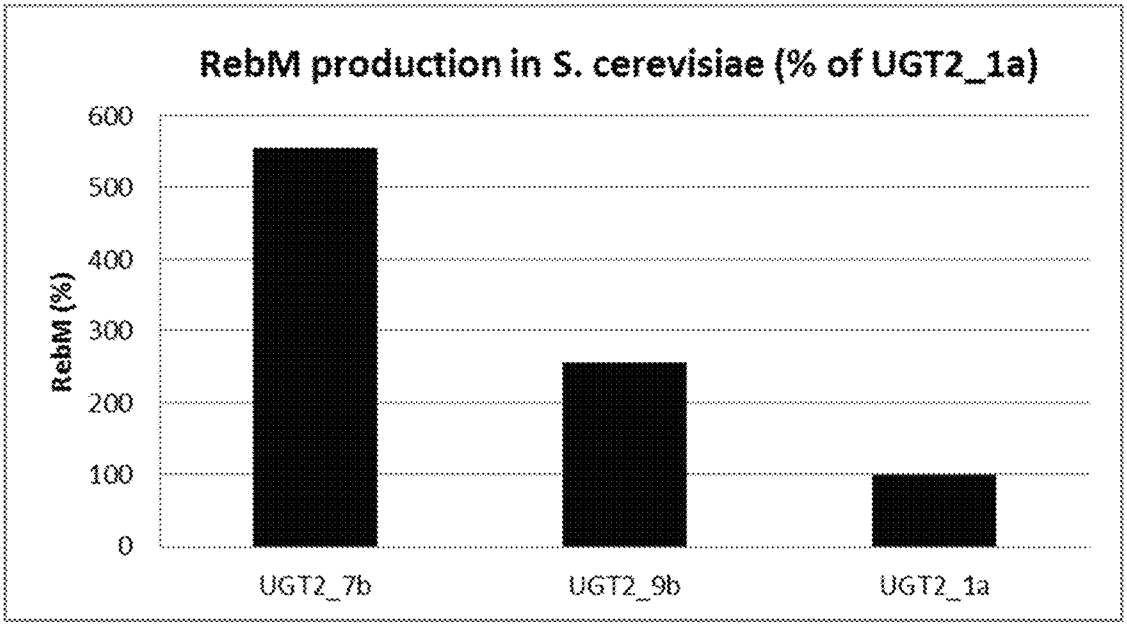

We found that the strains that had the particular UGT2 gene variants as described, produced higher titers of RebM compared to the strain containing the UGT2_1a as set out in FIG. 12 and Table 9.

TABLE 9

Rebaudioside M production in *Saccharomyces* strains expressing UGT2 variant enzymes, compared in percentages to UGT2_1a.

| UGT2 variant | RebM (relative to UGT2_1a) |
|---|---|
| UGT2_7b | 555 |
| UGT2_9b | 256 |
| UGT2_1a | 100 |

Example 11: Description of Steviol Glycoside Production Strain ML14094 (MAT-A Lineage)

Two *Yarrowia lipolytica* strains of mating types MATA and MATB were engineered for steviol glycoside production. These strains were mated, the diploid sporulated, and spores with steviol glycoside production were selected. One of these spores was further developed for the production of steviol glycosides, including the production of rebaudioside A.

Step 1: Strain ML10371 (MAT-A, lys1-, ura3-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

Figure 13:
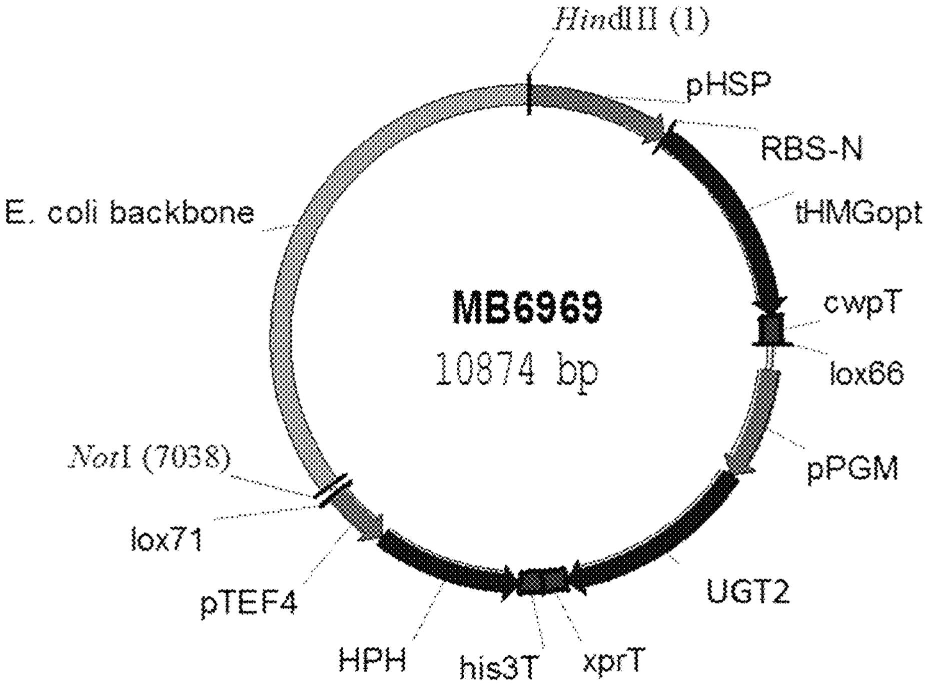

1) a 7.0 kb DNA fragment isolated by gel purification following HindIII/NotI digestion of plasmid MB6969 (FIG. 13). This construct encodes a synthetic construct for the overexpression of UGT2_1a (SEQ ID NO: 29) linked to the pPGM promoter (SEQ ID NO: 62) and xprT terminator (SEQ ID NO: 69) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 75) linked to the pHSP promoter (SEQ ID NO: 63) and cwpT terminator (SEQ ID NO: 70).

Figure 14:
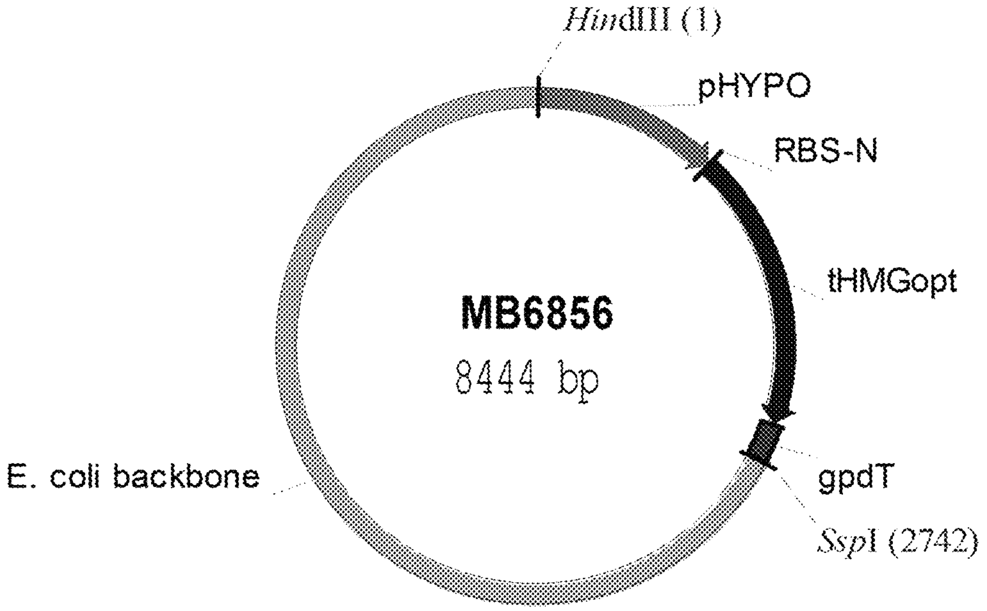
FIG. 14 sets out the map of plasmid MB6856, carrying gene tHMG

2) a 2.7 kb DNA fragment isolated by gel purification following HindIII/SspI digestion of MB6856 (FIG. 14). This construct encodes tHMGopt (SEQ ID NO: 75) linked to the pHYPO promoter (SEQ ID NO: 64) and gpdT terminator (SEQ ID NO: 71).

Figure 15:
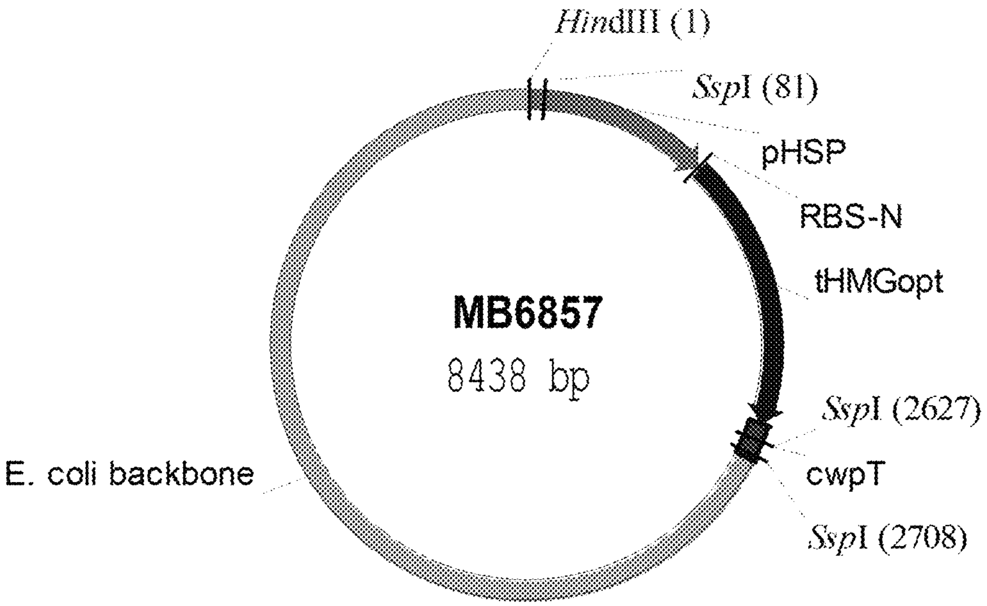
FIG. 15 sets out the map of plasmid MB6857, carrying gene tHMG

3) a 2.5 kb DNA fragment isolated by gel purification following SspI digestion of MB6857 (FIG. 15). This construct encodes tHMGopt (SEQ ID NO: 75) linked to the pHSP promoter (SEQ ID NO: 63) and cwpT terminator (SEQ ID NO: 70).

Figure 16:
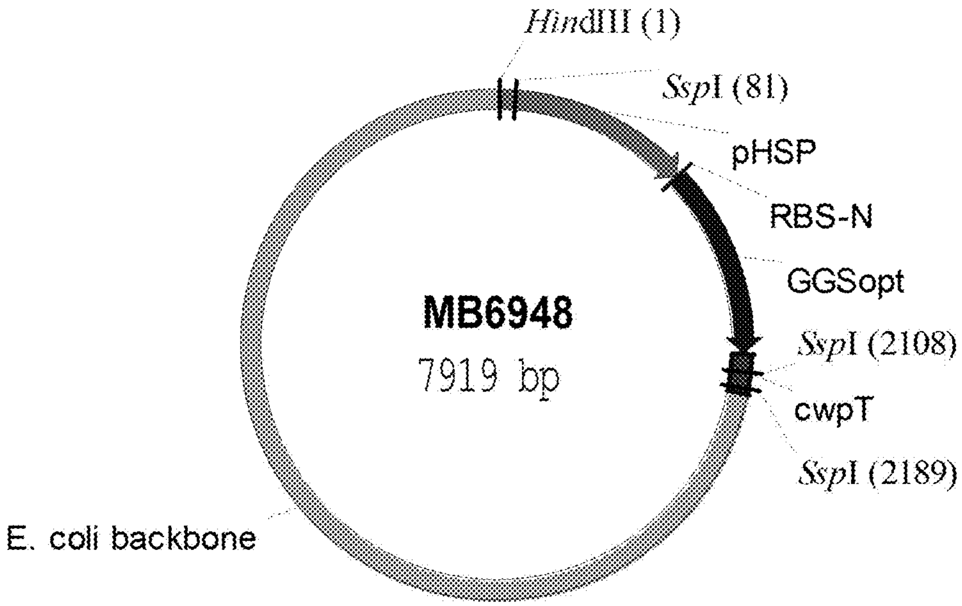
FIG. 16 sets out the map of plasmid MB6948, carrying gene GGS

4) a 2.0 kb DNA fragment isolated by gel purification following SspI digestion of MB6948 (FIG. 16). This construct encodes a synthetic construct for the overexpression of the codon optimized *Y. lipolytica* geranyl-geranyl-pyrophosphate synthetase (GGSopt: SEQ ID NO: 76) linked to the pHSP promoter (SEQ ID NO: 63) and cwpT terminator (SEQ ID NO: 70).

Figure 17:
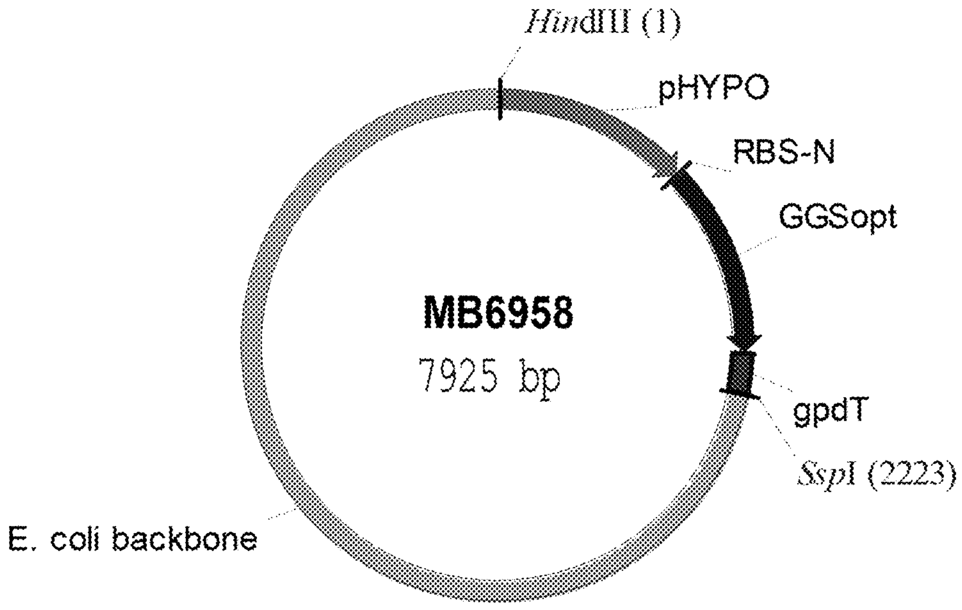
FIG. 17 sets out the map of plasmid MB6958, carrying gene GGS

5) a 2.2 kb DNA fragment isolated by gel purification following HindIII/SspI digestion of MB6958 (FIG. 17). This construct encodes GGSopt (SEQ ID NO: 76) linked to the pHYPO promoter (SEQ ID NO: 64) and gpdT terminator (SEQ ID NO: 71). The resulting strain was denoted ML13462.

Figure 18:
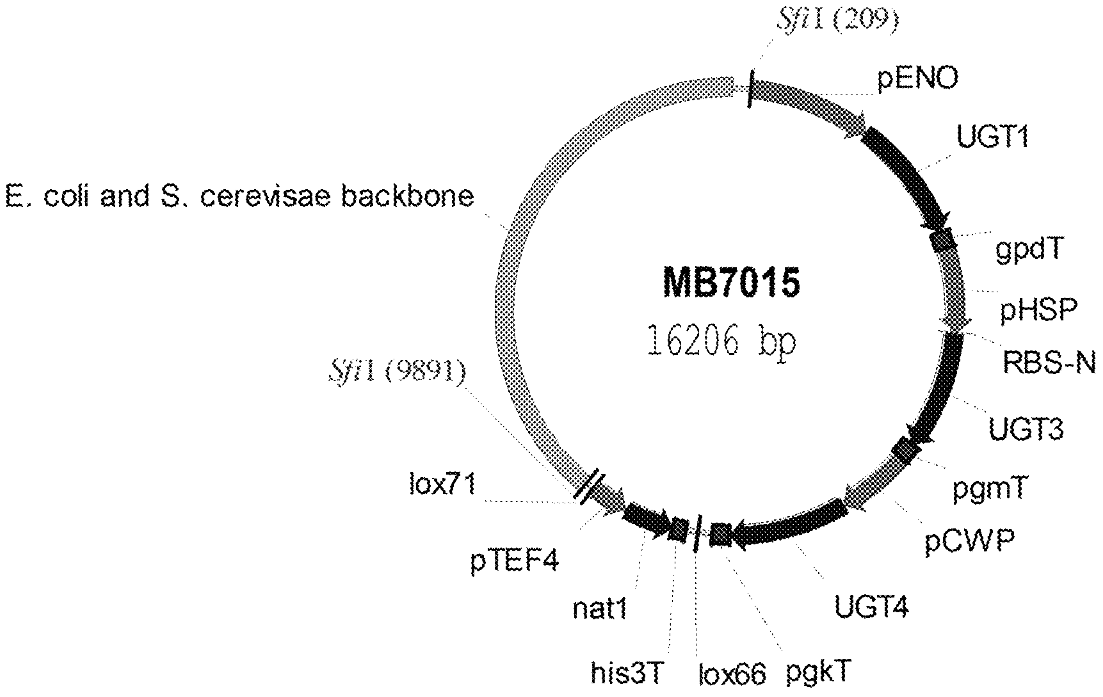
FIG. 18 sets out the map of plasmid MB7015, carrying genes UGT1, UGT3 and UGT4

Step 2. Strain ML13462 was transformed with a 9.7 kb fragment isolated by gel purification following SfiI digestion of plasmid MB7015 (FIG. 18). This construct encodes a synthetic construct for the overexpression of UGT1 (SEQ ID NO: 77) linked to the pENO (SEQ ID NO: 65) promoter and gpdT terminator (SEQ ID NO: 71), UGT3 (SEQ ID NO: 78) linked to the pHSP promoter (SEQ ID NO: 63) and pgmT terminator (SEQ ID NO: 72), UGT4 (SEQ ID NO: 79) linked to the pCWP (SEQ NO: 66) promoter and pgkT terminator (SEQ ID NO: 73), and the lox-flanked nourseothricin resistance marker (NAT). Note that placement of lox sites allows for subsequent removal of nourseothricin resistance via CRE recombinase mediated recombination. A nourseothricin resistant isolate was denoted ML13500.

Figure 19:
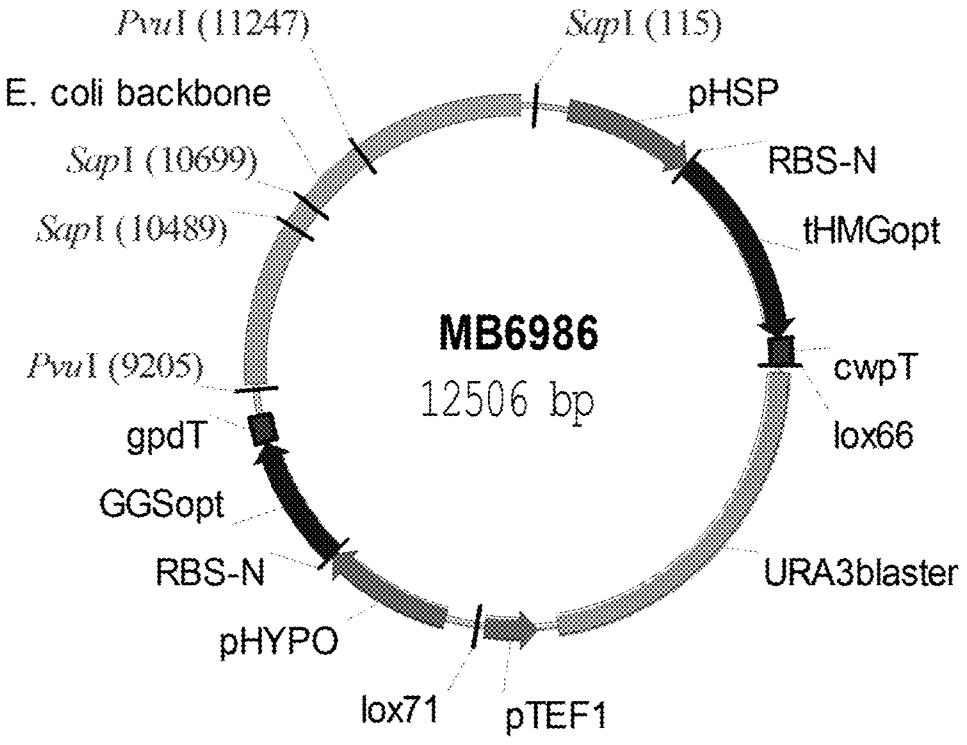
FIG. 19 sets out the map of plasmid MB6986, carrying genes tHMG and GGS

Step 3. Strain ML13500 was transformed with a 9.1 kb fragment isolated by gel purification following PvuI/SapI digestion of plasmid MB6986 (FIG. 19). This construct encodes tHMGopt (SEQ ID NO: 75) linked to the pHSP promoter (SEQ ID NO: 63) and cwpT terminator (SEQ ID NO: 70), the lox-flanked URA3blaster prototrophic marker, and GGSopt (SEQ ID NO: 76) linked to the pHYPO promoter (SEQ ID NO: 64) and gpdT terminator (SEQ ID NO: 71). Transformants were selected on minimal medium lacking uracil. One selected uracil prototroph was denoted ML13723.

Figure 20:
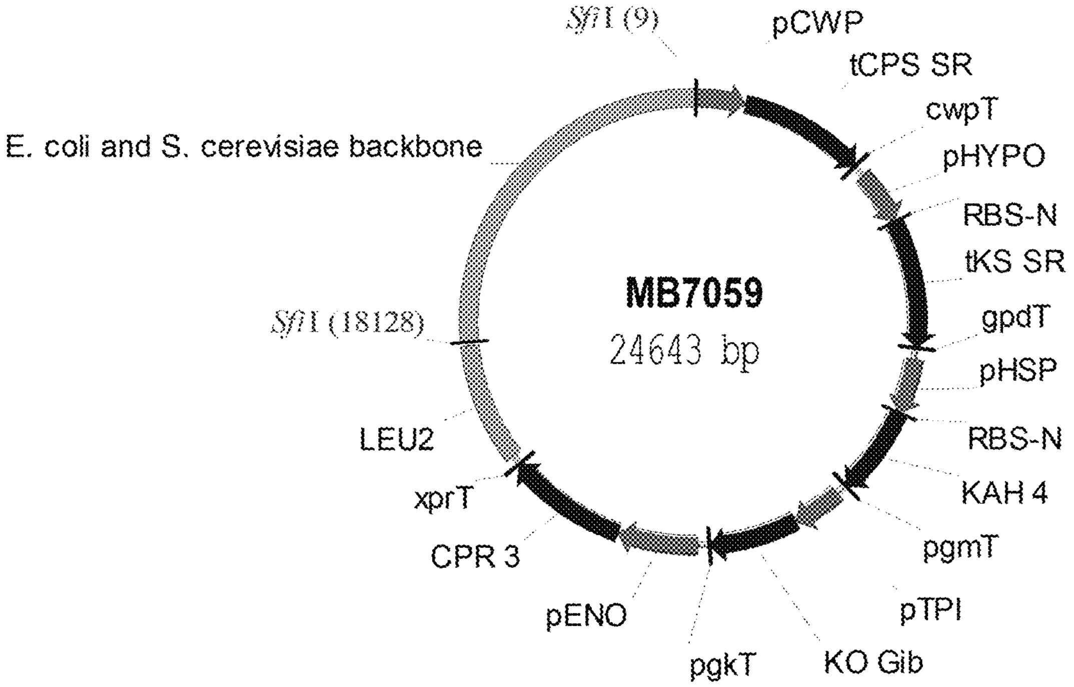
FIG. 20 sets out the map of plasmid MB7059, carrying genes tCPS_SR, tKS_SR, KAH_4, KO_Gib and CPR_3.

Step 4. Strain ML13723 was transformed with an 18.1 kb fragment isolated by gel purification following SfiI digestion of plasmid MB7059 (FIG. 20). MB7059 encodes the tCPS_SR (SEQ ID NO: 80) linked to pCWP promoter (SEQ ID NO: 66) and cwpT terminator (SEQ ID NO: 70), the tKS_SR (SEQ ID NO: 81) linked to the pHYPO promoter (SEQ ID NO: 64) and gpdT terminator (SEQ ID NO: 71), the KAH_4 (SEQ ID NO: 92) linked to the pHSP promoter (SEQ ID NO: 63) and pgmT terminator (SEQ ID NO: 72), the KO_Gib (SEQ ID NO: 83) linked to the pTPI promoter (SEQ ID NO: 67) and pgkT terminator (SEQ ID NO: 73), the CPR_3 (SEQ ID NO: 84) linked to the pENO promoter (SEQ ID NO: 65) and xprT terminator (SEQ ID NO: 69) and the native *Y. lipolytica* LEU2 locus. One selected rebaudioside A-producing transformant was denoted ML14032.

Step 5. Strain ML14032 was struck to YPD and grown overnight and then struck to 5-FOA plates to allow for recombination mediated loss of the URA3 marker introduced in Step 3. One selected 5-FOA resistant transformant was denoted ML14093.

Figure 21:
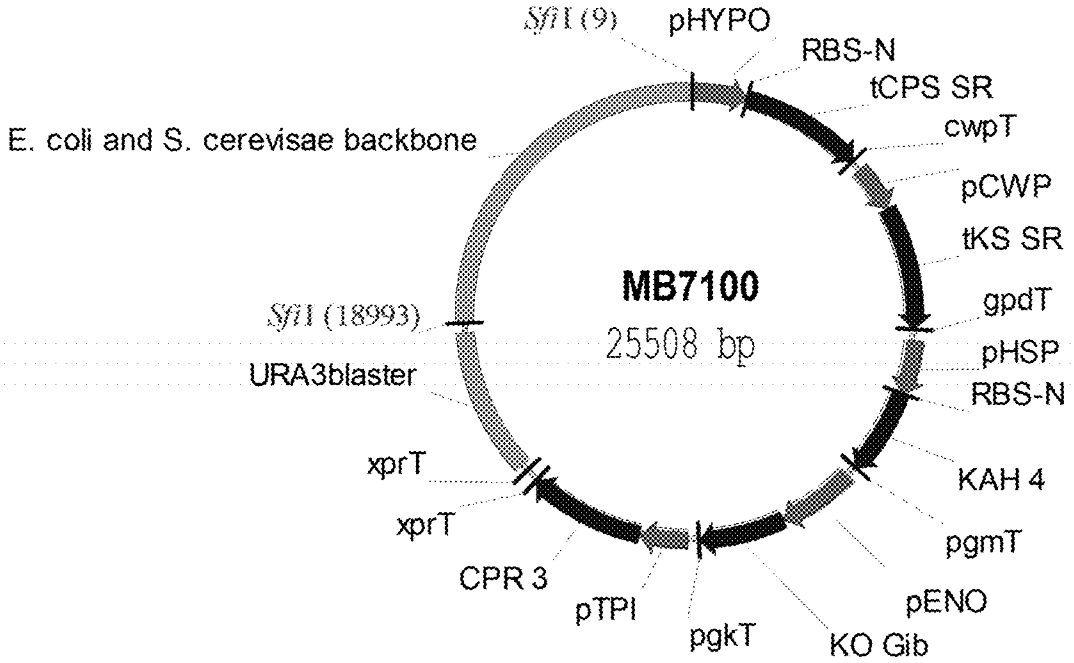
FIG. 21 sets out the map of plasmid MB7100, carrying genes tCPS_SR, tKS_SR, KAH_4, KO_Gib and CPR_3.

Step 6. Strain ML14093 was transformed with a 19.0 kb fragment isolated by gel purification following SfiI digestion of plasmid MB7100 (FIG. 21). MB7100 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 71), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and URA3blaster prototrophic marker. Transformants were selected on minimal medium lacking uracil. One selected rebaudioside A producing uracil prototroph was denoted ML14094.

Example 12: Description of Steviol Glycoside Production Strain ML14087 (MAT-B Lineage)

Step 1. Strain ML13206 (MAT-B, ade1-, ure2-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

1) a 7.0 kb DNA fragment isolated by gel purification following HindIII/NotI digestion of plasmid MB6969 (FIG. 13). This construct encodes a synthetic construct for the overexpression of the codon pair optimized (CpO) ORF of UGT2_1a (SEQ ID NO: 29) linked to the pPGM (SEQ ID NO: 62) promoter and xprT terminator (SEQ ID NO: 69) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 75) linked to the pHSP promoter (SEQ ID NO: 63) and cwpT terminator (SEQ ID NO: 70).

2) a 2.7 kb DNA fragment isolated by gel purification following HindIII/SspI digestion of MB6856 (FIG. 14). This construct encodes tHMGopt (SEQ ID NO: 75) linked to the pHYPO promoter (SEQ ID NO: 64) and gpdT terminator (SEQ ID NO: 71).

3) a 2.5 kb DNA fragment isolated by gel purification following SspI digestion of MB6857 (FIG. 15). This construct encodes tHMGopt (SEQ ID NO: 75) linked to the pHSP promoter (SEQ ID NO: 63) and cwpT terminator (SEQ ID NO: 70).

4) a 2.0 kb DNA fragment isolated by gel purification following SspI digestion of MB6948 (FIG. 16). This construct encodes a synthetic construct for the overexpression of the codon optimized *Y. lipolytica* geranyl-geranyl-pyrophosphate synthetase (GGSopt: SEQ ID NO: 76) linked to the pHSP promoter (SEQ ID NO: 63) and cwpT terminator (SEQ ID NO: 70).

5) a 2.2 kb DNA fragment isolated by gel purification following HindIII/SspI digestion of MB6958 (FIG. 17). This construct encodes GGSopt (SEQ ID NO: 76) linked to the pHYPO (SEQ ID NO: 64) promoter and gpdT terminator (SEQ ID NO: 71). The resulting strain was denoted ML13465.

Step 2. Strain ML13465 was transformed with 2 defined DNA fragments:

1). a 9.7 kb fragment isolated by gel purification following SfiI digestion of plasmid MB7015 (FIG. 18). This construct encodes a synthetic construct for the overexpression of UGT1 (SEQ ID NO: 77) linked to the pENO promoter (SEQ Id NO: 65) and gpdT (SEQ ID NO: 71) terminator, UGT3 (SEQ ID NO: 78) linked to the pHSP promoter (SEQ ID NO: 63) and pgmT terminator (SEQ ID NO: 72), UGT4 (SEQ ID NO: 79) linked to the pCWP promoter (SEQ ID NO: 66) and pgkT terminator (SEQ ID NO: 73), and the lox-flanked nourseothricin resistance marker (NAT). Note that placement of lox sites allows for subsequent removal of nourseothricin resistance via CRE recombinase mediated recombination.

Figure 22:
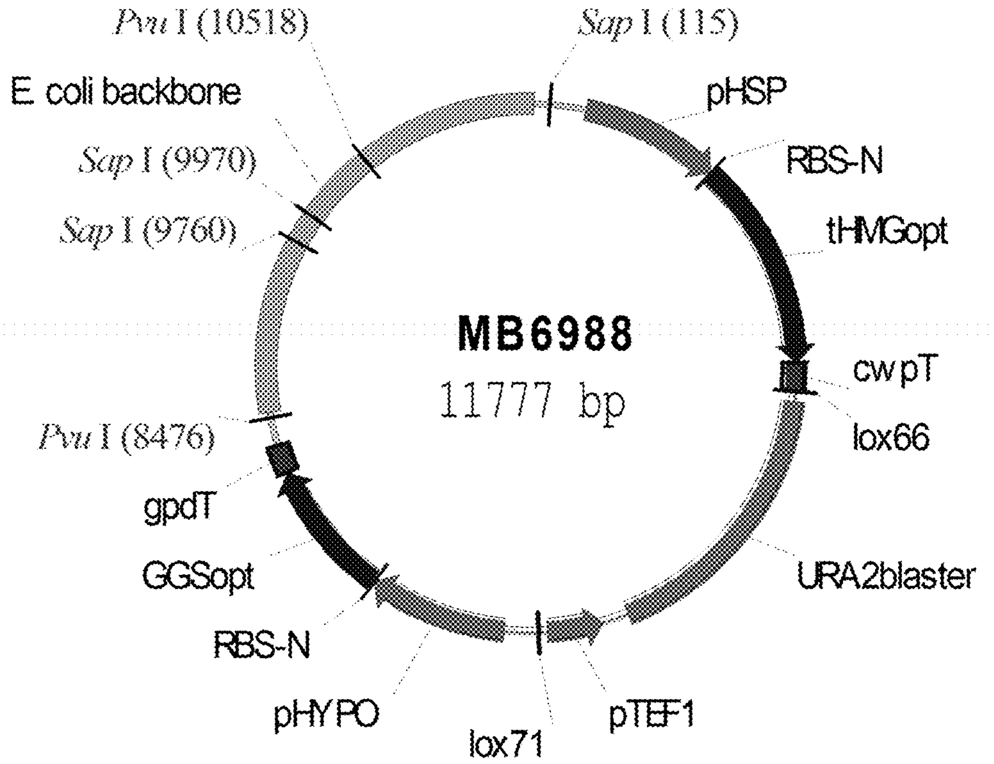
FIG. 22 sets out the map of plasmid MB6988, carrying genes tHMG and GGS

2). a 9.1 kb fragment isolated by gel purification following PvuI/SapI digestion of plasmid MB6988 (FIG. 22). This construct encodes tHMGopt (SEQ ID NO: 75) linked to the pHSP promoter (SEQ ID NO: 63) and cwpT terminator (SEQ ID NO: 70), the lox-flanked URA2blaster prototrophic marker, and GGSopt (SEQ ID NO: 76) linked to the pHYPO promoter (SEQ ID NO: 64) and gpdT terminator (SEQ ID NO: 71). Strains were selected on YPD+100 ug/ml nourseothricin and replica plated to minimal medium lacking uracil. A nourseothricin resistant, uracil prototrophic isolate was denoted ML13490

Step 3. Strain ML13490 was struck to YPD and grown overnight and then struck to 5-FOA plates to allow for recombination mediated loss of the URA2 marker introduced in step 3 above. One selected 5-FOA resistant transformant was denoted ML13501.

Step 4. Strain ML13501 was transformed with a 9.1 kb fragment isolated by gel purification following PvuI/SapI digestion of plasmid MB6988 (FIG. 22). Transformants were selected on minimal medium lacking uracil. One selected uracil prototroph was denoted ML13724.

Figure 23:
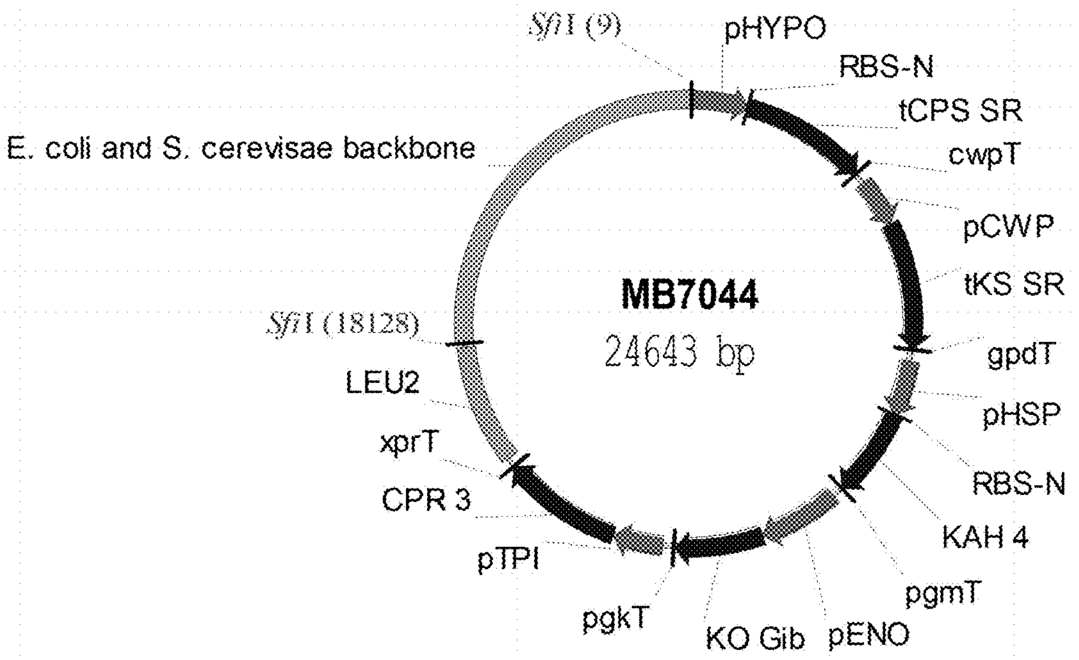
FIG. 23 sets out the map of plasmid MB7044, carrying genes tCPS_SR, tKS_SR, KAH_4, KO_Gib and CPR_3.

Step 5. Strain ML13724 was transformed with an 18.1 kb fragment isolated by gel purification following SfiI digestion of plasmid MB7044 (FIG. 23). MB7044 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 70), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and the LEU2 locus. One selected rebaudioside A-producing transformant was denoted ML14044.

Step 6. Strain ML14044 was struck to YPD and grown overnight and then struck to 5-FOA plates to allow for recombination mediated loss of the URA2 marker introduced in Step 4 above. One selected 5'-FOA resistant transformant was denoted ML14076.

Figure 24:
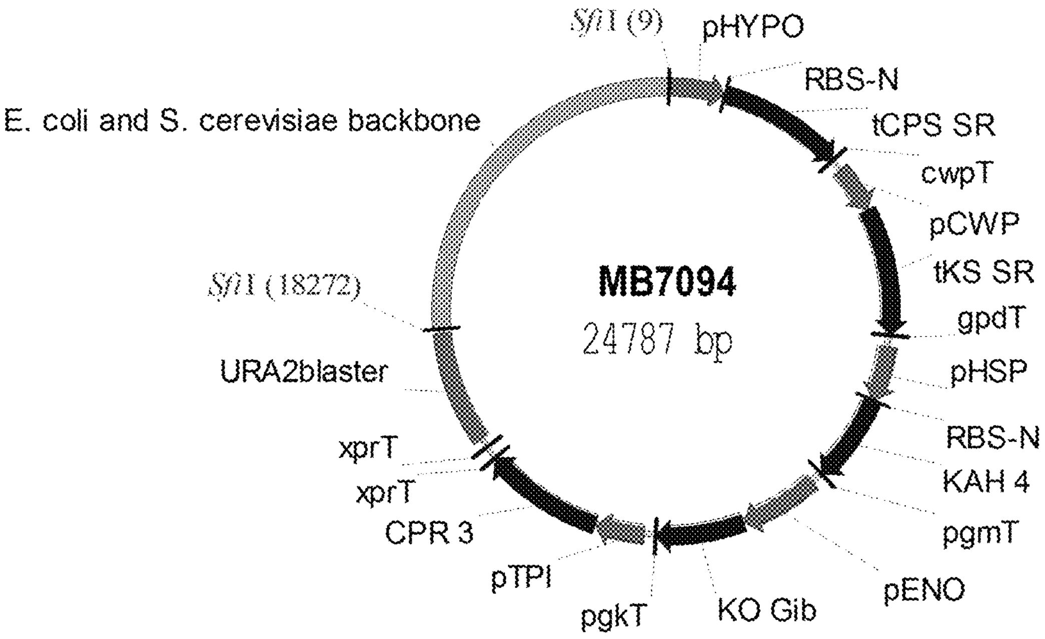
FIG. 24 sets out the map of plasmid MB7094, carrying genes tCPS_SR, tKS_SR, KAH_4, KO_Gib and CPR_3.

Step 7. Strain ML14076 was transformed with a 19.0 kb fragment isolated by gel purification following SfiI digestion of plasmid MB7094 (FIG. 24). MB7094 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 71), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and URA2blaster prototrophic marker. Transformants were selected on minimal medium lacking uracil. One selected rebaudioside A producing uracil prototroph was denoted ML14087.

Example 13: Mating MATA and MATB Lineage and Selecting Steviol Glycoside-Producing Progeny Strains of opposite mating types (ML14094 and ML14087) with complementary nutritional deficiencies (ADE1+lys1− and ade1−LYS1+) were allowed to mate and then plated on selective media that would allow only diploids to grow (minimal media lacking both adenine and lysine). Diploid cells (ML14143) were then induced to undergo meiosis and sporulation by starvation, and the resulting haploid progenies were replica-plated to identify prototrophic isolates with hygromycin and nourseothricin resistance. One selected rebaudioside A-producing strain was denoted ML14737

Example 14: Making the Strain UGT2_1a-Free

Figure 25:
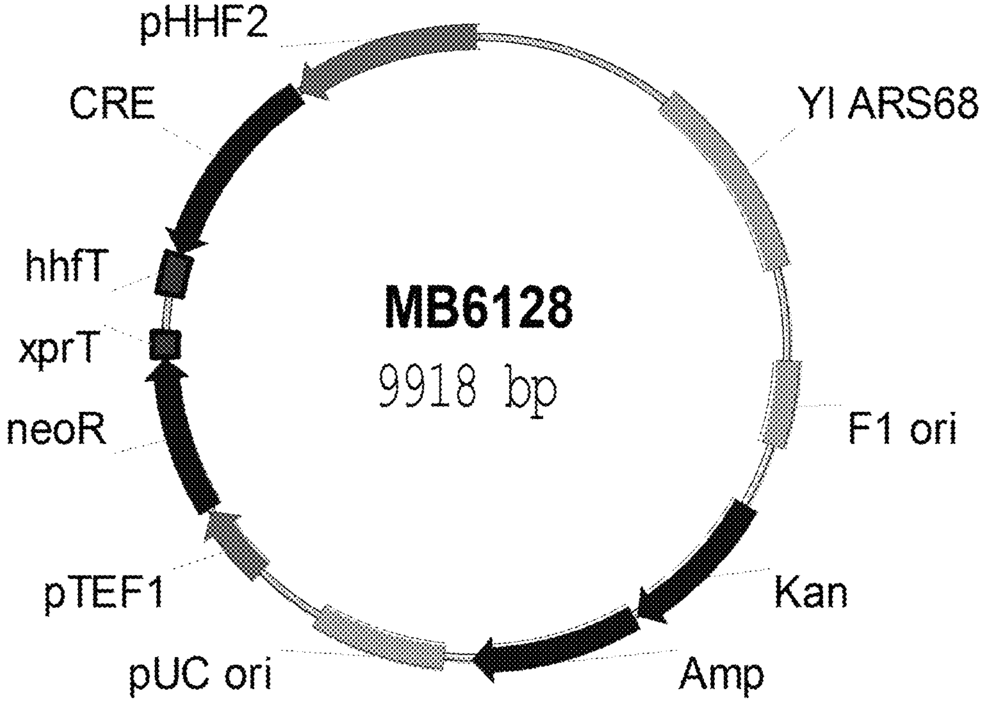
FIG. 25 sets out the map of plasmid MB6128, carrying CRE gene, which is used for removal of the antibiotic marker.

The hygromycin antibiotic marker and the nourseothricin antibiotic marker were removed from strain ML14737 after transformation with MB6128 (FIG. 25) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator, and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14869. This strain no longer produces rebaudioside A due to the loss of UGT2_1a along with the hygromycin resistance and produces the intermediate rubusoside instead.

Example 15: Transformation of UGT2 Genes

Figure 26:
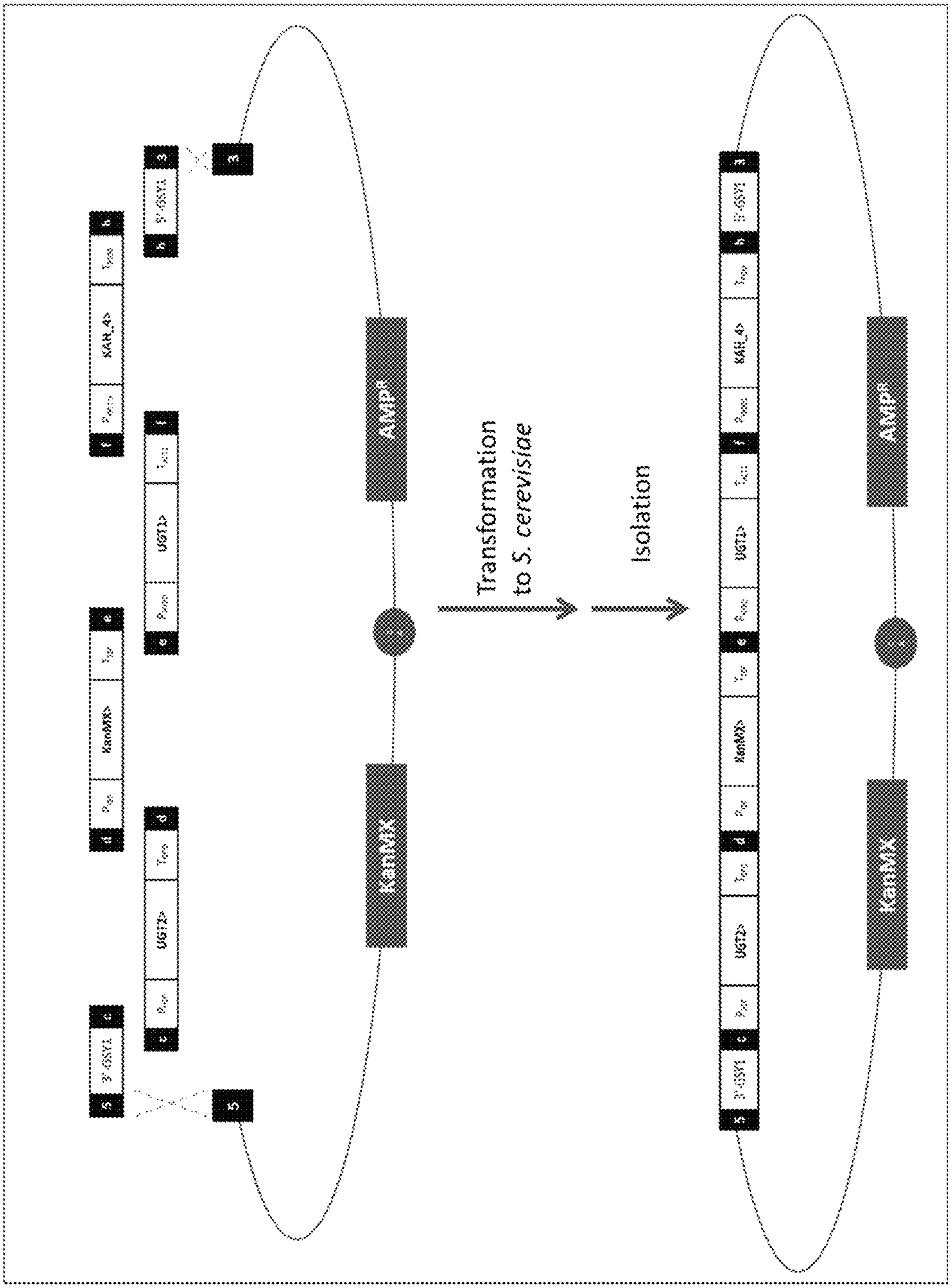
FIG. 26 sets out the method of assembly in a plasmid of genes UGT2, KanMX, UGT1 and KAH_4, flanked by gsy1 integration flanks.

The UGT2 gene variants and UGT2_1a as control, were placed behind the *Yarrowia lipolytica* pHSP promoter (SEQ ID NO: 63) and combined with *Yarrowia lipolytica* terminator gpdT (SEQ ID NO: 71). Together with UGT1 (SEQ ID NO: 77), KAH_4 (SEQ ID NO: 82), the lox-flanked G418 resistance marker (KanMX) and *Yarrowia lipolytica* GSY1 integration flanks, each UGT2 was assembled into a construct on the CEN plasmid p417[5-3] in *Saccharomyces cerevisiae* (see FIG. 26).

TABLE 10

Promoters, ORFs and Terminators used in construction of strains with UGT2 variants

| Promoter | ORF | Terminator |
|---|---|---|
| pHSP (SEQ ID NO: 63) | UGT2 (SEQ ID NO: 5, 8, 13, 16, 19, 24, 26 and 29) | gpdT (SEQ ID NO: 71) |
| Ag_TEF1 | KanMX | Ag_TEF1 |
| pHYPO (SEQ ID NO: 64) | UGT1 (SEQ ID NO: 77) | act1T (SEQ ID NO: 74) |
| pYP001 (SEQ ID NO: 68) | KAH_4 (SEQ ID NO: 82) | pgmT (SEQ ID NO: 72) |

Figure 27:
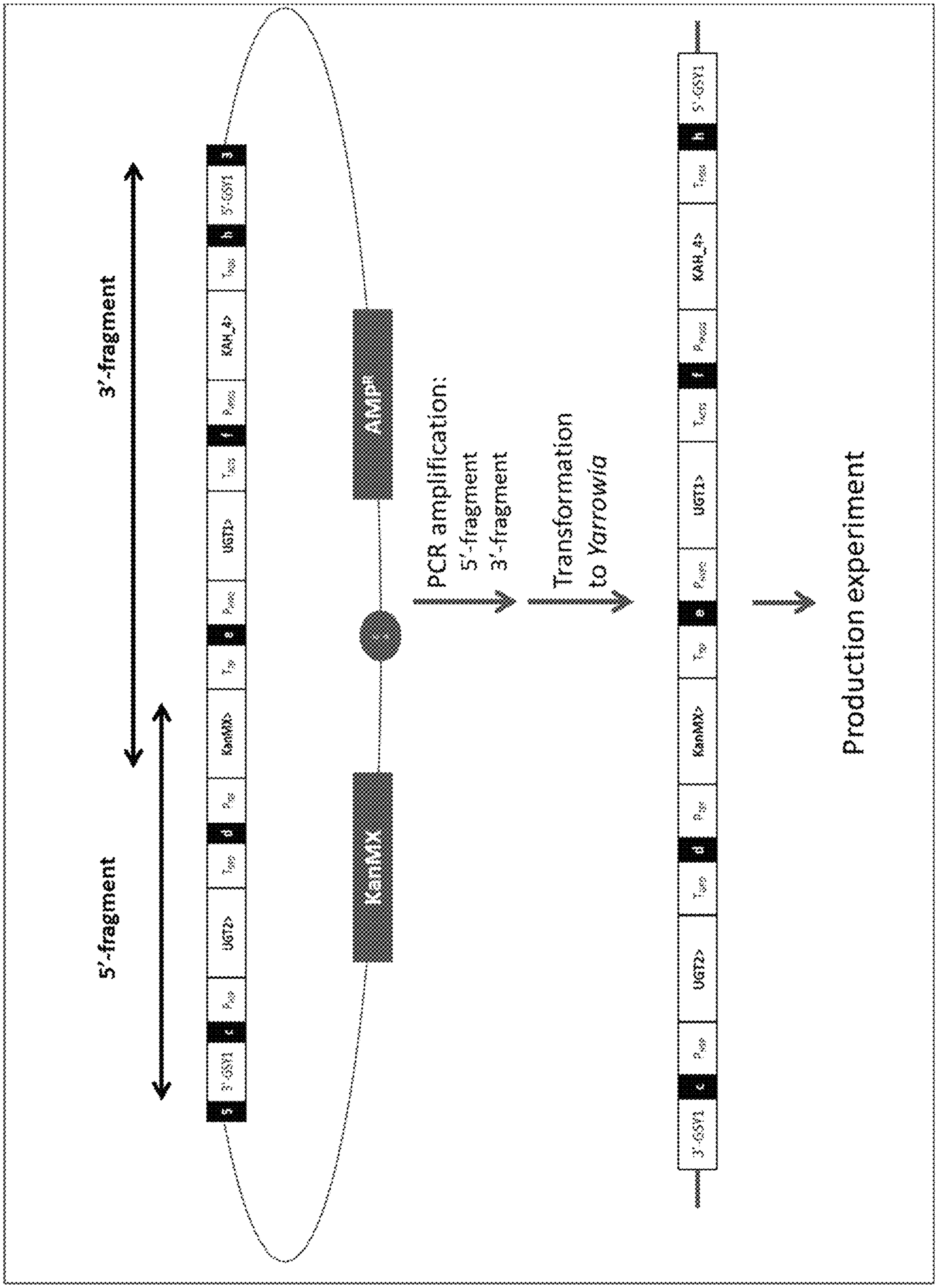
FIG. 27 sets out the method of amplification of the plasmid of FIG. 26, and transformation to *Yarrowia*.

These constructs, one for each UGT2, were used as template in PCRs to amplify the 5'-part and the 3'-part (see FIG. 27). This 5'-part consists of everything between the beginning of the 3'-GSY1 integration flank and the end of the KanMX open reading frame. The 3'-part consists of everything between the second codon of the KanMX open reading frame and the end of the 5'-GSY1 integration flank.

For the UGT2 testing each 5'-part and 3'-part combination was transformed to strain ML14869. Transformants were selected on YPD medium containing G418. From each transformation 12 colonies were selected for a production experiment.

Example 16: Production of RebA with *Y. Lipolytica*

A pre-culture was inoculated with colony material from YEPh-D agar. The pre-culture was grown in 200 µl YEP with glucose as carbon source. The pre-culture was incubated 72 hours in an Infors incubator at 27° C., 750 rpm and 80% humidity. 40 µl of pre-culture was used to inoculate 2.5 ml YEP with glucose as carbon source. The main cultures were incubated 120 hours in an Infors incubator at 27° C., 550 rpm, 80% humidity. After 120 h the main culture was spun down at 2750 rpm for 10 min. From the supernatant 100 µl was taken and diluted 2.5 times in 55% acetonitrile. Further dilutions were made in 33% acetonitrile.

Figure 28:
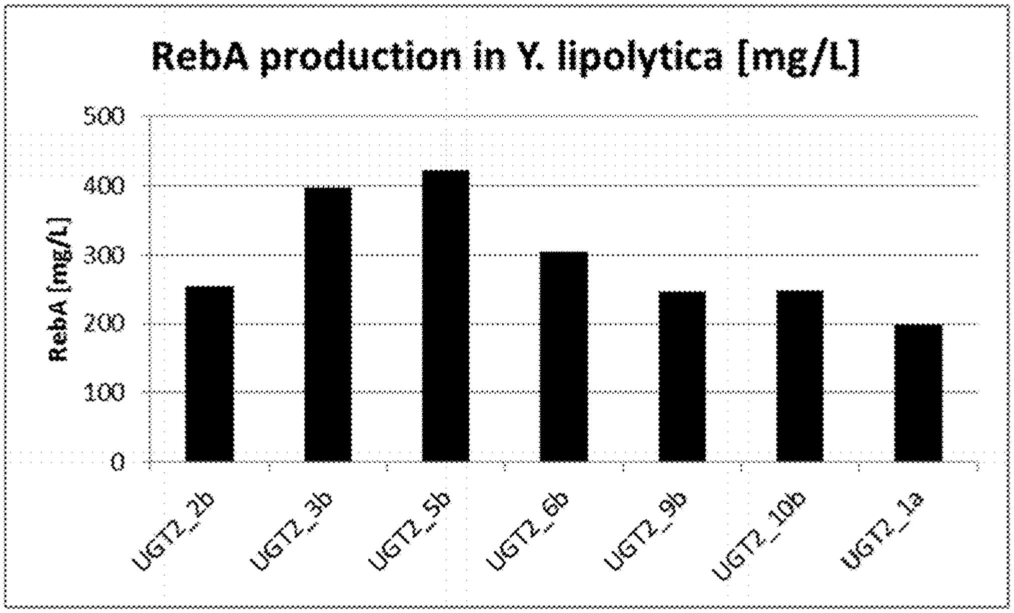
FIG. 28 sets out the production of rebaudioside A in *Yarrowia* strains expressing different variants of UGT2.

The results are set out in in FIG. 28 and Table 11. It can be seen that the strains that express the variant UGT2s produce higher titers of RebA.

TABLE 11

Rebaudioside A production in *Yarrowia* strains expressing UGT2 variant enzymes

| Sample | RebA (mg/L) |
|---|---|
| UGT2_2b | 254 |
| UGT2_3b | 396 |
| UGT2_5b | 422 |
| UGT2_9b | 246 |
| UGT2_10b | 249 |
| UGT2_1a | 198 |

Example 17: Production of RebM with *Y. Lipolytica*

A pre-culture was inoculated with colony material from YEPh-D agar. The pre-culture was grown in 200 µl YEP with glucose as carbon source. The pre-culture was incubated 72 hours in an Infors incubator at 27° C., 750 rpm and 80% humidity. 40 µl of pre-culture was used to inoculate 2.5 ml YEP with glucose as carbon source. The main cultures were incubated 120 hours in an Infors incubator at 27° C., 550 rpm, 80% humidity. After 120 h the main culture was spun down at 2750 rpm for 10 min. From the supernatant 100 µl was taken and diluted 2.5 times in 55% acetonitrile. Further dilutions were made in 33% acetonitrile.

Figure 29:
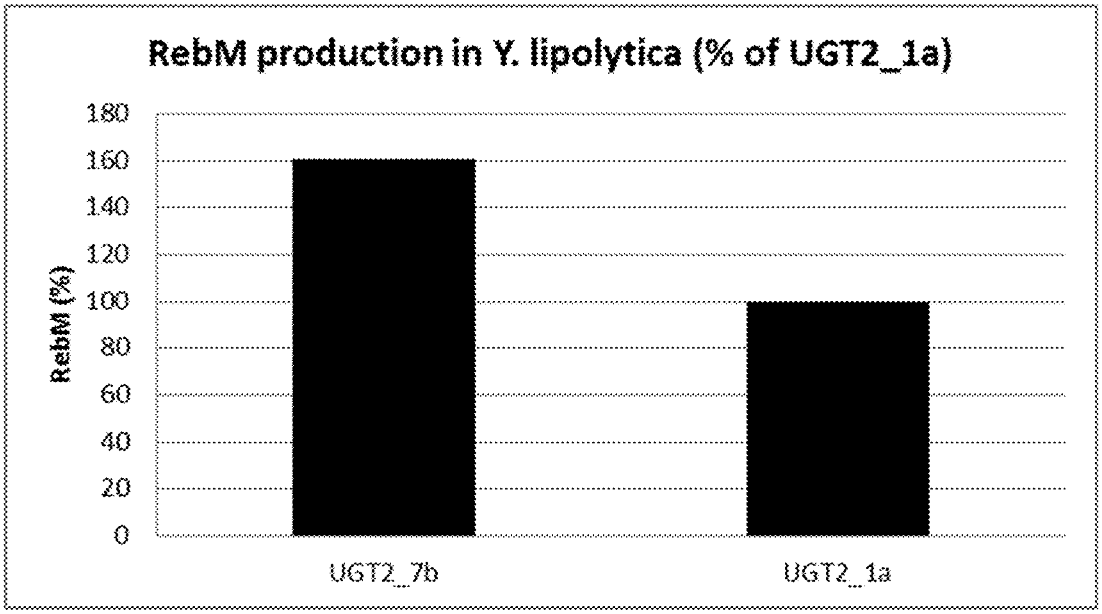

The results are set out in in FIG. 29 and Table 12. It can be seen that the strains that express the variant UGT2s produce higher titers of RebM.

TABLE 12

Rebaudioside M production in *Yarrowia* strains expressing UGT2 variant enzymes

| Sample | RebM (mg/L) |
|---|---|
| UGT2_7b | 37.5 |
| UGT2_1a | 23.3 |

Example 18

In order to evaluate the effect of different variants of UGT2 on steviol glycoside production in bioreactors, two of the strains described in example 15 were selected. One strain expresses UGT2_6b and the other strain expresses UGT2_7b. The fermentation protocol applied was a fed-batch fermentation and whole broth samples were taken daily for the analysis of steviol glycosides with LC/MS.

Figure 30:
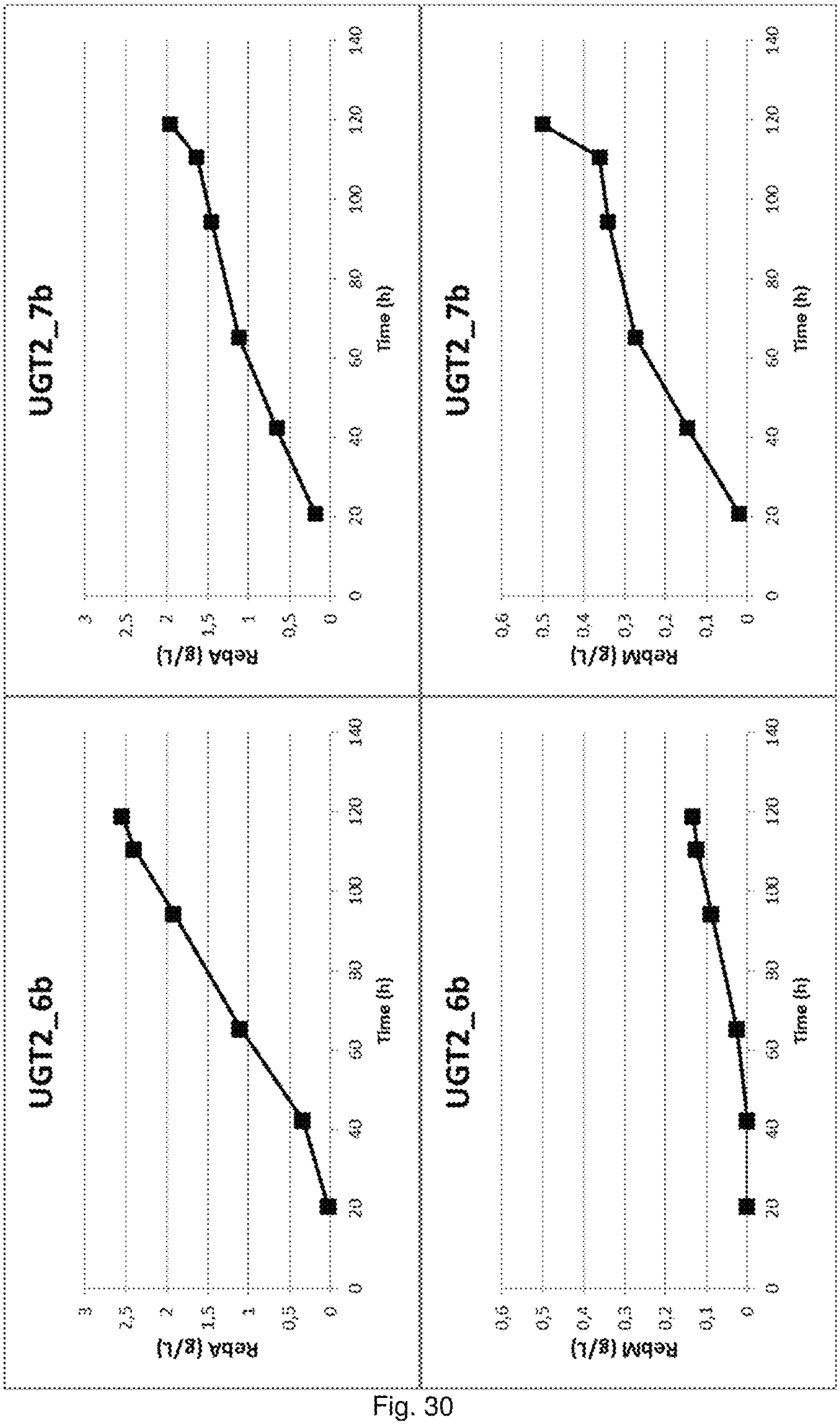
FIG. 30. RebA (top panels) and RebM (bottom panels) production in strains expressing either UGT2_6b (left panels) or UGT2_7b (right panels).

As can be seen in FIG. 30, the strain expressing UGT2_6b makes more RebA compared to the strain expressing the UGT2_7b. However, the strain expressing the UGT2_7b produces substantially more RebM compared to the strain expressing the UGT2_6b. Both strains make more RebA than RebM. At the end of the fermentation, with the strain expressing UGT2_6b the RebA concentration is 20 fold higher than the RebM concentration, whereas in the strain expressing the UGT2_7b, this is four fold higher. The different product ratio's reflect the intrinsic differences of the UGT2 properties, where the UGT2_7b has a higher activity of glycosylation of the glucose on the 19-position compared to the UGT2_6b. Products of the glycosylation reaction on the 19-position, such as RebE and RebD, from stevioside and RebA respectively, are further converted to RebM by the activity of UGT4, see FIG. 32.

This illustrates that production can be effectively steered to the product of interest by using the different variants of UGT2 here described.

TABLE 13

| Description of the sequence listing | |
|---|---|
| SEQ ID NO | Description |
| SEQ ID NO: 1 | UGT2_1b amino acid |
| SEQ ID NO: 2 | UGT2_1b CpO for *S. cerevisiae* |
| SEQ ID NO: 3 | UGT2_2b amino acid |
| SEQ ID NO: 4 | UGT2_2b CpO for *S. cerevisiae* |
| SEQ ID NO: 5 | UGT2_2b CpO for *Y. lipolitica* |
| SEQ ID NO: 6 | UGT2_3b amino acid |
| SEQ ID NO: 7 | UGT2_3b CpO for *S. cerevisiae* |
| SEQ ID NO: 8 | UGT2_3b CpO for *Y. lipolitica* |
| SEQ ID NO: 9 | UGT2_4b amino acid |
| SEQ ID NO: 10 | UGT2_4b CpO for *S. cerevisiae* |
| SEQ ID NO: 11 | UGT2_5b amino acid |
| SEQ ID NO: 12 | UGT2_5b CpO for *S. cerevisiae* |
| SEQ ID NO: 13 | UGT2_5b CpO for *Y. lipolitica* |
| SEQ ID NO: 14 | UGT2_6b amino acid |
| SEQ ID NO: 15 | UGT2_6b CpO for *S. cerevisiae* |
| SEQ ID NO: 16 | UGT2_6b CpO for *Y. lipolitica* |
| SEQ ID NO: 17 | UGT2_7b amino acid |
| SEQ ID NO: 18 | UGT2_7b CpO for *S. cerevisiae* |
| SEQ ID NO: 19 | UGT2_7b CpO for *Y. lipolitica* |
| SEQ ID NO: 20 | UGT2_8b amino acid |
| SEQ ID NO: 21 | UGT2_8b CpO for *S. cerevisiae* |
| SEQ ID NO: 22 | UGT2_9b amino acid |
| SEQ ID NO: 23 | UGT2_9b CpO for *S. cerevisiae* |
| SEQ ID NO: 24 | UGT2_9b CpO for *Y. lipolitico* |
| SEQ ID NO: 25 | UGT2_10b amino acid |
| SEQ ID NO: 26 | UGT2_10b CpO for *Y. lipolitica* |
| SEQ ID NO: 27 | UGT2_1a amino acid |
| SEQ ID NO: 28 | UGT2_1a CpO for *S. cerevisiae* |
| SEQ ID NO: 29 | UGT2_1a CpO for *Y. lipolitica* |
| SEQ ID NO: 30 | Eno2 promoter from *S. cerevisiae* |
| SEQ ID NO: 31 | ERG20 nucleic acid from *S. cerevisiae* |
| SEQ ID NO: 32 | Adh1 terminator from *S. cerevisiae* |
| SEQ ID NO: 33 | Fba1 promoter from *S. cerevisiae* |

TABLE 13-continued

| Description of the sequence listing | |
|---|---|
| SEQ ID NO | Description |
| SEQ ID NO: 34 | tHMG nucleic acid from *S. cerevisiae* |
| SEQ ID NO: 35 | Adh2 terminator from *S. cerevisiae* |
| SEQ ID NO: 36 | Tef1 promoter from *S. cerevisiae* |
| SEQ ID NO: 37 | BTS1 nucleic acid from *S. cerevisiae* |
| SEQ ID NO: 38 | Gmp1 terminator from *S. cerevisiae* |
| SEQ ID NO: 39 | Pgk1 promoter from *S. cerevisiae* |
| SEQ ID NO: 40 | Kl prom 12 promoter |
| SEQ ID NO: 41 | trCPS from *S. rebaudiana* CpO for *S. cerevisiae* |
| SEQ ID NO: 42 | trKS from *S. rebaudiana* CpO for *S. cerevisiae* |
| SEQ ID NO: 43 | TAL1 terminator from *S. cerevisiae* |
| SEQ ID NO: 44 | KO from *Giberella fujikuroi* CpO for S. |
| SEQ ID NO: 45 | Tpi1 terminator from *S. cerevisiae* |
| SEQ ID NO: 46 | Ag lox_TEF1.pro nucleic acid construct |
| SEQ ID NO: 47 | KANMX ORF CpO for *S. cerevisiae* |
| SEQ ID NO: 48 | Ag Tef1_lox.ter nucleic acid construct |
| SEQ ID NO: 49 | KAH_4 from *Arabidopsis thaliana* CpO for *S. cerevisiae* |
| SEQ ID NO: 50 | Kl prom 6.pro promoter |
| SEQ ID NO: 51 | CPR_3 from Arabidopsis thaliana CpO for *S. cerevisiae* |
| SEQ ID NO: 52 | Pdc1 terminator from *S. cerevisiae* |
| SEQ ID NO: 53 | Kl prom3 promoter |
| SEQ ID NO: 54 | UGT1 from *S. rebaudiana* CpO for *S. cerevisiae* |
| SEQ ID NO: 55 | Tdh1 terminator from *S. cerevisiae* |
| SEQ ID NO: 56 | Kl prom 2 promoter |
| SEQ ID NO: 57 | UGT3 from *S. rebaudiana* CpO for *S. cerevisiae* |
| SEQ ID NO: 58 | UGT4 from *S. rebaudiana* CpO for *S. cerevisiae* |

TABLE 13-continued

| Description of the sequence listing | |
|---|---|
| SEQ ID NO | Description |
| SEQ ID NO: 59 | Eno1 terminator from *S. cerevisiae* |
| SEQ ID NO: 60 | Eno1 promoter from *S. cerevisiae* |
| SEQ ID NO: 61 | Gap1T promoter from *K. lactis* |
| SEQ ID NO: 62 | PGM promoter from *Y. lipolitica* |
| SEQ ID NO: 63 | HSP promoter from *Y. lipolitica* |
| SEQ ID NO: 64 | HYPO promoter from *Y. lipolitica* |
| SEQ ID NO: 65 | ENO promoter from *Y. lipolitica* |
| SEQ ID NO: 66 | CWP promoter from *Y. lipolitica* |
| SEQ ID NO: 67 | TPI promoter from *Y. lipolitica* |
| SEQ ID NO: 68 | YP001 promoter from *Y. lipolitica* |
| SEQ ID NO: 69 | Xpr terminator from *Y. lipolitica* |
| SEQ ID NO: 70 | Cwp terminator from *Y. lipolitica* |
| SEQ ID NO: 71 | Gpd terminator from *Y. lipolitica* |
| SEQ ID NO: 72 | Pgm terminator from *Y. lipolitica* |
| SEQ ID NO: 73 | Pgk terminator from *Y. lipolitica* |
| SEQ ID NO: 74 | act1T terminator from *Y. lipolitica* |
| SEQ ID NO: 75 | tHMG CpO for *Y. lipolitica* |
| SEQ ID NO: 76 | GGS CpO for *Y. lipolitica* |
| SEQ ID NO: 77 | UGT1 CpO for *Y. lipolitica* |
| SEQ ID NO: 78 | UGT3 CpO for *Y. lipolitica* |
| SEQ ID NO: 79 | UGT4 CpO for *Y. lipolitica* |
| SEQ ID NO: 80 | tCPS from *S. rebaudiana* CpO for *Y. lipolitica* |
| SEQ ID NO: 81 | tKS from *S. rebaudiana* CpO for *Y. lipolitica* |
| SEQ ID NO: 82 | KAH_4 CpO for *Y. lipolitica* |
| SEQ ID NO: 83 | KO from *Gibberella fujikori* CpO for *Y. lipolitica* |
| SEQ ID NO: 84 | CPR_3 CpO for *Y. lipolitica* |

The invention claimed is:

1. A recombinant host comprising a recombinant nucleic acid sequence encoding a polypeptide having at least 90% sequence identity to the amino acid sequence set forth in SEQ ID NO: 17.

2. The recombinant host of claim 1 which is capable of producing a glycosylated diterpene.

3. The recombinant host of claim 1, further comprising one or more recombinant nucleotide sequence(s) encoding:
- a polypeptide having ent-copalyl pyrophosphate synthase activity;
- a polypeptide having ent-Kaurene synthase activity;
- a polypeptide having ent-Kaurene oxidase activity; and
- a polypeptide having kaurenoic acid 13-hydroxylase activity.

4. The recombinant host of claim 1, which comprises a recombinant nucleic acid sequence encoding a polypeptide having NADPH-cytochrome p450 reductase activity.

5. The recombinant host of claim 1 which comprises a recombinant nucleic acid sequence encoding one or more of:
- (i) a polypeptide having UGT74G1 (UGT3) activity;
- (ii) a polypeptide having UGT85C2 (UGT1) activity; and
- (iii) a polypeptide having UGT76G1 (UGT4) activity.

6. The recombinant host of claim 1 which comprises a recombinant nucleic acid sequence encoding an additional polypeptide having UGT2 activity.

7. The recombinant host of claim 1, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma*, or *Escherichia*.

8. The recombinant host of claim 7, wherein the recombinant host is a *Saccharomyces cerevisiae* cell, a *Yarrowia lipolytica* cell, a *Candida krusei* cell, an *Issatchenkia orientalis* or an *Escherichia coli* cell.

9. The recombinant host of claim 1, wherein the ability of the host to produce geranylgeranyl diphosphate (GGPP) is upregulated.

10. The recombinant host of claim 1, comprising one or more recombinant nucleic acid sequence(s) encoding hydroxymethylglutaryl-CoA reductase, farnesyl-pyrophosphate synthetase and geranylgeranyl diphosphate synthase.

11. The recombinant host of claim 1 which comprises a nucleic acid sequence encoding one or more of:
- a polypeptide having hydroxymethylglutaryl-CoA reductase activity;
- a polypeptide having farnesyl-pyrophosphate synthetase activity;
- a polypeptide having geranylgeranyl diphosphate synthase activity.

12. A process for the preparation of a glycosylated diterpene which comprises fermenting the recombinant host of claim 2 in a suitable fermentation medium, and optionally recovering the glycosylated diterpene.

13. The process of claim 12 for the preparation of a glycosylated diterpene, wherein the process is carried out on an industrial scale.

14. A method for converting a first glycosylated diterpene into a second glycosylated diterpene, which method comprises:
- contacting said first glycosylated diterpene with the recombinant host of claim 1, a cell free extract derived from such a recombinant host or an enzyme preparation derived from either thereof;

thereby to convert the first glycosylated diterpene into the second glycosylated diterpene.

15. The method of claim 14, wherein the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

16. The method of claim 15, wherein the first glycosylated diterpene is steviol-13-monoside, steviol-19-monoside, rubusoside, stevioside, rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy) kaur-16-en-18-oic acid 2-O-β-D-glucopyranosyl-β-D-glucopyranosyl ester.

17. A nucleic acid construct comprising a polynucleotide sequence encoding a polypeptide having at least 90% sequence identity with the amino acid sequence of SEQ ID NO:17.

18. The nucleic acid construct of claim 17 which is an expression vector, wherein the polynucleotide sequence is operably linked to at least one control sequence for the expression of the polynucleotide sequence in a host cell.

19. A method of producing the nucleic acid construct of claim 17, comprising:

(a) cultivating a recombinant host cell comprising a recombinant nucleic acid sequence encoding a polypeptide having at least 90% sequence identity to the amino acid sequence set forth in SEQ ID NO: 17 under conditions conducive to the production of the nucleic acid construct by the host cell, and optionally, (b) recovering the nucleic acid construct.

* * * * *

SEQUENCE LISTING

```
<160> NUMBER OF SEQ ID NOS: 84

<210> SEQ ID NO 1
<211> LENGTH: 473
<212> TYPE: PRT
<213> ORGANISM: Artificial sequence
<220> FEATURE:
<223> OTHER INFORMATION: UGT2_1b variant

<400> SEQUENCE: 1

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Leu Ala Ser Asp Gly Leu Gln Glu Pro Leu Thr Arg Phe Leu Glu Ser
```

-continued

```
            100                 105                 110

Ser Ser Pro Asp Trp Ile Ile Tyr Asp Tyr Thr His Tyr Trp Leu Pro
        115                 120                 125

Glu Ile Ala Ala Ser Leu Gly Val Ala Arg Ala His Phe Ser Val Thr
    130                 135                 140

Thr Pro Trp Ala Leu Ala Phe Met Gly Pro Ser Ala Asp Ala Met Ile
145                 150                 155                 160

Asn Gly Ser Asp Gly Arg Thr Glu Val Glu Asp Phe Thr Val Pro Pro
                165                 170                 175

Lys Trp Ile Pro Phe Pro Thr Thr Val Ala Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Cys Asp Cys Leu Leu Ser Arg Thr Tyr
    210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                245                 250                 255

Glu Lys Asp Glu Asn Trp Val Ser Ile Lys Asp Trp Leu Asp Lys Gln
            260                 265                 270

Glu Lys Gly Ser Val Val Tyr Val Ala Leu Gly Ser Glu Val Leu Leu
        275                 280                 285

Thr Glu Glu Glu Val Val Glu Leu Ala Leu Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Glu Ser Leu Arg Leu Val Val Val Glu Lys Glu Gly Glu Ile Tyr
            420                 425                 430

Arg Glu Lys Ala Arg Glu Met Ser Lys Val Tyr Ser Asp Thr Lys Arg
        435                 440                 445

Glu Lys Glu Tyr Val Asp Gln Phe Val Asp Tyr Leu Glu Lys Asn Ala
    450                 455                 460

Arg Ala Val Ala Ile Asp His Glu Ser
465                 470


<210> SEQ ID NO 2
<211> LENGTH: 1419
<212> TYPE: DNA
<213> ORGANISM: Artificial sequence
<220> FEATURE:
<223> OTHER INFORMATION: UGT2_1b CpO for S. cerevisiae
```

<400> SEQUENCE: 2

```
atggccactt ctgactccat cgttgatgac agaaagaagt tgcacatcgt tatgttccca      60

tggttagctt tcggtcacat tatcccatac ttgcaattgg ctaaattgat tgctgaaaag     120

ggtcacaaag tctctttctt gtccaccacc agaaacatcc aaagattatc ttctcacatt     180

tctccattga tcaacttcgt caagttgact ttaccaagag ttcaagaatt gccagaagat     240

gctgaagcta ccaccgatgt ccatccagaa gatatcccat acttgaagtt ggcttctgat     300

ggtttgcaag aaccattgac tagattcttg gaatcttctt ctccagactg gattatctac     360

gactacactc actactggtt accagaaatt gctgcctctt tgggtgttgc tcgtgctcat     420

ttctccgtta ccactccatg ggctttggct ttcatgggtc catctgctga tgctatgatc     480

aacggttctg atggtagaac cgaagtcgaa gacttcaccg ttccaccaaa atggatccca     540

ttcccaacca ctgtcgcttg gagaaagcac gatttggcca gattagttcc atacaaggcc     600

ccaggtatct ctgacggtta cagaatgggt ttagtcttga agggttgtga ctgtttgttg     660

tccagaactt accatgaatt cggtactcaa tggttacctt tgttggaaga attgcaccaa     720

gtcccagttg ttccagttgg tttgttgcct ccttctatcc caggtgacga aaaggacgaa     780

aactgggttt ccatcaagga ctggttagat aagcaagaaa agggttccgt tgtctacgtt     840

gctttgggtt ctgaagtctt gttgactgaa gaagaagttg ttgaattggc tttgggtttg     900

gaattgtccg gtctaccatt tttctgggct tacagaaagc caaagggtcc agctaagtct     960

gactctgttg aattgccaga tggtttcgtc gaaagaacca gagacagagg tttggtctgg    1020

acttcctggg ctccacaatt gagaattttg tcccacgaat ctgttggtgg tttcgttacc    1080

cactgtggtt ctggttccat tgtcgaaggt ttgatgttcg gtcacccatt gatcatgttg    1140

ccaatcttcg gtgaccaacc attgaacgct agattattgg aagacaagca agtcggtatt    1200

gaaatcccaa gaaacgaaga agacggttgt ttgaccaagg aatctgttgc cgaatctcta    1260

agattggttg ttgtcgaaaa ggaaggtgaa atctacagag aaaaggctag agaaatgtcc    1320

aaggtttact ctgataccaa gagagaaaag gaatatgtcg accaatttgt tgactacttg    1380

gaaaagaacg ctcgtgccgt tgccattgac cacgaaagc                           1419
```

<210> SEQ ID NO 3
<211> LENGTH: 473
<212> TYPE: PRT
<213> ORGANISM: Artificial sequence
<220> FEATURE:
<223> OTHER INFORMATION: UGT2_2b variant

<400> SEQUENCE: 3

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
```

-continued

```
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Cys Asp Cys Leu Leu Ser Arg Thr Tyr
    210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                245                 250                 255

Glu Lys Asp Glu Asn Trp Val Ser Ile Lys Asp Trp Leu Asp Lys Gln
            260                 265                 270

Glu Lys Gly Ser Val Val Tyr Val Ala Leu Gly Ser Glu Val Leu Leu
        275                 280                 285

Thr Glu Glu Glu Val Val Glu Leu Ala Leu Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Gln Arg Asn Glu Glu Asp Gly Cys Leu Thr Lys Glu Ser Val
                405                 410                 415

Ala Glu Ser Leu Arg Leu Val Val Val Glu Lys Glu Gly Glu Ile Tyr
            420                 425                 430

Arg Glu Lys Ala Arg Glu Met Ser Lys Val Tyr Ser Asp Thr Lys Arg
        435                 440                 445

Glu Lys Glu Tyr Val Asp Gln Phe Val Asp Tyr Leu Glu Lys Asn Ala
    450                 455                 460

Arg Ala Val Ala Ile Asp His Glu Ser
465                 470
```

<210> SEQ ID NO 4
<211> LENGTH: 1419
<212> TYPE: DNA
<213> ORGANISM: Artificial sequence
<220> FEATURE:
<223> OTHER INFORMATION: UGT2_2b CpO for S. cerevisiae

<400> SEQUENCE: 4

```
atggccactt ctgactccat cgttgatgac agaaagaagt tgcacatcgt tatgttccca      60
tggttagctt tcggtcacat tatcccatac ttgcaattgg ctaaattgat tgctgaaaag     120
ggtcacaaag tctctttctt gtccaccacc agaaacatcc aaagattatc ttctcacatt     180
tctccattga tcaacttcgt caagttgact ttaccaagag ttcaagaatt gccagaagat     240
gctgaagcta ccaccgatgt ccatccagaa gatatcccat acttgaagaa ggcttctgat     300
ggtttgcaac cagaagtcac tgaattcttg gaacaacact ctccagactg gattatctac     360
gactacactc actactggtt accatccatt gctactaagc acggtgtttc tcgtgctcat     420
ttctccgtta ccactccatg ggctattgct tacatgggtc caactgctga tgctatgatc     480
aacggttctg atggtagaac cactccagaa gacttcaccg ttccaccaaa atggttccca     540
ttcccaacca aggtctgttg gagaaagcac gatttggcca gattagttcc atacaaggcc     600
ccaggtatct ctgacggtta cagaatgggt ttagtcttga agggttgtga ctgtttgttg     660
tccagaactt accatgaatt cggtactcaa tggttacctt tgttggaaga attgcaccaa     720
gtcccagttg ttccagttgg tttgttgcct ccttctatcc caggtgacga aaaggacgaa     780
aactgggttt ccatcaagga ctggttagat aagcaagaaa agggttccgt tgtctacgtt     840
gctttgggtt ctgaagtctt gttgactgaa gaagaagttg ttgaattggc tttgggtttg     900
gaattgtccg gtctaccatt tttctgggct tacagaaagc caaagggtcc agctaagtct     960
gactctgttg aattgccaga tggtttcgtc gaaagaacca gagacagagg tttggtctgg    1020
acttcctggg ctccacaatt gagaattttg tcccacgaat ctgttggtgg tttcgttacc    1080
cactgtggtt ctggttccat tgtcgaaggt ttgatgttcg gtcacccatt gatcatgttg    1140
ccaatcttcg gtgaccaacc attgaacgct agattattgg aagacaagca agtcggtatt    1200
gaaatccaaa gaaacgaaga agacggttgt ttgaccaagg aatctgttgc cgaatctcta    1260
agattggttg ttgtcgaaaa ggaaggtgaa atctacagag aaaaggctag agaaatgtcc    1320
aaggtttact ctgataccaa gagagaaaag gaatatgtcg accaatttgt tgactacttg    1380
gaaaagaacg ctcgtgccgt tgccattgac cacgaaagc                           1419
```

<210> SEQ ID NO 5
<211> LENGTH: 1419
<212> TYPE: DNA
<213> ORGANISM: Artificial sequence
<220> FEATURE:
<223> OTHER INFORMATION: UGT2_2b CpO for Y. lipolitica

<400> SEQUENCE: 5

```
atggccacct ccgactccat tgtcgacgac cgaaagaagc tccacattgt catgttcccc      60
tggctcgcct ttggccacat cattccctac ctccagctcg ccaagctcat tgctgagaag     120
ggccacaagg tttctttcct ctccaccacc cgaaacatcc agcgactctc ttcccacatc     180
tctcccctca tcaactttgt caagctcacc ctcccccgag tccaggagct tcccgaggat     240
gctgaggcca ccactgatgt ccacccccgag gacatcccct acctcaagaa ggcttccgac     300
ggtctgcagc ccgaggtcac tgagtttctc gagcagcact ctcccgactg gatcatctac     360
gactacaccc actactggct cccctccatt gccaccaagc acggtgtctc tcgagcccac     420
ttctccgtca ccaccccctg ggccattgct tacatgggtc ccactgccga tgccatgatc     480
aacggttccg acggccgaac cactcccgag gacttcactg tccctcccaa gtggttcccc     540
ttccccacca aggtctgctg gcgaaagcac gatctcgccc gactcgtccc ctacaaggcc     600
```

```
cccggtatct ccgacggtta ccgaatgggt ctggtcctca agggctgtga ctgcctcctc    660

tctcgaacct accacgagtt cggcacccag tggctccccc tccttgagga gctgcaccag    720

gtccccgttg tccccgtcgg tctgctccct ccctccatcc ccggtgacga gaaggacgag    780

aactgggttt ccatcaagga ctggctcgac aagcaggaga agggctctgt tgtctacgtt    840

gctctcggct ccgaggttct gctcaccgag gaagaggttg ttgagctggc tctcggtctg    900

gagctgtccg gcctcccctt cttctgggcc taccgaaagc ccaagggccc cgccaagtcc    960

gactccgtcg agctgcccga cggtttcgtc gagcgaaccc gagatcgagg tctggtctgg   1020

acctcttggg ctccccagct ccgaatcctc tcccacgagt ccgttggtgg tttcgtcacc   1080

cactgcggtt ccggctccat cgtcgagggt ctgatgttcg gccaccctct catcatgctc   1140

cccatcttcg gtgaccagcc cctcaacgcc cgactgctcg aggataagca ggtcggtatc   1200

gagatccagc gaaacgaaga ggacggctgt ctgaccaagg agtccgtcgc cgagtctctc   1260

cgactcgttg ttgtcgagaa agagggtgag atctaccgag agaaggcccg agagatgtcc   1320

aaggtctact ccgacaccaa gcgtgagaag gagtacgtcg accagttcgt cgactacctc   1380

gagaagaacg cccgagctgt tgccattgac cacgagtct                          1419
```

<210> SEQ ID NO 6
<211> LENGTH: 473
<212> TYPE: PRT
<213> ORGANISM: Artificial sequence
<220> FEATURE:
<223> OTHER INFORMATION: UGT2_3b variant

<400> SEQUENCE: 6

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Leu Leu Leu Ser Arg Ser Tyr
```

```
    210                 215                 220

His Glu Phe Gly Thr Glu Trp Leu Arg Leu Leu Glu Thr Leu His Arg
225                 230                 235                 240

Val Pro Val Val Pro Val Gly Leu Leu Pro Pro Glu Ile Pro Gly Asp
                245                 250                 255

Gly Glu Asp Glu Ser Trp Val Ser Ile Lys Asp Trp Leu Asp Lys Lys
            260                 265                 270

Glu Lys Gly Ser Val Val Tyr Val Ala Leu Gly Ser Glu Val Leu Val
        275                 280                 285

Ser Gln Glu Glu Leu Asn Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
                325                 330                 335

Gly Val Val Trp Thr Ser Trp Ala Pro Gln Leu Arg Ile Leu Ser His
            340                 345                 350

Glu Ser Val Ala Gly Phe Leu Thr His Cys Gly Ser Gly Ser Ile Val
        355                 360                 365

Glu Gly Leu Met Phe Gly His Pro Leu Ile Met Leu Pro Leu Phe Gly
    370                 375                 380

Asp Gln Pro Leu Asn Ala Arg Leu Leu Glu Asp Lys Gln Val Gly Ile
385                 390                 395                 400

Glu Ile Pro Arg Asp Glu Glu Asp Gly Cys Leu Thr Lys Glu Ser Val
                405                 410                 415

Ala Arg Ser Leu Arg Leu Val Met Val Glu Lys Glu Gly Glu Ile Tyr
            420                 425                 430

Arg Glu Lys Ala Arg Glu Met Ser Lys Ile Tyr Asn Asn Thr Glu Val
        435                 440                 445

Glu Asp Gln Tyr Val Ser Gln Phe Val Glu Tyr Leu Glu Lys Asn Ala
    450                 455                 460

Arg Ala Val Ala Ile Asp His Glu Ser
465                 470
```

```
<210> SEQ ID NO 7
<211> LENGTH: 1419
<212> TYPE: DNA
<213> ORGANISM: Artificial sequence
<220> FEATURE:
<223> OTHER INFORMATION: UGT2_3b CpO for S. cerevisiae

<400> SEQUENCE: 7

atggccactt ctgactccat cgttgatgac agaaagaagt tgcacatcgt tatgttccca      60

tggttagctt tcggtcacat tatcccatac ttgcaattgg ctaaattgat tgctgaaaag     120

ggtcacaaag tctctttctt gtccaccacc agaaacatcc aaagattatc ttctcacatt     180

tctccattga tcaacttcgt caagttgact ttaccaagag ttcaagaatt gccagaagat     240

gctgaagcta ccaccgatgt ccatccagaa gatatcccat acttgaagaa ggcttctgat     300

ggtttgcaac cagaagtcac tgaattcttg gaacaacact ctccagactg gattatctac     360

gactacactc actactggtt accatccatt gctactaagc acggtgtttc tcgtgctcat     420

ttctccgtta ccactccatg ggctattgct tacatgggtc caactgctga tgctatgatc     480

aacggttctg atggtagaac cactccagaa gacttcaccg ttccaccaaa atggttccca     540

ttcccaacca aggtctgttg gagaaagcac gatttggcca gattagttcc atacaaggcc     600
```

-continued

```
ccaggtatct ctgacggtta cagaatgggt ttagtcttga agggttctga cttgttgttg     660

tccagatctt accatgaatt cggtactgaa tggttaagat tgttggaaac tttgcacaga     720

gtcccagttg ttccagttgg tttgttgcct cctgaaatcc caggtgacgg tgaagacgaa     780

tcttgggttt ccatcaagga ctggttagat aagaaggaaa agggttccgt tgtctacgtt     840

gctttgggtt ctgaagtctt ggtttctcaa gaagaattga acgaattggc tttgggtttg     900

gaattgtccg gtctaccatt tgtctgggct tacagaaagc caaagggtcc agctaagtct     960

gactctgttg aattgccaga tggtttcgaa gaaagaacca gaggtagagg tgttgtctgg    1020

acttcctggg ctccacaatt gagaattttg tcccacgaat ctgttgctgg tttcttgacc    1080

cactgtggtt ctggttccat tgtcgaaggt ttgatgttcg gtcacccatt gatcatgttg    1140

ccattgttcg gtgaccaacc attgaacgct agattattgg aagacaagca agtcggtatt    1200

gaaatcccaa gagatgaaga agacggttgt ttgaccaagg aatctgttgc ccgttctcta    1260

agattggtta tggtcgaaaa ggaaggtgaa atctacagag aaaaggctag agaaatgtcc    1320

aagatctaca acaacaccga agtcgaagac caatatgtct cccaatttgt tgaatacttg    1380

gaaaagaacg ctcgtgccgt tgccattgac cacgaaagc                           1419
```

<210> SEQ ID NO 8
<211> LENGTH: 1419
<212> TYPE: DNA
<213> ORGANISM: Artificial sequence
<220> FEATURE:
<223> OTHER INFORMATION: UGT2_3b CpO for Y. lipolitica

<400> SEQUENCE: 8

```
atggccacct ccgactccat tgtcgacgac cgaaagaagc tccacattgt catgttcccc      60

tggctcgcct ttggccacat catcccttac ctccagctcg ccaagctcat tgctgagaag     120

ggccacaagg tttccttcct ctccaccacc cgaaacatcc agcgactctc ctcccacatc     180

tctcctctca tcaactttgt caagctcacc ctcccccgag tccaggagct gcccgaggat     240

gctgaggcca ccaccgatgt ccaccccgag gacatcccct acctcaagaa ggcctccgat     300

ggcctccagc ccgaggtcac cgagttcctc gagcagcact ctcccgactg gatcatctac     360

gactacaccc actactggct cccctccatt gccaccaagc acggtgtctc tcgagcccac     420

ttctccgtca ccacccccctg ggccattgcc tacatgggtc ccactgctga cgccatgatc     480

aacggttccg acggccgaac cactcccgag gacttcactg tccctcccaa gtggttcccc     540

ttccccacca aggtctgctg gcgaaagcac gacctcgccc gactcgtccc ctacaaggct     600

cccggtatct ccgacggcta ccgaatgggt ctggtcctca agggctctga tctcctcctc     660

tctcgatctt accacgagtt cggcaccgag tggctccgac tgctcgagac tctccaccga     720

gtccccgttg tccccgtcgg tctgctccct cccgagatcc ccggtgacgg tgaggacgag     780

tcttgggttt ccatcaagga ctggctcgac aagaaggaga agggctccgt tgtctacgtt     840

gctctcggtt ccgaggttct tgtctcccaa gaggagctta acgagctggc tctcggtctg     900

gagctgtccg gtctgccctt tgtctgggcc taccgaaagc ccaagggccc cgccaagtcc     960

gactccgtcg agcttcccga cggtttcgag gagcgaaccc gaggccgagg tgttgtctgg    1020

acctcttggg ctccccagct ccgaatcctc tcccacgagt ccgtcgccgg tttcctcacc    1080

cactgcggtt ccggctccat tgttgagggt ctgatgttcg gccacccccct catcatgctc    1140

cccctcttcg gtgaccagcc cctcaacgcc cgacttctcg aggacaagca ggtcggtatt    1200
```

-continued gagatccccc gagatgaaga ggacggctgt ctgaccaagg agtctgttgc ccgatctctg 1260
cgactcgtca tggtcgagaa ggaaggtgag atctaccgag agaaggcccg agagatgtcc 1320
aagatctaca acaacaccga ggtcgaggac cagtacgttt cccagttcgt cgagtacctt 1380
gagaagaacg cccgagctgt tgccattgac cacgaatca 1419

<210> SEQ ID NO 9
<211> LENGTH: 473
<212> TYPE: PRT
<213> ORGANISM: Artificial sequence
<220> FEATURE:
<223> OTHER INFORMATION: UGT2_4b variant

<400> SEQUENCE: 9

Met Ala Thr Ser Asp Ser Ile Val Asp Asp Arg Lys Lys Leu His Ile
1 5 10 15

Val Met Phe Pro Trp Leu Ala Phe Gly His Ile Ile Pro Tyr Leu Glu
20 25 30

Leu Ser Lys Leu Ile Ala Gln Lys Gly His Lys Val Ser Phe Leu Ser
35 40 45

Thr Thr Lys Asn Ile Asp Arg Leu Ser Ser His Ile Ser Pro Leu Ile
50 55 60

Asn Val Val Gln Leu Thr Leu Pro Arg Val Gln Glu Leu Pro Glu Asp
65 70 75 80

Ala Glu Ala Thr Thr Asp Val His Pro Glu Asp Ile Pro Tyr Leu Lys
85 90 95

Leu Ala Ser Asp Gly Leu Gln Glu Pro Leu Thr Arg Phe Leu Glu Ser
100 105 110

Ser Ser Pro Asp Trp Ile Ile Tyr Asp Tyr Thr His Tyr Trp Leu Pro
115 120 125

Glu Ile Ala Ala Ser Leu Gly Val Ala Arg Ala His Phe Ser Val Thr
130 135 140

Thr Pro Trp Ala Leu Ala Phe Met Gly Pro Ser Ala Asp Ala Met Ile
145 150 155 160

Asn Gly Ser Asp Gly Arg Thr Glu Val Glu Asp Phe Thr Val Pro Pro
165 170 175

Lys Trp Ile Pro Phe Pro Thr Thr Val Ala Trp Arg Lys His Asp Leu
180 185 190

Ala Arg Leu Val Pro Tyr Lys Ala Pro Gly Ile Ser Asp Gly Tyr Arg
195 200 205

Met Gly Leu Val Leu Lys Gly Cys Asp Cys Leu Leu Ser Arg Thr Tyr
210 215 220

His Glu Phe Gly Thr Gln Trp Leu Pro Leu Leu Glu Glu Leu His Gln
225 230 235 240

Val Pro Val Val Pro Val Gly Leu Leu Pro Pro Ser Ile Pro Gly Asp
245 250 255

Glu Lys Asp Glu Asn Trp Val Ser Ile Lys Asp Trp Leu Asp Lys Gln
260 265 270

Glu Lys Gly Ser Val Val Tyr Val Ala Leu Gly Ser Glu Val Leu Leu
275 280 285

Thr Glu Glu Glu Val Val Glu Leu Ala Leu Gly Leu Glu Leu Ser Gly
290 295 300

Leu Pro Phe Phe Trp Ala Tyr Arg Lys Pro Lys Gly Pro Ala Lys Ser
305 310 315 320

Asp Ser Val Glu Leu Pro Asp Gly Phe Val Glu Arg Thr Arg Asp Arg

-continued

```
                325                 330                 335

Gly Leu Val Trp Thr Ser Trp Ala Pro Gln Leu Arg Ile Leu Ser His
            340                 345                 350

Glu Ser Val Ala Gly Phe Leu Thr His Cys Gly Ser Gly Ser Ile Val
        355                 360                 365

Glu Gly Leu Met Phe Gly His Pro Leu Ile Met Leu Pro Leu Phe Gly
    370                 375                 380

Asp Gln Pro Leu Asn Ala Arg Leu Leu Glu Asp Lys Gln Val Gly Ile
385                 390                 395                 400

Glu Ile Pro Arg Asp Glu Glu Asp Gly Cys Leu Thr Lys Glu Ser Val
                405                 410                 415

Ala Arg Ser Leu Arg Leu Val Met Val Glu Lys Glu Gly Glu Ile Tyr
            420                 425                 430

Arg Glu Lys Ala Arg Glu Met Ser Lys Ile Tyr Asn Asn Thr Glu Val
        435                 440                 445

Glu Asp Gln Tyr Val Ser Gln Phe Val Glu Tyr Leu Glu Lys Asn Ala
    450                 455                 460

Arg Ala Val Ala Ile Asp His Glu Ser
465                 470


<210> SEQ ID NO 10
<211> LENGTH: 1419
<212> TYPE: DNA
<213> ORGANISM: Artificial sequence
<220> FEATURE:
<223> OTHER INFORMATION: UGT2_4b CpO for S. cerevisiae

<400> SEQUENCE: 10

atggccactt ctgactccat cgttgatgac agaaagaagt tgcacatcgt tatgttccca     60

tggttagctt tcggtcacat tatcccatac ttggaattgt ccaaattgat tgctcaaaag    120

ggtcacaaag tctctttctt gtccaccacc aagaacatcg acagattatc ttctcacatt    180

tctccattga tcaacgttgt ccaattgact ttaccaagag ttcaagaatt gccagaagat    240

gctgaagcta ccaccgatgt ccatccagaa gatatcccat acttgaagtt ggcttctgat    300

ggtttgcaag aaccattgac tagattcttg gaatcttctt ctccagactg gattatctac    360

gactacactc actactggtt accagaaatt gctgcctctt tgggtgttgc tcgtgctcat    420

ttctccgtta ccactccatg ggctttggct ttcatgggtc catctgctga tgctatgatc    480

aacggttctg atggtagaac cgaagtcgaa gacttcaccg ttccaccaaa atggatccca    540

ttcccaacca ctgtcgcttg gagaaagcac gatttggcca gattagttcc atacaaggcc    600

ccaggtatct ctgacggtta cagaatgggt ttagtcttga agggttgtga ctgtttgttg    660

tccagaactt accatgaatt cggtactcaa tggttacctt tgttggaaga attgcaccaa    720

gtcccagttg ttccagttgg tttgttgcct ccttctatcc caggtgacga aaaggacgaa    780

aactgggttt ccatcaagga ctggttagat aagcaagaaa agggttccgt tgtctacgtt    840

gctttgggtt ctgaagtctt gttgactgaa gaagaagttg ttgaattggc tttgggtttg    900

gaattgtccg gtctaccatt tttctgggct tacagaaagc caaagggtcc agctaagtct    960

gactctgttg aattgccaga tggtttcgtc gaaagaacca gagacagagg tttggtctgg   1020

acttcctggg ctccacaatt gagaattttg tcccacgaat ctgttgctgg tttcttgacc   1080

cactgtggtt ctggttccat tgtcgaaggt ttgatgttcg gtcacccatt gatcatgttg   1140

ccattgttcg gtgaccaacc attgaacgct agattattgg aagacaagca agtcggtatt   1200
```

```
gaaatcccaa gagatgaaga agacggttgt ttgaccaagg aatctgttgc ccgttctcta   1260

agattggtta tggtcgaaaa ggaaggtgaa atctacagag aaaaggctag agaaatgtcc   1320

aagatctaca acaacaccga agtcgaagac caatatgtct cccaatttgt tgaatacttg   1380

gaaaagaacg ctcgtgccgt tgccattgac cacgaaagc                          1419
```

<210> SEQ ID NO 11
<211> LENGTH: 473
<212> TYPE: PRT
<213> ORGANISM: Artificial sequence
<220> FEATURE:
<223> OTHER INFORMATION: UGT2_5b variant

<400> SEQUENCE: 11

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Leu Leu Leu Ser Arg Ser Tyr
    210                 215                 220

His Glu Phe Gly Thr Glu Trp Leu Arg Leu Leu Glu Thr Leu His Arg
225                 230                 235                 240

Val Pro Val Val Pro Val Gly Leu Leu Pro Pro Glu Ile Pro Gly Asp
                245                 250                 255

Gly Glu Asp Glu Ser Trp Val Ser Ile Lys Asp Trp Leu Asp Lys Lys
            260                 265                 270

Glu Lys Gly Ser Val Val Tyr Val Ala Leu Gly Ser Glu Val Leu Val
        275                 280                 285

Ser Gln Glu Glu Leu Asn Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
```

-continued

```
                325                 330                 335

Gly Val Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Glu Ser Leu Arg Leu Val Val Val Glu Lys Glu Gly Glu Ile Tyr
            420                 425                 430

Arg Glu Lys Ala Arg Glu Met Ser Lys Val Tyr Ser Asp Thr Lys Arg
        435                 440                 445

Glu Lys Glu Tyr Val Asp Gln Phe Val Asp Tyr Leu Glu Lys Asn Ala
    450                 455                 460

Arg Ala Val Ala Ile Asp His Glu Ser
465                 470


<210> SEQ ID NO 12
<211> LENGTH: 1419
<212> TYPE: DNA
<213> ORGANISM: Artificial sequence
<220> FEATURE:
<223> OTHER INFORMATION: UGT2_5b CpO for S. cerevisiae

<400> SEQUENCE: 12

atggccactt ctgactccat cgttgatgac agaaagaagt tgcacatcgt tatgttccca     60

tggttagctt tcggtcacat tatcccatac ttggaattgt ccaaattgat tgctcaaaag    120

ggtcacaaag tctctttctt gtccaccacc aagaacatcg acagattatc ttctcacatt    180

tctccattga tcaacgttgt ccaattgact ttaccaagag ttcaagaatt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accatccatt gctactaagc acggtgtttc tcgtgctcat    420

ttctccgtta ccactccatg ggctattgct tacatgggtc caactgctga tgctatgatc    480

aacggttctg atggtagaac cactccagaa gacttcaccg ttccaccaaa atggttccca    540

ttcccaacca aggtctgttg gagaaagcac gatttggcca gattagttcc atacaaggcc    600

ccaggtatct ctgacggtta cagaatgggt ttagtcttga agggttctga cttgttgttg    660

tccagatctt accatgaatt cggtactgaa tggttaagat tgttggaaac tttgcacaga    720

gtcccagttg ttccagttgg tttgttgcct cctgaaatcc caggtgacgg tgaagacgaa    780

tcttgggttt ccatcaagga ctggttagat aagaaggaaa agggttccgt tgtctacgtt    840

gctttgggtt ctgaagtctt ggtttctcaa gaagaattga acgaattggc tttgggtttg    900

gaattgtccg gtctaccatt tgtctgggct tacagaaagc caaagggtcc agctaagtct    960

gactctgttg aattgccaga tggtttcgaa gaaagaacca gaggtagagg tgttgtctgg   1020

acttcctggg ctccacaatt gagaattttg tcccacgaat ctgttggtgg tttcgttacc   1080

cactgtggtt ctggttccat tgtcgaaggt ttgatgttcg gtcacccatt gatcatgttg   1140

ccaatcttcg gtgaccaacc attgaacgct agattattgg aagacaagca agtcggtatt   1200
```

-continued gaaatcccaa gaaacgaaga agacggttgt ttgaccaagg aatctgttgc cgaatctcta 1260
agattggttg ttgtcgaaaa ggaaggtgaa atctacagag aaaaggctag agaaatgtcc 1320
aaggtttact ctgataccaa gagagaaaag gaatatgtcg accaatttgt tgactacttg 1380
gaaaagaacg ctcgtgccgt tgccattgac cacgaaagc 1419

<210> SEQ ID NO 13
<211> LENGTH: 1419
<212> TYPE: DNA
<213> ORGANISM: Artificial sequence
<220> FEATURE:
<223> OTHER INFORMATION: UGT2_5b CpO for Y. lipolitica

<400> SEQUENCE: 13
atggccacct ccgactccat tgtcgacgac cgaaagaagc tccacattgt catgttcccc 60
tggctcgcct tcggccacat catcccttac ctggagctgt ccaagctcat tgcccagaag 120
ggccacaagg tttctttcct ctccaccacc aagaacattg accgactctc ctcccacatc 180
tctcctctca tcaacgttgt ccagctcacc ctcccccgag tccaggagct tcccgaggat 240
gctgaggcca ccaccgacgt ccacccccgag gacatcccct acctcaagaa ggcctccgat 300
ggcctccagc ccgaggtcac cgagttcctc gagcagcact cccccgactg gatcatctac 360
gactacaccc actactggct cccctccatt gccaccaagc acggtgtctc tcgagcccac 420
ttctccgtca ccaccccctg ggccattgcc tacatgggtc ccactgccga cgccatgatc 480
aacggttccg acggccgaac caccccccgag gatttcactg tccctcccaa gtggttcccc 540
ttccccacca aggtctgctg gcgaaagcac gacctcgctc gactcgtccc ctacaaggcc 600
cccggtatct ccgacggtta ccgaatgggt ctggttctca agggctccga tctcctcctc 660
tctcgatctt accacgagtt tggtactgag tggctccgac tgctcgagac tctccaccga 720
gtccccgttg tccccgtcgg cctcctccct cccgagatcc ccggtgatgg tgaggacgag 780
tcttgggttt ccatcaagga ctggctcgac aagaaggaga agggctctgt tgtctacgtt 840
gctctcggtt ccgaggtcct tgtctctcaa gaggagctta acgagcttgc tctgggcctc 900
gagctgtccg gcctcccctt cgtctgggcc taccgaaagc ccaagggtcc cgccaagtcc 960
gactccgtcg agctgcccga cggtttcgag gagcgaaccc gaggccgagg tgttgtctgg 1020
acctcttggg ctccccagct ccgaatcctc tcccacgagt ccgtcggtgg ctttgtcacc 1080
cactgcggtt ccggctccat cgtcgagggt ctgatgtttg gccacccccct catcatgctc 1140 cccatcttcg gtgaccagcc cctcaacgcc cgactccttg aggacaagca ggtcggtatt 1200
gagatccccc gaaacgagga agatggttgt ctgaccaagg agtctgttgc tgagtctctg 1260
cgactcgttg ttgtcgagaa agagggtgag atctaccggg agaaggcccg agagatgtcc 1320
aaggtctact ccgacaccaa gcgagagaag gagtacgtcg accagttcgt cgactacctc 1380
gagaagaacg cccgagctgt tgccattgac cacgaatcc 1419

<210> SEQ ID NO 14
<211> LENGTH: 473
<212> TYPE: PRT
<213> ORGANISM: Artificial sequence
<220> FEATURE:
<223> OTHER INFORMATION: UGT2_6b variant

<400> SEQUENCE: 14

Met Ala Thr Ser Asp Ser Ile Val Asp Asp Arg Lys Lys Leu His Ile
1 5 10 15

-continued

```
Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240

Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Asp Glu Val Val Glu Leu Ala His Gly Leu Glu Leu Ser Gly
    290                 295                 300

Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
```

```
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470


<210> SEQ ID NO 15
<211> LENGTH: 1419
<212> TYPE: DNA
<213> ORGANISM: Artificial sequence
<220> FEATURE:
<223> OTHER INFORMATION: UGT2_6b CpO for S. cerevisiae

<400> SEQUENCE: 15

atggccactt ctgactccat cgttgatgac agaaagaagt tgcacatcgt tatgttccca     60

tggttagctt tcggtcacat tatcccatac ttggaattgt ccaaattgat tgctcaaaag    120

ggtcacaaag tctctttctt gtccaccacc aagaacatcg acagattatc ttctcacatt    180

tctccattga tcaacgttgt ccaattgact ttaccaagag ttcaagaatt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accatccatt gctactaagc acggtgtttc tcgtgctcat    420

ttctccgtta ccactccatg ggctattgct tacatgggtc caactgctga tgctatgatc    480

aacggttctg atggtagaac cactccagaa gacttcaccg ttccaccaaa atggttccca    540

ttcccaacca aggtctgttg gagaaagcac gatttggcca gattagttcc atacaaggcc    600

ccaggtatct ctgacggtta cagaatgggt ttagtcatca agggttgtga ctgtttgttg    660

tccaagactt accatgaatt cggtactcaa tggttaagat tgttggaaac tttgcacaga    720

aagccagtta tcccagttgg tttgttgcct ccttctatcc caggttctga caaggacgac    780

tcttgggttt ccatcaagga atggttagat ggtcaagaaa agggttccgt tgtctacgtt    840

gctttgggtt ctgaagtctt ggttactcaa gacgaagttg ttgaattggc tcacggtttg    900

gaattgtccg gtctaccatt tgtctgggct tacagaaacc caaagggtcc agctaagtct    960

gactctgttg aattgccaga tggtttcgtc gaaagagtta gagacagagg tttggtctgg   1020

acttcctggg ctccacaatt gagaattttg tcccacgaat ctgtttgtgg tttcttgact   1080

cactgtggtt ctggttctat cgtcgaaggt ttgatgttcg gtcatccttt gatcatgttg   1140

cctatctttg gtgaccaacc attgaacgct agattgttgg aagacaagca agttggtatt   1200

gaaattccaa gaaacgaaga agatggttct ttcaccagag actctgttgc tgaatctttg   1260

agattagtca tggttgaaga agaaggtaag atctacagag aaaaggccaa ggaaatgtcc   1320

aagttgtttg gtgacaaaga tttgcaagac caatacgtcg atgacttcgt cgaatacttg   1380

caaaagcacc gtcgtgccgt tgccattgac cacgaatca                          1419


<210> SEQ ID NO 16
<211> LENGTH: 1419
<212> TYPE: DNA
<213> ORGANISM: Artificial sequence
<220> FEATURE:
<223> OTHER INFORMATION: UGT2_6b CpO for Y. lipolitica

<400> SEQUENCE: 16

atggctactt ccgactccat tgtcgacgac cgaaagaagc tccacattgt catgttcccc     60

tggctcgcct ttggccacat cattccctac ctcgagcttt ccaagctcat tgcccagaag    120
```

```
ggccacaagg tttctttcct ctccaccacc aagaacattg accgactctc ctcccacatc    180

tctcctctca tcaacgttgt ccagctcacc ctcccccgag tccaggagct gcccgaggac    240

gccgaggcca ccaccgatgt ccaccccgag gatatcccct acctcaagaa ggcctccgac    300

ggtctgcagc ccgaggtcac cgagttcctc gagcagcact ctcccgactg gatcatctac    360

gactacaccc actactggct cccctccatt gccaccaagc acggtgtctc tcgagcccac    420

ttctccgtca ccaccccctg ggccattgcc tacatgggcc ccactgctga cgccatgatc    480

aacggttccg atggccgaac cacccccgag gacttcactg tccctcccaa gtggttcccc    540

ttccccacca aggtctgctg gcgaaagcac gatctggccc gactcgttcc ctacaaggcc    600

cccggtatct ccgacggcta ccgaatgggt ctggtcatca agggctgcga ctgtctgctc    660

tccaagacct accacgagtt tggcacccag tggctccgac tcctcgagac tctccaccga    720

aagcccgtca tccccgtcgg tctgctccct ccctccatcc ccggctccga caaggacgac    780

tcttgggttt ccatcaagga gtggctcgac ggccaggaga agggctctgt tgtctacgtt    840

gctctcggtt ccgaggttct cgtcacccag gacgaggttg ttgagctggc ccacggtctg    900

gagctgtccg gcctcccctt cgtctgggct taccgaaacc ccaagggtcc cgccaagtcc    960

gactccgtcg agcttcccga tggtttcgtc gagcgagtcc gagatcgagg tctggtctgg   1020

acctcttggg ctccccagct ccgaatcctc tcccacgagt ccgtctgtgg tttcctcacc   1080

cactgcggtt ccggctccat cgtcgagggt ctgatgttcg gccacccccct catcatgctc   1140

cccatcttcg gtgaccagcc cctcaacgcc cgactccttg aggacaagca ggtcggtatc   1200

gagatccccc gaaacgaaga ggacggttcc ttcacccgag actctgttgc tgagtctctc   1260

cgactcgtca tggtcgagga agagggtaag atctaccgag agaaggccaa ggagatgtcc   1320

aagctgttcg gtgacaagga tctccaggac cagtacgtcg acgactttgt cgagtacctc   1380

cagaagcacc gacgagctgt tgccattgac cacgagtct                          1419
```

```
<210> SEQ ID NO 17
<211> LENGTH: 473
<212> TYPE: PRT
<213> ORGANISM: Artificial sequence
<220> FEATURE:
<223> OTHER INFORMATION: UGT2_7b variant

<400> SEQUENCE: 17

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125
```

-continued

```
Glu Ile Ala Lys Ser Leu Gly Val Ser Arg Ala His Phe Ser Val Thr
    130                 135                 140

Thr Pro Trp Ala Ile Ala Tyr Ile Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240

Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Asp Glu Val Val Glu Leu Ala His Gly Leu Glu Leu Ser Gly
    290                 295                 300

Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470
```

<210> SEQ ID NO 18
<211> LENGTH: 1419
<212> TYPE: DNA
<213> ORGANISM: Artificial sequence
<220> FEATURE:
<223> OTHER INFORMATION: UGT2_7b CpO for S. cerevisiae

<400> SEQUENCE: 18

```
atggccactt ctgactccat cgttgatgac agaaagaagt tgcacatcgt tatgttccca     60

tggttagctt tcggtcacat tatcccatac ttggaattgt ccaaattgat tgctcaaaag    120
```

-continued

```
ggtcacaaag tctctttctt gtccaccacc aagaacatcg acagattatc ttctcacatt    180

tctccattga tcaacgttgt ccaattgact ttaccaagag ttcaagaatt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accagaaatt gctaagtctt tgggtgtttc tcgtgctcat    420

ttctccgtta ccactccatg ggctattgct tacattggtc caactgctga tgctatgatc    480

aacggttctg attacagaac cgaattggaa gacttcaccg ttccaccaaa atggttccca    540

ttcccaacca ctgtctgttg gagaaagcac gatttggcca gattagttcc atacaaggcc    600

ccaggtatct ctgacggtta cagaatgggt ttagtcatca agggttgtga ctgtttgttg    660

tccaagactt accatgaatt cggtactcaa tggttaagat tgttggaaac tttgcacaga    720

aagccagtta tcccagttgg tttgttgcct ccttctatcc caggttctga caaggacgac    780

tcttgggttt ccatcaagga atggttagat ggtcaagaaa agggttccgt tgtctacgtt    840

gctttgggtt ctgaagtctt ggttactcaa gacgaagttg ttgaattggc tcacggtttg    900

gaattgtccg gtctaccatt tgtctgggct tacagaaacc caaagggtcc agctaagtct    960

gactctgttg aattgccaga tggtttcgtc gaaagagtta gagacagagg tttggtctgg   1020

acttcctggg ctccacaatt gagaattttg tcccacgaat ctgtttgtgg tttcttgact   1080

cactgtggtt ctggttctat cgtcgaaggt ttgatgttcg gtcatccttt gatcatgttg   1140

cctatctttg gtgaccaacc attgaacgct agattgttgg aagacaagca agttggtatt   1200

gaaattccaa gaaacgaaga agatggttct ttcaccagag actctgttgc tgaatctttg   1260

agattagtca tggttgaaga agaaggtaag atctacagag aaaaggccaa ggaaatgtcc   1320

aagttgtttg gtgacaaaga tttgcaagac caatacgtcg atgacttcgt cgaatacttg   1380

caaaagcacc gtcgtgccgt tgccattgac cacgaatca                          1419
```

<210> SEQ ID NO 19
<211> LENGTH: 1419
<212> TYPE: DNA
<213> ORGANISM: Artificial sequence
<220> FEATURE:
<223> OTHER INFORMATION: UGT2_7b CpO for Y. lipolitica

<400> SEQUENCE: 19

```
atggccacct ccgactccat tgttgacgac cgaaagaagc tccacattgt catgttcccc     60

tggctcgcct tcggccacat cattccctac ctcgagcttt ccaagctcat tgcccagaag    120

ggccacaagg tttctttcct ctccaccacc aagaacattg accgactctc ctcccacatc    180

tctcctctca tcaacgttgt ccagctcacc ctcccccgag tccaggagct gcccgaggat    240

gctgaggcca ccaccgacgt ccaccccgag gatatcccct acctcaagaa ggcctccgat    300

ggtctgcagc ccgaggtcac cgagttcctc gagcagcact ctcccgactg gatcatctac    360

gactacaccc actactggct ccccgagatt gccaagtctc tcggtgtctc tcgagcccac    420

ttctccgtca ccaccccctg ggccattgct tacatcggtc ccactgctga cgccatgatc    480

aacggctccg actaccgaac tgaactcgag gacttcactg ttcctcccaa gtggttcccc    540

ttccccacca ccgtctgctg gcgaaagcac gatctcgccc gactggtccc ctacaaggct    600

cccggtatct ccgacggcta ccgaatgggt ctggtcatca agggttgcga ctgtctgctc    660

tccaagacct accacgagtt tggcacccag tggctgcgac tcctcgagac tctccaccga    720
```

```
aagcccgtca tccccgtcgg tctgctgccc ccttccatcc ccggttccga caaggacgac    780

tcttgggttt ccatcaagga gtggctcgac ggccaggaga agggctctgt tgtctacgtt    840

gctctcggct ccgaggttct cgtcacccag gacgaggttg tcgagctggc ccacggtctg    900

gagctgtccg gtctgccctt cgtctgggcc taccgaaacc ccaagggccc cgccaagtcc    960

gactccgtcg agcttcccga tggtttcgtc gagcgagtcc gagatcgagg tctggtctgg   1020

acctcttggg ctccccagct ccgaatcctc tcccacgagt ccgtctgcgg tttcctcacc   1080

cactgtggtt ccggctccat tgtcgagggt ctgatgttcg gccacccccct catcatgctc  1140

cccatcttcg gtgaccagcc cctcaacgcc cgactccttg aggacaagca ggtcggtatc   1200

gagatccccc gaaacgaaga ggacggctct ttcacccgag actccgttgc cgagtctctc   1260

cgactcgtca tggtcgagga agagggtaag atctaccgag agaaggccaa ggagatgtcc   1320

aagctctttg gtgacaagga tctccaggac cagtacgtcg acgactttgt cgagtacctc   1380

cagaagcacc gacgagctgt tgccatcgac cacgagtcg                          1419


<210> SEQ ID NO 20
<211> LENGTH: 473
<212> TYPE: PRT
<213> ORGANISM: Artificial sequence
<220> FEATURE:
<223> OTHER INFORMATION: UGT2_8b

<400> SEQUENCE: 20

Met Ala Thr Ser Asp Ser Ile Val Asp Asp Arg Lys Gln Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Glu Lys Gly His Lys Val Ser Phe Leu Ser
        35                  40                  45

Thr Pro Lys Asn Ile Gln Arg Leu Ser Ser His Leu Ser Pro Leu Ile
    50                  55                  60

Asn Val Val Gln Leu Pro Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240
```

-continued

```
Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Asp Glu Val Val Glu Leu Ala His Gly Leu Glu Leu Ser Gly
    290                 295                 300

Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470


<210> SEQ ID NO 21
<211> LENGTH: 1419
<212> TYPE: DNA
<213> ORGANISM: Artificial sequence
<220> FEATURE:
<223> OTHER INFORMATION: UGT_8b CpO for S. cerevisiae

<400> SEQUENCE: 21

atggccactt ctgactccat cgttgatgac agaaagcaat tgcacatcgt tatgttccca     60

tggttagctt tcggtcacat tatcccatac ttggaattgt ccaaattgat tgctgaaaag    120

ggtcacaaag tctctttctt gtccacccca aagaacatcc aaagattatc ttctcacttg    180

tctccattga tcaacgttgt ccaattgcca ttaccaagag ttcaagaatt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accatccatt gctactaagc acggtgtttc tcgtgctcat    420

ttctccgtta ccactccatg ggctattgct tacatgggtc caactgctga tgctatgatc    480

aacggttctg atggtagaac cactccagaa gacttcaccg ttccaccaaa atggttccca    540

ttcccaacca aggtctgttg gagaaagcac gatttggcca gattagttcc atacaaggcc    600

ccaggtatct ctgacggtta cagaatgggt ttagtcatca agggttgtga ctgtttgttg    660

tccaagactt accatgaatt cggtactcaa tggttaagat tgttggaaac tttgcacaga    720
```

```
aagccagtta tcccagttgg tttgttgcct ccttctatcc caggttctga caaggacgac    780

tcttgggttt ccatcaagga atggttagat ggtcaagaaa agggttccgt tgtctacgtt    840

gctttgggtt ctgaagtctt ggttactcaa gacgaagttg ttgaattggc tcacggtttg    900

gaattgtccg gtctaccatt tgtctgggct tacagaaacc caaagggtcc agctaagtct    960

gactctgttg aattgccaga tggtttcgtc gaaagagtta gagacagagg tttggtctgg   1020

acttcctggg ctccacaatt gagaattttg tcccacgaat ctgtttgtgg tttcttgact   1080

cactgtggtt ctggttctat cgtcgaaggt ttgatgttcg gtcatccttt gatcatgttg   1140

cctatctttg gtgaccaacc attgaacgct agattgttgg aagacaagca agttggtatt   1200

gaaattccaa gaaacgaaga agatggttct ttcaccagag actctgttgc tgaatctttg   1260

agattagtca tggttgaaga agaaggtaag atctacagag aaaaggccaa ggaaatgtcc   1320

aagttgtttg gtgacaaaga tttgcaagac caatacgtcg atgacttcgt cgaatacttg   1380

caaaagcacc gtcgtgccgt tgccattgac cacgaatca                          1419


<210> SEQ ID NO 22
<211> LENGTH: 473
<212> TYPE: PRT
<213> ORGANISM: Artificial sequence
<220> FEATURE:
<223> OTHER INFORMATION: UGT2_9b variant

<400> SEQUENCE: 22

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ser Lys Leu Leu Ala Gln Lys Gly His Lys Val Ser Phe Ile Ser
        35                  40                  45

Thr Pro Arg Asn Ile Gln Arg Leu Ser Ser His Ile Ser Pro Leu Ile
    50                  55                  60

Asn Leu Val Gln Leu Pro Leu Pro Arg Val Asp Asn Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Glu Ile Ala Lys Ser Leu Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Leu Leu Leu Ser Arg Ser Tyr
    210                 215                 220

His Glu Phe Gly Thr Glu Trp Leu Arg Leu Leu Glu Thr Leu His Arg
225                 230                 235                 240
```

-continued

```
Val Pro Val Val Pro Val Gly Leu Leu Pro Pro Glu Ile Pro Gly Asp
            245                 250                 255

Gly Glu Asp Glu Ser Trp Val Ser Ile Lys Asp Trp Leu Asp Lys Lys
            260                 265                 270

Glu Lys Gly Ser Val Val Tyr Val Ala Leu Gly Ser Glu Val Leu Val
        275                 280                 285

Ser Gln Glu Glu Leu Asn Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
                325                 330                 335

Gly Val Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Leu Thr Lys Glu Ser Val
                405                 410                 415

Ala Arg Ser Leu Arg Ser Val Val Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470
```

<210> SEQ ID NO 23
<211> LENGTH: 1419
<212> TYPE: DNA
<213> ORGANISM: Artificial sequence
<220> FEATURE:
<223> OTHER INFORMATION: UGT2_9b CpO for S.cerevisiae

<400> SEQUENCE: 23

```
atggccactt ctgactccat cgttgatgac agaaagaagt tgcacatcgt tatgttccca     60

tggttagctt tcggtcacat tatcccatac ttgcaattgt ccaaattgtt ggctcaaaag    120

ggtcacaaag tctctttcat ctccacccca agaaacatcc aaagattatc ttctcacatt    180

tctccattga tcaacttggt ccaattgcca ttaccaagag ttgacaactt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accagaaatt gctaagtctt tgggtgtttc tcgtgctcat    420

ttctccgtta ccactccatg ggctattgct tacatgggtc caactgctga tgctatgatc    480

aacggttctg attacagaac cgaattggaa gacttcaccg ttccaccaaa atggttccca    540

ttcccaacca ctgtctgttg gagaaagcac gatttggcca gattagttcc atacaaggcc    600

ccaggtatct ctgacggtta cagaatgggt ttagtcttga agggttctga cttgttgttg    660

tccagatctt accatgaatt cggtactgaa tggttaagat tgttggaaac tttgcacaga    720
```

-continued

```
gtcccagttg ttccagttgg tttgttgcct cctgaaatcc caggtgacgg tgaagacgaa    780

tcttgggttt ccatcaagga ctggttagat aagaaggaaa agggttccgt tgtctacgtt    840

gctttgggtt ctgaagtctt ggtttctcaa gaagaattga acgaattggc tttgggtttg    900

gaattgtccg gtctaccatt tgtctgggct tacagaaagc caaagggtcc agctaagtct    960

gactctgttg aattgccaga tggtttcgaa gaaagaacca gaggtagagg tgttgtctgg   1020

acttcctggg ctccacaatt gagaattttg tcccacgaat ctgtttgtgg tttcttgact   1080

cactgtggtt ctggttccat tgtcgaaggt ttgatgttcg gtcatccatt gatcatgttg   1140

ccaatctttg gtgaccaacc tttgaacgcc agattattgg aagacaagca agttggtatt   1200

gaaattccaa gaaacgaaga agacggttct ttgaccaagg aatctgttgc cagatctttg   1260

agatctgttg ttgtcgaaga agaaggtaag atctacagag aaaaggccaa ggaaatgtcc   1320

aaattgtttg gtgacaagga tttgcaagat caatatgtcg atgacttcgt cgaatactta   1380

caaaagcacc gtcgtgctgt tgccattgac catgaaagc                          1419
```

```
<210> SEQ ID NO 24
<211> LENGTH: 1419
<212> TYPE: DNA
<213> ORGANISM: Artificial sequence
<220> FEATURE:
<223> OTHER INFORMATION: UGT2_9b CpO for Y. lipolitica

<400> SEQUENCE: 24

atggccacct ccgactccat tgtcgacgac cgaaagaagc tccacattgt catgttcccc     60

tggctcgcct ttggccacat cattccctac ctccagctct ccaagctcct cgcccagaag    120

ggccacaagg tttctttcat ctccactccc cgaaacatcc agcgactctc ctcccacatc    180

tctcctctca tcaacctcgt ccagctcccc ctcccccgag tcgacaacct ccccgaggat    240

gctgaggcca ccaccgatgt ccaccccgag gacatcccct acctcaagaa ggcctccgac    300

ggcctccagc ccgaggtcac cgagttcctc gagcagcact cccccgactg gatcatctac    360

gactacaccc actactggct ccccgagatt gccaagtctc tcggtgtctc tcgagcccac    420

ttctccgtca ccacccccctg ggccattgct tacatgggtc ccactgccga tgccatgatc    480

aacggctccg actaccgaac cgagcttgag gacttcaccg tccctcccaa gtggttcccc    540

ttccccacca ccgtctgctg gcgaaagcac gatctcgccc gactcgtccc ctacaaggct    600

cccggtatct ccgacggtta ccgaatgggc ctcgttctca agggttccga tctgctgctc    660

tcccgatctt accacgagtt tggtactgag tggctgcgac tcctcgagac tctgcaccga    720

gtccccgttg tccccgtcgg tctgctccct cccgagatcc ccggtgacgg tgaggacgag    780

tcttgggttt ccatcaagga ctggctcgac aagaaggaga agggctccgt cgtctacgtt    840

gccctcggct ccgaggttct cgtttcccaa gaggagctta acgagcttgc tctcggcctc    900

gagctgtccg gtctgccctt tgtctgggcc taccgaaagc ccaagggccc cgccaagtcc    960

gactccgtcg agctgcccga cggcttcgag gagcgaaccc gaggtcgagg tgttgtctgg   1020

acctcttggg ctccccagct ccgaatcctc tcccacgagt ccgtctgtgg tttcctgacc   1080

cactgcggtt ccggctctat cgtcgagggt ctgatgttcg gccacccccct catcatgctc   1140

cccatcttcg gtgaccagcc cctcaacgcc cgacttctcg aggacaagca ggtcggtatt   1200

gagatccccc gaaacgaaga ggacggctct ctcaccaagg agtctgttgc tcgatctctg   1260

cgatccgtcg ttgtcgagga agagggtaag atctaccgag agaaggccaa ggagatgtcc   1320

aagctgttcg gtgacaagga tctgcaggac cagtacgtcg acgacttcgt cgagtacctc   1380
```

```
cagaagcacc gacgagctgt tgccattgac cacgaatcc                        1419


<210> SEQ ID NO 25
<211> LENGTH: 473
<212> TYPE: PRT
<213> ORGANISM: Artificial sequence
<220> FEATURE:
<223> OTHER INFORMATION: UGT2_10b variant

<400> SEQUENCE: 25

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Glu Ile Ala Lys Ser Leu Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Glu Leu His Arg
225                 230                 235                 240

Val Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Glu Glu Val Val Glu Leu Ala His Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350
```

-continued

```
Glu Ser Val Ala Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470


<210> SEQ ID NO 26
<211> LENGTH: 1419
<212> TYPE: DNA
<213> ORGANISM: Artificial sequence
<220> FEATURE:
<223> OTHER INFORMATION: UGT2_10b CpO for Y. lipolitica

<400> SEQUENCE: 26

atggccacct ccgactccat tgttgacgac cgaaagaagc tccacattgt catgttcccc     60

tggctcgcct ttggccacat catcccctat ctcgagcttt ccaagctcat tgcccagaag    120

ggccacaagg tttccttcct ctccaccacc aagaacattg accgactctc ctcccacatc    180

tctcccctca tcaactttgt caagctcacc ctcccccgag tccaggagct gcccgaggac    240

gccgaggcca ccactgatgt ccaccccgag gatatcccct acctcaagaa ggcctccgac    300

ggcctccagc ccgaggtcac tgagttcctc gagcagcact ctcccgactg gatcatctac    360

gactacaccc actactggct ccccgagatt gccaagtctc tcggtgtctc tcgagcccac    420

ttctccgtca ccaccccctg ggccattgct tacatgggtc ccactgccga tgccatgatc    480

aacggttccg actaccgaac cgagcttgag gacttcaccg tccctcccaa gtggttcccc    540

ttccccacca ccgtctgctg gcgaaagcac gatctggccc gactcgtccc ctacaaggct    600

cccggtatct ccgacggtta ccgaatgggc ctcgtcatca agggctgcga ctgtctgctc    660

tccaagacct accacgagtt cggtactcag tggctccgac ttctcgagga gctgcaccga    720

gtccccgtca tccccgttgg tctgctccct ccctccatcc ccggctctga caaggacgac    780

tcttgggttt ccatcaagga gtggctcgac ggccaggaga agggctccgt tgtctacgtt    840

gctctcggtt ccgaggttct cgtcacccag gaagaggttg tcgagcttgc tcacggtctg    900

gagctgtccg gtctgccctt cttctgggcc taccgaaagc ccaagggtcc cgccaagtcc    960

gactccgtcg agcttcccga tggtttcgtc gagcgagtcc gagatcgagg tctggtctgg   1020

acctcttggg ctccccagct ccgaatcctc tcccacgagt ccgttgctgg tttcctcacc   1080

cactgcggtt ccggctccat tgtcgagggc ctcatgttcg gccaccctct catcatgctc   1140

cccatcttcg gtgaccagcc cctcaacgcc cgactccttg aggacaagca ggtcggtatc   1200

gagatccccc gaaacgagga agatggttct ttcacccgag actctgttgc cgagtctctg   1260

cgactcgtca tggtcgagga agagggtaag atctaccgag agaaggccaa ggagatgtcc   1320

aagctctttg gcgacaagga cctccaggac cagtacgtcg acgactttgt cgagtacctc   1380
```

-continued

```
cagaagcacc gacgagctgt tgccattgac cacgaaagc                    1419


<210> SEQ ID NO 27
<211> LENGTH: 473
<212> TYPE: PRT
<213> ORGANISM: Stevia rebaudiana

<400> SEQUENCE: 27

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365
```

```
Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470


<210> SEQ ID NO 28
<211> LENGTH: 1422
<212> TYPE: DNA
<213> ORGANISM: Artificial sequence
<220> FEATURE:
<223> OTHER INFORMATION: UGT2_1a CpO for S. cerevisiae

<400> SEQUENCE: 28

atggctacat ctgattctat tgttgatgac aggaagcagt tgcatgtggc tactttccct      60

tggcttgctt tcggtcatat actgccttac ctacaactat caaaactgat agctgaaaaa     120

ggacataaag tgtcattcct ttcaacaact agaaacattc aaagattatc ttcccacata     180

tcaccattga ttaacgtcgt tcaattgaca cttccaagag tacaggaatt accagaagat     240

gctgaagcta caacagatgt gcatcctgaa gatatccctt acttgaaaaa ggcatccgat     300

ggattacagc ctgaggtcac tagattcctt gagcaacaca gtccagattg gatcatatac     360

gactacactc actattggtt gccttcaatt gcagcatcac taggcatttc tagggcacat     420

ttcagtgtaa ccacaccttg ggccattgct tacatgggtc catccgctga tgctatgatt     480

aacggcagtg atggtagaac taccgttgaa gatttgacaa ccccaccaaa gtggtttcca     540

tttccaacta aagtctgttg gagaaaacac gacttagcaa gactggttcc atacaaggca     600

ccaggaatct cagacggcta tagaatgggt ttagtcctta aagggtctga ctgcctattg     660

tctaagtgtt accatgagtt tgggacacaa tggctaccac ttttggaaac attacaccaa     720

gttcctgtcg taccagttgg tctattacct ccagaaatcc ctggtgatga gaaggacgag     780

acttgggttt caatcaaaaa gtggttagac gggaagcaaa aaggctcagt ggtatatgtg     840

gcactgggtt ccgaagtttt agtatctcaa acagaagttg tggaacttgc cttaggtttg     900

gaactatctg gattgccatt tgtctgggcc tacagaaaac caaaaggccc tgcaaagtcc     960

gattcagttg aattgccaga cggctttgtc gagagaacta gagatagagg gttggtatgg    1020

acttcatggg ctccacaatt gagaatcctg agtcacgaat ctgtgtgcgg tttcctaaca    1080

cattgtggtt ctggttctat agttgaagga ctgatgtttg gtcatccact tatcatgttg    1140

ccaatctttg gtgaccagcc tttgaatgca cgtctgttag aagataaaca agttggaatt    1200

gaaatcccac gtaatgagga agatggatgt ttaaccaagg agtctgtggc cagatcatta    1260

cgttccgttg tcgttgaaaa ggaaggcgaa atctacaagg ccaatgcccg tgaactttca    1320

aagatctaca atgacacaaa agtagagaag gaatatgttt ctcaatttgt agattaccta    1380

gagaaaaacg ctagagccgt agctattgat catgaatcct aa                       1422
```

-continued

<210> SEQ ID NO 29
<211> LENGTH: 1422
<212> TYPE: DNA
<213> ORGANISM: Artificial sequence
<220> FEATURE:
<223> OTHER INFORMATION: UGT2_1a CpO for Y. lipolitica

<400> SEQUENCE: 29
atggccacct ccgactccat tgtcgacgac cgaaagcagc tgcacgttgc caccttcccc 60
tggctcgcct ttggccacat tctgccctac ctccagctct ccaagctcat tgctgagaag 120
ggccacaagg tttctttcct gtccaccacc cgaaacatcc agcgactctc ctcccacatc 180
tctcctctca tcaacgttgt ccagctcacc ctcccccgag tccaggagct ccccgaggat 240
gccgaggcca ccactgatgt ccaccccgag gacatcccct acctcaagaa ggcctccgac 300
ggtctgcagc ccgaggtcac ccgattcctc gagcagcact ctcccgactg gatcatctac 360
gactacaccc actactggct cccctccatt gctgcttctc tcggtatctc tcgagcccac 420
ttctccgtca ccacccccctg ggccattgct tacatgggcc cctctgctga cgccatgatc 480
aacggttccg acggccgaac caccgtcgag gatctcacca cccctcccaa gtggttcccc 540
ttccccacca aggtctgctg gcgaaagcac gatctcgccc gactcgtccc ctacaaggcc 600
cccggtatct ccgacggtta ccgaatgggt ctggttctca agggctccga ctgtctgctc 660
tccaagtgct accacgagtt tggtacccag tggctccccc tgctcgagac tctgcaccag 720
gtccccgttg tccccgtcgg tctgctccct cccgagatcc ccggtgacga gaaggacgag 780
acttgggttt ccatcaagaa gtggctcgac ggcaagcaga agggctccgt cgtctacgtt 840
gctctcggct ccgaggttct tgtctcccag actgaggtcg tcgagctcgc cctcggtctg 900
gagctctccg gtctgccctt cgtctgggcc taccgaaagc ccaagggtcc cgccaagtcc 960
gactccgtcg agctccccga cggtttcgtc gagcgaactc gagatcgagg tctggtctgg 1020
acctcttggg ctccccagct ccgaatcctc tcccacgagt ccgtctgcgg tttcctgacc 1080
cactgtggtt ccggctccat tgtcgagggc ctcatgttcg gccacccccct catcatgctg 1140 cccatcttcg gtgaccagcc cctcaacgcc cgactcctcg aggacaagca ggtcggtatc 1200
gagatccccc gaaacgaaga ggacggctgc ctcaccaagg agtctgttgc ccgatctctg 1260
cgatctgttg ttgtcgagaa agagggtgag atctacaagg ccaacgcccg agagctctcc 1320
aagatctaca acgacaccaa ggtcgagaag gagtacgttt cccagtttgt cgactacctc 1380
gagaagaacg cccgagctgt cgccattgac cacgagagtt aa 1422

<210> SEQ ID NO 30
<211> LENGTH: 600
<212> TYPE: DNA
<213> ORGANISM: Artificial sequence
<220> FEATURE:
<223> OTHER INFORMATION: ScEno2 promoter

<400> SEQUENCE: 30
gtgtcgacgc tgcgggtata gaaagggttc tttactctat agtacctcct cgctcagcat 60
ctgcttcttc ccaaagatga acgcggcgtt atgtcactaa cgacgtgcac caacttgcgg 120
aaagtggaat cccgttccaa aactggcatc cactaattga tacatctaca caccgcacgc 180 ctttttttctg aagcccactt tcgtggactt tgccatatgc aaaattcatg aagtgtgata 240
ccaagtcagc atacacctca ctagggtagt ttctttggtt gtattgatca tttggttcat 300

-continued cgtggttcat taattttttt tctccattgc tttctggctt tgatcttact atcatttgga 360
tttttgtcga aggttgtaga attgtatgtg acaagtggca ccaagcatat ataaaaaaaa 420
aaagcattat cttcctacca gagttgattg ttaaaaacgt atttatagca aacgcaattg 480
taattaattc ttattttgta tcttttcttc ccttgtctca atcttttatt tttattttat 540
ttttcttttc ttagtttctt tcataacacc aagcaactaa tactataaca tacaataata 600

<210> SEQ ID NO 31
<211> LENGTH: 1056
<212> TYPE: DNA
<213> ORGANISM: Saccharomyces cerevisiae

<400> SEQUENCE: 31
atggcttctg aaaaggaaat cagaagagaa cgtttcttga atgttttccc aaaattggtt 60
gaagaattga acgcttctct attagcttac ggtatgccaa aggaagcttg tgactggtac 120
gctcactctt tgaactacaa caccccaggt ggtaagttga acagaggtct atccgttgtt 180
gacacctacg ccattttgtc caacaagacc gtcgaacaat taggtcaaga agaatacgaa 240
aaggttgcca tcttaggttg gtgtatcgaa ttgttgcaag cttacttctt ggttgctgat 300
gacatgatgg acaaatctat caccagaaga ggtcaaccat gttggtacaa ggttccagaa 360
gtcggtgaaa ttgccatcaa cgatgctttc atgttggaag ctgccatcta caagttgttg 420
aagtctcact tcagaaacga aaagtactac attgacatca ctgaattatt ccacgaagtt 480
actttccaaa ccgaattggg tcaattgatg gacttgatta ccgctccaga agataaggtc 540
gatttgtcca aattttcctt gaagaaacac tctttcattg tcactttcaa gactgcttac 600
tactcctttt acttgcctgt tgctttggcc atgtatgtcg ctggtatcac cgatgaaaag 660
gacttgaagc aagctcgtga tgtcttgatt ccattaggtg aatacttcca aatccaagat 720
gactacttgg actgtttcgg tactccagaa caaatcggta agattggtac tgatatccaa 780
gacaacaagt gttcctgggt tatcaacaag gctttggaat tggcttctgc tgaacaaaga 840
aagactttgg acgaaaacta cggtaagaag gactctgttg ctgaagctaa gtgtaagaag 900
atcttcaacg atttgaaaat tgaacaatta taccatgaat acgaagaatc tattgccaag 960
gacttgaaag ccaagatctc tcaagtcgac gaatccagag gtttcaaggc tgatgtcttg 1020
actgctttct tgaacaaggt ctacaagaga tcaaaa 1056

<210> SEQ ID NO 32
<211> LENGTH: 301
<212> TYPE: DNA
<213> ORGANISM: Artificial sequence
<220> FEATURE:
<223> OTHER INFORMATION: Adh1 terminator

<400> SEQUENCE: 32
agcgaatttc ttatgattta tgatttttat tattaaataa gttataaaaa aaataagtgt 60
atacaaattt taaagtgact cttaggtttt aaaacgaaaa ttcttattct tgagtaactc 120
tttcctgtag gtcaggttgc tttctcaggt atagcatgag gtcgctctta ttgaccacac 180
ctctaccggc atgccgagca aatgcctgca aatcgctccc catttcaccc aattgtagat 240
atgctaactc cagcaatgag ttgatgaatc tcggtgtgta ttttatgtcc tcagaggaca 300
a 301

<210> SEQ ID NO 33
<211> LENGTH: 600

<212> TYPE: DNA
<213> ORGANISM: Artificial sequence
<220> FEATURE:
<223> OTHER INFORMATION: Sc Fba1 promoter

<400> SEQUENCE: 33
ctacttggct tcacatacgt tgcatacgtc gatatagata ataatgataa tgacagcagg 60
attatcgtaa tacgtaatag ttgaaaatct caaaaatgtg tgggtcatta cgtaaataat 120
gataggaatg ggattcttct atttttcctt tttccattct agcagccgtc gggaaaacgt 180
ggcatcctct ctttcgggct caattggagt cacgctgccg tgagcatcct ctctttccat 240
atctaacaac tgagcacgta accaatggaa aagcatgagc ttagcgttgc tccaaaaaag 300
tattggatgg ttaataccat ttgtctgttc tcttctgact ttgactcctc aaaaaaaaaa 360
aatctacaat caacagatcg cttcaattac gccctcacaa aaactttttt ccttcttctt 420
cgcccacgtt aaattttatc cctcatgttg tctaacggat ttctgcactt gatttattat 480
aaaaagacaa agacataata cttctctatc aatttcagtt attgttcttc cttgcgttat 540
tcttctgttc ttcttttttct tttgtcatat ataaccataa ccaagtaata catattcaaa 600

<210> SEQ ID NO 34
<211> LENGTH: 1575
<212> TYPE: DNA
<213> ORGANISM: Saccharomyces cerevisiae

<400> SEQUENCE: 34
atggaccaat tggtcaagac tgaagtcacc aagaaatctt tcactgctcc agtccaaaag 60
gcttccactc cagttttgac caacaagacc gtcatctccg gttccaaggt taaatctttg 120
tcctctgctc aatcttcctc ctctggtcca tcttcttctt ctgaagaaga tgattccaga 180
gatatcgaat ctttggacaa gaaaatcaga ccattggaag aattggaagc tctattgtcc 240
tctggtaaca ctaagcaatt aaagaacaag gaagttgctg ctttggttat ccacggtaaa 300
ttgccattgt acgctttgga aaagaaatta ggtgacacca ccagagctgt tgctgtcaga 360
agaaaggctt tgtccatttt ggctgaagct ccagtcttgg cttccgacag attaccatac 420
aagaactacg actacgaccg tgtctttggt gcttgttgtg aaaatgtcat tggttacatg 480
ccattaccag ttggtgtcat tggtccattg gttatcgacg gtacttctta ccacatccca 540
atggctacca ctgaaggttg tttggttgct tctgccatga gaggttgtaa ggccatcaac 600
gctggtggtg gtgctaccac cgttttgact aaggatggta tgaccagagg tcctgttgtc 660
agattcccaa ctttgaagag atctggtgct tgtaagatct ggttggattc tgaagaaggt 720
caaaacgcca tcaagaaggc tttcaactcc acttccagat tcgctagatt gcaacacatt 780
caaacttgtt tagctggtga cttgttgttc atgagattca gaaccaccac tggtgacgct 840
atgggtatga acatgatctc caagggtgtt gaatactctt tgaagcaaat ggttgaagaa 900
tacggttggg aagatatgga agttgtctct gtttctggta actactgtac cgacaagaag 960
ccagctgcca tcaactggat cgaaggtcgt ggtaagtccg ttgttgctga agctaccatt 1020
ccaggtgacg ttgtcagaaa ggttttgaaa tctgatgttt ctgctttagt cgaattgaac 1080
attgccaaga acttggtcgg ttctgccatg gctggttccg tcggtggttt caacgctcat 1140
gccgctaact tggtcactgc tgttttcttg gctttaggtc aagatccagc tcaaaatgtc 1200
gaatcctcta actgtatcac tttgatgaag gaagttgacg gtgatttgag aatttctgtt 1260
tccatgccat ccattgaagt cggtactatc ggtggtggta ctgtcttgga accacaaggt 1320

-continued

```
gccatgttgg acttgttggg tgttcgtggt ccacacgcta ccgctccagg tactaacgcc   1380

agacaattgg ccagaattgt tgcctgtgcc gtcttggctg gtgaattgtc tctatgtgcc   1440

gctttggctg ctggtcactt ggttcaatct cacatgaccc acaacagaaa gcctgctgaa   1500

ccaaccaaac caaacaactt ggatgctact gacattaaca gattaaagga cggttctgtc   1560

acctgtatca agtct                                                      1575


<210> SEQ ID NO 35
<211> LENGTH: 301
<212> TYPE: DNA
<213> ORGANISM: Artificial sequence
<220> FEATURE:
<223> OTHER INFORMATION: Adh2 terminator

<400> SEQUENCE: 35

agcggatctc ttatgtcttt acgatttata gttttcatta tcaagtatgc ctatattagt     60

atatagcatc tttagatgac agtgttcgaa gtttcacgaa taaaagataa tattctactt    120

tttgctccca ccgcgtttgc tagcacgagt gaacaccatc cctcgcctgt gagttgtacc    180

cattcctcta aactgtagac atggtagctt cagcagtgtt cgttatgtac ggcatcctcc    240

aacaaacagt cggttatagt ttgtcctgct cctctgaatc gtgtccctcg atatttctca    300

t                                                                     301


<210> SEQ ID NO 36
<211> LENGTH: 600
<212> TYPE: DNA
<213> ORGANISM: Artificial sequence
<220> FEATURE:
<223> OTHER INFORMATION: Sc Tef1 promoter

<400> SEQUENCE: 36

ttggctgata atagcgtata aacaatgcat actttgtacg ttcaaaatac aatgcagtag     60

atatatttat gcatattaca tataatacat atcacatagg aagcaacagg cgcgttggac    120

ttttaatttt cgaggaccgc gaatccttac atcacaccca atcccccaca agtgatcccc    180

cacacaccat agcttcaaaa tgtttctact cctttttac tcttccagat tttctcggac     240

tccgcgcatc gccgtaccac ttcaaaacac ccaagcacag catactaaat ttcccctctt    300

tcttcctcta gggtgtcgtt aattacccgt actaaaggtt tggaaaagaa aaaagacacc    360

gcctcgtttc tttttcttcg tcgaaaaagg caataaaaat ttttatcacg tttcttttc     420

ttgaaaattt ttttttttga tttttttctc tttcgatgac ctcccattga tatttaagtt    480

aataaacggt cttcaatttc tcaagtttca gtttcatttt tcttgttcta ttacaacttt    540

ttttacttct tgctcattag aaagaaagca tagcaatcta atctaagttt taattacaaa    600


<210> SEQ ID NO 37
<211> LENGTH: 1005
<212> TYPE: DNA
<213> ORGANISM: Saccharomyces cerevisiae

<400> SEQUENCE: 37

atggaagcta agattgacga attgatcaac aacgaccctg tctggtcctc tcaaaacgaa     60

tctttgatct ccaagccata caaccacatc ttgttgaagc caggtaagaa cttcagatta    120

aacttgattg ttcaaatcaa cagagttatg aacttgccaa aggaccaatt ggccattgtt    180

tcccaaattg tcgaattgtt gcacaactcc tctctattga tcgatgacat tgaagataat    240

gctccattaa gaagaggtca aaccacttct catttgattt tcggtgtccc atccaccatc    300
```

```
aacactgcta actacatgta cttcagagcc atgcaattgg tttctcaatt gaccaccaag    360

gaaccattat accacaactt gatcactatc tttaacgaag aattgattaa cttgcaccgt    420

ggtcaaggtt tggacatcta ctggagagat ttcttgccag aaattattcc aactcaagaa    480

atgtacttga acatggtcat gaacaagact ggtggtttat tcagattgac tttacgtttg    540

atggaagctt tgtctccatc ttcccaccac ggtcactctt tggttccatt catcaatcta    600

ttaggtatca tctaccaaat cagagatgat tacttgaact tgaaggactt ccaaatgtcc    660

tctgaaaagg gtttcgctga agatatcact gaaggtaaat tgtctttccc aattgtccac    720

gccttgaact ttaccaagac caagggtcaa actgaacaac acaacgaaat tttgagaatc    780

ttattgttga gaacttctga caaggacatc aagttgaaat tgatccaaat cttggaattc    840

gataccaact ctttggctta caccaagaac ttcatcaacc aattggttaa catgatcaag    900

aatgacaacg aaaacaaata cttgccagac ttggcttccc actccgatac cgctaccaac    960

ttgcacgacg aattgttgta cattattgac catttgtctg agtta                  1005
```

<210> SEQ ID NO 38
<211> LENGTH: 301
<212> TYPE: DNA
<213> ORGANISM: Artificial sequence
<220> FEATURE:
<223> OTHER INFORMATION: Sc Gmp1 terminator

<400> SEQUENCE: 38

```
agtctgaaga atgaatgatt tgatgatttc tttttccctc catttttctt actgaatata     60

tcaatgatat agacttgtat agtttattat ttcaaattaa gtagctatat atagtcaaga    120

taacgtttgt ttgacacgat tacattattc gtcgacatct tttttcagcc tgtcgtggta    180

gcaatttgag gagtattatt aattgaatag gttcattttg cgctcgcata aacagttttc    240

gtcagggaca gtatgttgga atgagtggta attaatggtg acatgacatg ttatagcaat    300

a                                                                   301
```

<210> SEQ ID NO 39
<211> LENGTH: 600
<212> TYPE: DNA
<213> ORGANISM: Artificial sequence
<220> FEATURE:
<223> OTHER INFORMATION: Sc Pgk1 promoter

<400> SEQUENCE: 39

```
gggccagaaa aaggaagtgt ttccctcctt cttgaattga tgttaccctc ataaagcacg     60

tggcctctta tcgagaaaga aattaccgtc gctcgtgatt tgtttgcaaa aagaacaaaa    120

ctgaaaaaac ccagacacgc tcgacttcct gtcttcctat tgattgcagc ttccaatttc    180

gtcacacaac aaggtcctag cgacggctca caggttttgt aacaagcaat cgaaggttct    240

ggaatggcgg gaaagggttt agtaccacat gctatgatgc ccactgtgat ctccagagca    300

aagttcgttc gatcgtactg ttactctctc tctttcaaac agaattgtcc gaatcgtgtg    360

acaacaacag cctgttctca cacactcttt tcttctaacc aagggggtgg tttagtttag    420

tagaacctcg tgaaacttac atttacatat atataaactt gcataaattg gtcaatgcaa    480

gaaatacata tttggtcttt tctaattcgt agtttttcaa gttcttagat gctttctttt    540

tctctttttt acagatcatc aaggaagtaa ttatctactt tttacaacaa atataaaaca    600
```

<210> SEQ ID NO 40

-continued

<211> LENGTH: 1001
<212> TYPE: DNA
<213> ORGANISM: Artificial sequence
<220> FEATURE:
<223> OTHER INFORMATION: Kl prom 12 promoter

<400> SEQUENCE: 40

```
cgtaaaaact aaaacgagcc cccaccaaag aacaaaaaag aaggtgctgg gcccccactt      60
tcttcccttg cacgtgatag gaagatggct acagaaacaa gaagatggaa atcgaaggaa     120
agagggagac tggaagctgt aaaaactgaa atgaaaaaaa aaaaaaaaaa aaaaaaacaa     180
gaagctgaaa atggaagact gaaatttgaa aaatggtaaa aaaaaaaaag aaacacgaag     240
ctaaaaacct ggattccatt ttgagaagaa gcaagaaagg taagtatggt aacgaccgta     300
caggcaagcg cgaaggcaaa tggaaaagct ggagtccgga agataatcat ttcatcttct     360
tttgttagaa cagaacagtg gatgtccctc atctcggtaa cgtattgtcc atgccctaga     420
actctctgtc cctaaaaaga ggacaaaaac ccaatggttt ccccagcttc cagtggagcc     480
accgatccca ctggaaacca ctggacagga agagaaaatc acggacttcc tctattgaag     540
gataattcaa cactttcacc agatcccaaa tgtcccgccc ctattcccgt gttccatcac     600
gtaccataac ttaccatttc atcacgttct ctatggcaca ctggtactgc ttcgactgct     660
ttgcttcatc ttctctatgg gccaatgagc taatgagcac aatgtgctgc gaaataaagg     720
gatatctaat ttatattatt acattataat atgtactagt gtggttattg gtaattgtac     780
ttaattttga tatataaagg gtggatcttt ttcattttga atcagaattg gaattgcaac     840
ttgtctcttg tcactattac ttaatagtaa ttatatttct tattaacctt ttttttaagt     900
caaaacacca aggacaagaa ctactcttca aaggtatttc aagttatcat acgtgtcaca     960
cacgcttcac agtttcaagt aaaaaaaaag aatattacac a                        1001
```

<210> SEQ ID NO 41
<211> LENGTH: 2229
<212> TYPE: DNA
<213> ORGANISM: Stevia rebaudiana

<400> SEQUENCE: 41

```
atgtgtaaag ctgtttccaa ggaatactct gacttgttgc aaaaggatga agcctccttc      60
accaaatggg atgatgacaa agttaaggac catttagaca ctaacaagaa cttgtaccca     120
aacgatgaaa tcaaggaatt cgtcgaatct gtcaaagcta tgttcggttc catgaatgat     180
ggtgaaatca acgtttccgc ttacgacacc gcttgggttg ctttggttca agacgttgat     240
ggttccggtt ctccacaatt cccatcttct ttggaatgga ttgccaacaa ccaattgtct     300
gatggttctt ggggtgacca tttgttattc tctgctcacg acagaattat taacacttta     360
gcttgtgtca ttgctttgac ttcctggaat gtccatccat ccaagtgtga aaagggtttg     420
aacttcttga gagaaaacat ctgtaagttg gaagatgaaa atgctgaaca catgccaatt     480
ggtttcgaag ttaccttccc atctttgatt gatatcgcca agaagttgaa catcgaagtc     540
ccagaagaca ccccagcttt gaaggaaatc tacgccagaa gagatatcaa gttgaccaaa     600
atcccaatgg aagttttgca caaggttcca accaccttgt tgcactcttt ggaaggtatg     660
ccagacttgg aatgggaaaa gttgttaaag ttgcaatgta aggacggttc tttcttgttc     720
tctccatctt ctaccgcctt tgctttgatg caaactaagg acgaaaagtg tctacaatac     780
ttaactaata tcgttaccaa attcaacggt ggtgtcccaa acgtttaccc tgttgacttg     840
tttgaacaca tctgggttgt tgacagattg caacgtttgg gtattgctcg ttatttcaag     900
```

-continued

```
tctgaaatca aggactgtgt tgaatacatc aacaagtact ggactaagaa cggtatctgt    960

tgggctcgta acacccacgt tcaagatatc gacgacactg ctatgggttt cagagtcttg   1020

agagctcatg gttacgatgt caccccagat gtcttcagac aattcgaaaa ggatggtaag   1080

ttcgtttgtt ttgccggtca atccactcaa gccgtcactg gtatgttcaa cgtctacaga   1140

gcttctcaaa tgttgttccc aggtgaaaga atcctagaag acgctaagaa gttctcctac   1200

aactacttga aagaaaagca atctactaac gaattgttgg acaaatggat cattgccaaa   1260

gacttaccag gtgaagtcgg ttacgctttg gatattccat ggtacgcttc tctaccaaga   1320

ttagaaacca gatactactt ggaacaatac ggtggtgaag acgatgtctg gatcggtaag   1380

accttgtaca gaatgggtta cgtttccaac aacacttact tggaaatggc caaattggac   1440

tacaacaact acgtcgccgt cttacaattg gaatggtaca ccattcaaca atggtacgtt   1500

gacattggta ttgaaaagtt tgaatccgac aacatcaagt ccgtcttggt ttcctactac   1560

ttggctgctg cttccatctt tgaaccagaa agatccaagg aaagaattgc ttgggctaag   1620

accaccatct tggttgacaa gatcacttct attttcgact cttcccaatc ttccaaggaa   1680

gatatcaccg ctttcattga caaattcaga aacaagtctt cttccaagaa gcactccatt   1740

aacggtgaac catggcacga agttatggtt gctttgaaga agactttgca cggttttgct   1800

ttggatgctt tgatgactca ctctcaagat attcaccctc aattacacca agcttgggaa   1860

atgtggttaa ccaagttgca agatggtgtc gatgtcactg ctgaattgat ggttcaaatg   1920

atcaacatga ctgccggtag atgggtttct aaggaattgt tgactcaccc tcaataccaa   1980

cgtttgtcca ccgtcaccaa ctctgtctgt cacgacatca ctaagttgca caacttcaaa   2040

gaaaactcca ctactgtcga ttctaaggtt caagaattgg ttcaattagt tttctctgac   2100

accccagatg acttggacca agacatgaag caaactttct tgactgtcat gaagaccttc   2160

tactacaagg cttggtgtga cccaaacacc atcaacgacc atatttctaa ggtcttcgaa   2220

attgttatc                                                           2229


<210> SEQ ID NO 42
<211> LENGTH: 2271
<212> TYPE: DNA
<213> ORGANISM: Stevia rebaudiana

<400> SEQUENCE: 42

atgacttctc acggtggtca aaccaaccca accaacttga ttattgacac caccaaggaa     60

agaatccaaa agcaattcaa gaatgttgaa atctccgttt cctcctacga cactgcttgg    120

gttgccatgg ttccatctcc aaactcccca aagtctccat gtttcccaga atgtttgaac    180

tggttaatca acaaccaatt gaacgatggt tcctggggtt tagtcaatca cacccacaac    240

cacaatcacc cattgttgaa ggactctcta tcctccactt tggcttgtat cgttgctttg    300

aagagatgga acgttggtga agaccaaatc aacaagggtt tgtcctttat tgaatccaac    360

ttggcttctg ctactgaaaa gtcccaacca tctcctatcg gttttgacat cattttccca    420

ggtttattgg aatacgctaa gaacttggac atcaacttat tatctaagca aaccgatttc    480

tccttgatgt tgcacaagag agaattggaa caaaagagat gtcactccaa cgaaatggac    540

ggttacttgg cttacatttc tgaaggtttg ggtaacttgt acgactggaa catggtcaag    600

aaataccaaa tgaagaacgg ttccgttttc aactctccat ctgctaccgc tgctgctttc    660

atcaaccatc aaaacccagg ttgtttgaac tacttgaact ctttgttgga caaattcggt    720
```

-continued

```
aacgctgttc caactgtcta cccacacgat ttgtttatca gattatccat ggttgacacc    780

attgaacgtt tgggtatttc tcatcacttc agagtcgaaa tcaagaacgt tttggatgaa    840

acttacagat gttgggttga aagagatgaa caaatcttca tggatgtcgt cacttgtgcc    900

ttggccttca gattattgag aattaacggt tacgaagttt ctccagaccc attggctgaa    960

atcactaacg aattggcttt gaaggacgaa tacgccgctt tggaaactta ccatgcctct   1020

cacatcttat accaagaaga cttgtcctct ggtaagcaaa tcttgaagtc tgctgacttc   1080

ttgaaggaaa ttatctctac tgattctaac agattgtcca agttgattca caaggaagtt   1140

gaaaacgcct tgaaattccc aatcaacact ggtttggaaa gaattaacac cagaagaaac   1200

atccaattat acaacgttga caacactaga atcttgaaga ctacttatca ctcttccaac   1260

atctccaaca ctgactactt gagattggct gtcgaagatt tctacacctg tcaatctatt   1320

tacagagaag aattgaaggg tttggaaaga tgggttgtcg aaaacaaatt ggaccaattg   1380

aaatttgcta gacaaaagac cgcctactgt tacttctccg ttgctgccac tttgtcctct   1440

ccagaattat ctgacgccag aatctcctgg gctaagaatg gtatcttgac caccgttgtc   1500

gatgacttct tcgatattgg tggtaccatt gacgaattga ccaacttgat tcaatgtgtt   1560

gaaaagtgga acgtcgatgt cgataaggac tgttgttctg aacacgtcag aatcttattc   1620

ttggctttga aagatgctat ctgttggatc ggtgacgaag ctttcaaatg gcaagctcgt   1680

gacgttacct ctcacgtcat ccaaacctgg ttggaattga tgaactctat gttgagagaa   1740

gccatctgga cccgtgatgc ttacgtccca actttgaacg aatacatgga aaatgcttac   1800

gtttctttcg ctttgggtcc aattgtcaag cctgctattt acttcgttgg tccaaagttg   1860

tccgaagaaa ttgttgaatc ttctgaatac cacaacttgt tcaaattgat gtctactcaa   1920

ggtcgtttgt tgaacgatat ccactctttc aagcgtgaat tcaaggaagg taagttgaat   1980

gctgttgctt tgcatttgtc taacggtgaa tctggtaagg tcgaagaaga agttgtcgaa   2040

gaaatgatga tgatgatcaa gaacaagaga aaggaattga tgaagttgat ctttgaagaa   2100

aacggttcta ttgtcccaag agcttgtaag gatgctttct ggaacatgtg tcacgtcttg   2160

aacttcttct acgctaacga tgacggtttc actggtaaca ccatcttaga caccgtcaag   2220

gacatcattt acaacccatt agtcttggtt aacgaaaacg aagaacaaag a            2271
```

<210> SEQ ID NO 43
<211> LENGTH: 301
<212> TYPE: DNA
<213> ORGANISM: Artificial sequence
<220> FEATURE:
<223> OTHER INFORMATION: Sc Tal1 terminator

<400> SEQUENCE: 43

```
aggaagtatc tcggaaatat taatttaggc catgtcctta tgcacgtttc ttttgatact     60

tacgggtaca tgtacacaag tatatctata tatataaatt aatgaaaatc ccctatttat    120

atatatgact ttaacgagac agaacagttt tttatttttt atcctatttg atgaatgata    180

cagtttctta ttcacgtgtt atacccacac caaatccaat agcaataccg gccatcacaa    240

tcactgtttc ggcagcccct aagatcagac aaaacatccg gaaccacctt aaatcaacgt    300

c                                                                    301
```

<210> SEQ ID NO 44
<211> LENGTH: 1575
<212> TYPE: DNA
<213> ORGANISM: Gibberella fujikuroi

<400> SEQUENCE: 44
atgtccaagt ctaactccat gaactccact tctcacgaaa ctttattcca acaattggtt 60
ttgggtttgg acagaatgcc attgatggat gtccactggt tgatctacgt tgctttcggt 120
gcttggttat gttcctacgt cattcacgtt ttgtcctctt cttctaccgt caaggttcca 180
gttgtcggtt acagatccgt tttcgaacca acctggttat tgagattaag atttgtctgg 240
gaaggtggtt ccattattgg tcaaggttac aacaaattca aggactctat cttccaagtc 300
agaaagttgg gtactgacat tgttatcatc ccaccaaact acatcgatga agtcagaaag 360
ttgtcccaag acaagaccag atctgttgaa ccattcatca acgatttcgc tggtcaatac 420
accagaggta tggtctttct acaatctgat ttgcaaaacc gtgtcatcca acaaagattg 480
actccaaagt tggtttcttt gactaaggtc atgaaggaag aattggacta cgctttgacc 540
aaggaaatgc cagacatgaa gaacgacgaa tgggttgaag ttgacatttc ttccatcatg 600
gtcagattga tctccagaat ctctgcccgt gttttcttgg gtccagaaca ctgtcgtaac 660
caagaatggt tgaccaccac tgctgaatac tctgaatctt tattcatcac tggtttcatc 720
ttgagagttg tcccacacat cttaagacca ttcattgctc cattgttgcc ttcttacaga 780
actttgttga gaaatgtctc ttctggtaga agagttatcg gtgatatcat cagatctcaa 840
caaggtgatg gtaacgaaga tatcttgtcc tggatgagag atgctgctac cggtgaagaa 900
aagcaaattg acaacattgc tcaaagaatg ttgatcttgt ctttggcttc cattcacacc 960
accgccatga ccatgaccca tgccatgtac gacttgtgtg cctgtccaga atacattgaa 1020
ccattacgtg acgaagtcaa atccgttgtt ggtgcttctg gttgggacaa gactgctttg 1080
aacagattcc acaagttgga ctctttcttg aaggaatctc aaagattcaa cccagttttc 1140
ttgttgactt tcaacagaat ctaccatcaa tccatgactt tgtccgatgg taccaacatt 1200
ccatctggta ccagaattgc tgttccatct cacgctatgt tgcaagattc tgctcacgtt 1260
ccaggtccaa ctcctccaac tgaatttgac ggtttcagat actccaagat cagatctgac 1320
tctaactatg ctcaaaagta cttgttctcc atgaccgatt cttccaacat ggctttcggt 1380
tacggtaagt acgcttgtcc aggtcgtttc tacgcctcca acgaaatgaa attgactttg 1440
gccattttgt tgttgcaatt tgaattcaaa ttgccagatg gtaagggtag accaagaaac 1500
atcactatcg actctgacat gattccagac ccaagagcta gattatgtgt cagaaagaga 1560
tctctacgtg acgaa 1575

<210> SEQ ID NO 45
<211> LENGTH: 301
<212> TYPE: DNA
<213> ORGANISM: Artificial sequence
<220> FEATURE:
<223> OTHER INFORMATION: Sc Tpi1 terminator

<400> SEQUENCE: 45
agattaatat aattatataa aaatattatc ttcttttctt tatatctagt gttatgtaaa 60
ataaattgat gactacggaa agctttttta tattgtttct ttttcattct gagccactta 120
aatttcgtga atgttcttgt aagggacggt agatttacaa gtgatacaac aaaaagcaag 180
gcgctttttc taataaaaag aagaaaagca tttaacaatt gaacacctct atatcaacga 240
agaatattac tttgtctcta aatccttgta aaatgtgtac gatctctata tgggttactc 300
a 301

-continued

<210> SEQ ID NO 46
<211> LENGTH: 403
<212> TYPE: DNA
<213> ORGANISM: Artificial sequence
<220> FEATURE:
<223> OTHER INFORMATION: Ag lox_TEF1 promoter

<400> SEQUENCE: 46
taccgttcgt ataatgtatg ctatacgaag ttatgtcccc gccgggtcac ccggccagcg 60
acatggaggc ccagaatacc ctccttgaca gtcttgacgt gcgcagctca ggggcatgat 120
gtgactgtcg cccgtacatt tagcccatac atccccatgt ataatcattt gcatccatac 180
attttgatgg ccgcacggcg cgaagcaaaa attacggctc ctcgctgcag acctgcgagc 240
agggaaacgc tcccctcaca gacgcgttga attgtcccca cgccgcgccc ctgtagagaa 300
atataaaagg ttaggatttg ccactgaggt tcttctttca tatacttcct tttaaaatct 360
tgctaggata cagttctcac atcacatccg aacataaaca aca 403

<210> SEQ ID NO 47
<211> LENGTH: 810
<212> TYPE: DNA
<213> ORGANISM: Artificial sequence
<220> FEATURE:
<223> OTHER INFORMATION: KANMX

<400> SEQUENCE: 47
atgggtaagg aaaagactca cgtttcgagg ccgcgattaa attccaacat ggatgctgat 60
ttatatgggt ataaatgggc tcgcgataat gtcgggcaat caggtgcgac aatctatcga 120
ttgtatggga agcccgatgc gccagagttg tttctgaaac atggcaaagg tagcgttgcc 180
aatgatgtta cagatgagat ggtcagacta aactggctga cggaatttat gcctcttccg 240
accatcaagc attttatccg tactcctgat gatgcatggt tactcaccac tgcgatcccc 300
ggcaaaacag cattccaggt attagaagaa tatcctgatt caggtgaaaa tattgttgat 360
gcgctggcag tgttcctgcg ccggttgcat tcgattcctg tttgtaattg tccttttaac 420
agcgatcgcg tatttcgttt ggctcaggcg caatcacgaa tgaataacgg tttggttgat 480
gcgagtgatt ttgatgacga gcgtaatggc tggcctgttg aacaagtctg gaaagaaatg 540
cataagcttt tgccattctc accggattca gtcgtcactc atggtgattt ctcacttgat 600
aaccttattt ttgacgaggg gaaattaata ggttgtattg atgttggacg agtcggaatc 660
gcagaccgat accaggatct tgccatccta tggaactgcc tcggtgagtt ttctccttca 720
ttacagaaac ggctttttca aaaatatggt attgataatc ctgatatgaa taaattgcag 780
tttcatttga tgctcgatga gtttttctaa 810

<210> SEQ ID NO 48
<211> LENGTH: 285
<212> TYPE: DNA
<213> ORGANISM: Artificial sequence
<220> FEATURE:
<223> OTHER INFORMATION: Ag Tef1_lox terminator

<400> SEQUENCE: 48
atcagtactg acaataaaaa gattcttgtt ttcaagaact tgtcatttgt atagtttttt 60
tatattgtag ttgttctatt ttaatcaaat gttagcgtga tttatatttt ttttcgcctc 120
gacatcatct gcccagatgc gaagttaagt gcgcagaaag taatatcatg cgtcaatcgt 180
atgtgaatgc tggtcgctat actgctgtcg attcgatact aacgccgcca tccagtgtcg 240
aaaacgagct cataacttcg tataatgtat gctatacgaa cggta 285

<210> SEQ ID NO 49
<211> LENGTH: 1575
<212> TYPE: DNA
<213> ORGANISM: Arabidopsis thaliana

<400> SEQUENCE: 49
atggaatctt tagtcgttca caccgtcaat gccatctggt gtattgtcat tgttggtatt 60
ttctctgttg gttaccacgt ttacggtcgt gccgttgttg aacaatggag aatgagaaga 120
tctttgaaat tgcaaggtgt caagggtcca ccaccatcca ttttcaacgg taatgtctct 180
gaaatgcaaa gaatccaatc tgaagctaag cactgttccg gtgacaacat catttctcac 240
gattactcct cctctttgtt ccctcacttt gaccactgga gaaagcaata cggtagaatc 300
tacacctact ccactggttt gaaacaacat ttgtacatca accatccaga aatggtcaag 360
gaattatctc aaaccaacac tttgaactta ggtcgtatca ctcacatcac caagagattg 420
aacccaatct taggtaacgg tatcatcact tccaacggtc cacactgggc tcatcaaaga 480
agaattattg cttacgaatt cacccacgac aaaatcaagg gtatggtcgg tttgatggtc 540
gaatctgcca tgccaatgtt gaacaaatgg gaagaaatgg ttaagagagg tggtgaaatg 600
ggttgtgaca tccgtgttga cgaagatttg aaggatgttt ctgctgatgt cattgctaag 660
gcttgtttcg gttcctcttt ctccaagggt aaggctatct tctccatgat cagagacttg 720
ttgactgcca tcactaagag atctgttttg ttcagattca acggtttcac cgacatggtt 780
ttcggttcca agaagcatgg tgatgtcgat atcgatgctt tggaaatgga attggaatct 840
tctatctggg aaaccgttaa ggaaagagaa attgaatgta aggacactca caagaaggat 900
ttgatgcaat taatcttgga aggtgccatg agatcttgtg acggtaactt gtgggacaag 960
tctgcttaca gaagatttgt tgtcgacaac tgtaaatcca tctactttgc cggtcacgac 1020
tctactgctg tctccgtttc ctggtgtttg atgttgctag ctttgaaccc atcctggcaa 1080
gtcaagatca gagatgaaat cttatcttct tgtaagaacg gtattccaga tgctgaatcc 1140
attccaaact tgaagaccgt taccatggtc attcaagaaa ctatgagatt gtacccacca 1200
gctccaattg tcggtagaga agcttccaag gacatcagat taggtgactt ggttgttcca 1260
aagggtgttt gtatctggac tttgattcca gctttgcacc gtgacccaga aatctggggt 1320
ccagatgcta acgacttcaa gccagaaaga ttctctgaag gtatttccaa ggcttgtaaa 1380
tacccacaat cttacatccc attcggtttg ggtccaagaa cctgtgtcgg taagaacttc 1440
ggtatgatgg aagtcaaagt tttggtttct ttgattgttt ccaagttctc tttcaccttg 1500
tctccaactt accaacactc tccatctcac aagttgttgg ttgaacctca acacggtgtt 1560
gtcattagag tcgtt 1575

<210> SEQ ID NO 50
<211> LENGTH: 1000
<212> TYPE: DNA
<213> ORGANISM: Artificial sequence
<220> FEATURE:
<223> OTHER INFORMATION: Kl prom 6 promoter

<400> SEQUENCE: 50
caaagggggg gcagggacag ggatacgaca agggctgggg aaaaaaaaaa agatagatac 60
gattggccgg gtaagcctgg ggaaatgtag caagtgcggg taagttaaaa ggtaaccacg 120

-continued

```
tgactccgga agagtcacgt ggttacggac ttttttctct agatctcagc tttttatcgg    180

tcttaccctg ccctcctgcc ccctgcccct tccctttgcc ccaaaaagaa aggaaatctg    240

ttggatttcg ctcaggccat ccctttcgtt aatatcggtt atcgctttac acactgcaca    300

tccttctgtc caaaaggaat ccagaagttt agcttttcct tcctttccca cagacattag    360

cctaggccct ctctcatcat ttgcatgcct cagccaatgt accaagaata acgcaacgag    420

gttgggaaat tttaacccaa caatcgatgc agatgtgaca agagattaga cacgttccag    480

ataccagatt acacagcttg tgctagcaga gtgacatatg gtggtgttgt gtctcgttta    540

gtacctgtaa tcgagagtgt tcaaatcagt cgatttgaac acccttactg ccactgaata    600

ttgattgaat accgtttatt gaaggtttta tgagtgatct tctttcggtc caggacaatt    660

tgttgagctt tttctatgta gagttccgtc ccttttttt tttttttgc tttctcgcac    720

ttactagcac tatttttttt tcacacacta aaacacttta ttttaatcta tatatatata    780

tatatatata tgtaggaatg gaatcacaga catttgatac tcatcctcat ccttattaat    840

tcttgtttta atttgtttga cttagccaaa ccaccaatct caacccatcg tatttcaggt    900

attgtgtgtc tagtgtgtct ctggtatacg gaaataagtg ccagaagtaa ggaagaaaca    960

aagaacaagt gtctgaatac tactagcctc tcttttcata                         1000
```

<210> SEQ ID NO 51
<211> LENGTH: 2133
<212> TYPE: DNA
<213> ORGANISM: Arabidopsis thaliana

<400> SEQUENCE: 51

```
atgtcctctt cttcttcttc ttctacttcc atgattgatt tgatggctgc catcatcaag     60

ggtgaaccag tcattgtctc tgacccagcc aacgcttctg cttacgaatc cgttgctgct    120

gaattgtcct ccatgttgat tgaaaacaga caattcgcta tgattgtcac tacttccatt    180

gctgtcttga ttggttgtat cgtcatgttg gtctggagaa gatccggttc cggtaactcc    240

aagagagttg aaccattgaa gccattagtc atcaagccaa gagaagaaga aattgatgac    300

ggtagaaaga aggtcaccat cttctttggt actcaaaccg gtactgctga aggttttgct    360

aaggctttgg gtgaagaagc caaagctaga tacgaaaaga ccagattcaa gatcgttgac    420

ttggacgact acgctgctga tgacgacgaa tacgaagaaa agttgaagaa ggaagatgtt    480

gccttcttct tcttggctac ttacggtgat ggtgaaccaa ctgacaatgc tgccagattc    540

tacaaatggt tcaccgaagg taacgacaga ggtgaatggt taaagaactt gaaatacggt    600

gttttcggtc taggtaacag acaatacgaa cacttcaaca aggttgccaa ggttgtcgat    660

gacatcttgg ttgaacaagg tgctcaaaga ttagtccaag tcggtttggg tgatgatgac    720

caatgtatcg aagatgactt cactgcttgg agagaagctt tgtggccaga attggacacc    780

atcttaagag aagaaggtga taccgctgtt gccaccccat acactgctgc tgttttggaa    840

tacagagttt ctatccacga ctctgaagat gccaagttca acgacatcaa catggctaac    900

ggtaacggtt acactgtttt cgacgctcaa cacccataca aggccaatgt tgctgtcaag    960

agagaattgc acactccaga atctgatcgt tcttgtatcc acttggaatt tgacattgct   1020

ggttctggtt tgacctacga aaccggtgac cacgtcggtg tcttatgtga caacttgtct   1080

gaaactgtcg atgaagcttt gagattattg gacatgtctc cagacactta tttctccttg   1140

catgctgaaa aggaagatgg tactccaatt tcttcttcct tgcctcctcc attcccacca   1200

tgtaacttga gaaccgcttt aaccagatac gcttgtttgc tatcctctcc aaagaagtcc   1260
```

gctttggttg ctttggctgc tcacgcttct gacccaactg aagctgaaag attgaaacat 1320
ttggcttccc cagctggtaa ggatgaatac tccaaatggg ttgttgaatc tcaaagatct 1380
ttgttggaag tcatggctga attcccatct gccaagccac cattgggtgt tttcttcgcc 1440
ggtgttgctc caagattgca accaagattt tactccatct cttcttctcc aaagattgct 1500
gaaaccagaa ttcacgttac ctgtgccttg gtctacgaaa agatgccaac cggtagaatt 1560
cacaagggtg tttgttccac ctggatgaag aacgctgttc catacgaaaa gtctgaaaac 1620
tgttcttctg ctccaatctt cgtccgtcaa tccaacttca agttgccatc tgactccaag 1680
gtcccaatca tcatgatcgg tccaggtact ggtttagctc cattcagagg tttcttgcaa 1740
gaaagattgg ccttagttga atctggtgtc gaattgggtc cttctgtttt gttcttcggt 1800
tgtagaaacc gtcgtatgga cttcatctac gaagaagaat tgcaaagatt tgtcgaatct 1860
ggtgctttgg ctgaattgtc cgttgctttc tctcgtgaag gtccaaccaa agaatacgtt 1920
caacacaaga tgatggacaa agcctccgac atctggaaca tgatctccca aggtgcttac 1980
ttgtacgttt gtggtgatgc taaaggtatg gccagagatg tccacagatc tttacatacc 2040
attgcccaag aacaaggttc catggactcc accaaggctg aaggtttcgt taagaacttg 2100
caaacttctg gtcgttactt gagagatgtt tgg 2133

<210> SEQ ID NO 52
<211> LENGTH: 301
<212> TYPE: DNA
<213> ORGANISM: Artificial sequence
<220> FEATURE:
<223> OTHER INFORMATION: Sc Pdc1 terminator

<400> SEQUENCE: 52
agcgatttaa tctctaatta ttagttaaag ttttataagc atttttatgt aacgaaaaat 60
aaattggttc atattattac tgcactgtca cttaccatgg aaagaccaga caagaagttg 120
ccgacagtct gttgaattgg cctggttagg cttaagtctg ggtccgcttc tttacaaatt 180
tggagaattt ctcttaaacg atatgtatat tcttttcgtt ggaaaagatg tcttccaaaa 240
aaaaaaccga tgaattagtg gaaccaagga aaaaaaaaga ggtatccttg attaaggaac 300
a 301

<210> SEQ ID NO 53
<211> LENGTH: 1000
<212> TYPE: DNA
<213> ORGANISM: Artificial sequence
<220> FEATURE:
<223> OTHER INFORMATION: Kl prom 3 promoter

<400> SEQUENCE: 53
gagcctgtcc aagcaaatgc cttctcataa atggtgccaa agacccgcaa gcccaaagca 60
attacccccc aaaaagaaat gatatagtgc aagatacgta tatgaccatg acttgactag 120
gtgaaacagt gcagaaacag ccgcacaaaa gcagccctaa ccctcagagt cgattttact 180
ctttcaggta ataaagcctc gacatcaatt ttagacagaa gccaggctgg cctcgagatt 240
atagccatag gcaagcaaga ggagagaagg ggaggccccc catgggggc ctcccccccg 300 ctgtcaaggt ttggcagaac ctagcttcat taggccacta gcccagccta aaacgtcaac 360
gggcaggagg aacactccca caagacggcg tagtattctc gattcataac cattttctca 420
atcgaattac acagaacaca ccgtacaaac ctctctatca taactactta atagtcacac 480

-continued

```
acgtactcgt ctaaatacac atcatcgtcc tacaagttca tcaaagtgtt ggacagacaa    540

ctataccagc atggatctct tgtatcggtt cttttctccc gctctctcgc aataacaatg    600

aacactgggt caatcatagc ctacacaggt gaacagagta gcgtttatac agggtttata    660

cggtgattcc tacggcaaaa atttttcatt tctaaaaaaa aaaagaaaaa tttttctttc    720

caacgctaga aggaaaagaa aaatctaatt aaattgattt ggtgattttc tgagagttcc    780

ctttttcata tatcgaattt tgaatataaa aggagatcga aaaaattttt ctattcaatc    840

tgttttctgg ttttatttga tagttttttt gtgtattatt attatggatt agtactggtt    900

tatatgggtt tttctgtata acttcttttt attttagttt gtttaatctt attttgagtt    960

acattatagt tccctaactg caagagaagt aacattaaaa                          1000


<210> SEQ ID NO 54
<211> LENGTH: 1443
<212> TYPE: DNA
<213> ORGANISM: Stevia rebaudiana

<400> SEQUENCE: 54

atggacgcta tggccaccac tgaaaagaag cctcacgtta tctttattcc attcccagct     60

caatctcata tcaaggctat gttgaaattg gctcaattat tgcaccacaa gggtttgcaa    120

atcacttttg tcaacaccga cttcattcac aaccaattct tggaatcttc tggtcctcac    180

tgtttggacg gtgctccagg tttcagattc gaaaccattc cagatggtgt ttcccactct    240

ccagaagcct ccatcccaat cagagaatcc ttgttgagat ctattgaaac caacttcttg    300

gaccgtttca tcgatttggt taccaaattg ccagacccac caacctgtat catttctgac    360

ggtttcttgt ccgttttcac catcgatgct gccaagaaat tgggtattcc agtcatgatg    420

tactggactt tggctgcttg tggtttcatg ggtttctacc atattcactc tttgattgaa    480

aagggtttcg ctccattaaa ggatgcttct tacttgacca acggttactt ggacaccgtc    540

attgactggg ttccaggtat ggaaggtatc agattgaaag atttcccatt ggactggtct    600

actgacttga atgacaaggt cttgatgttc actactgaag ctccacaaag atctcataag    660

gtttctcacc acatcttcca cactttcgat gaattagaac catctatcat caagactcta    720

tccttgagat acaaccatat ctacaccatt ggtccattac aattgttgtt ggaccaaatc    780

ccagaagaaa agaagcaaac cggtatcact tctttgcacg gttactcttt agtcaaggaa    840

gaaccagaat gtttccaatg gttacaatcc aaggaaccaa actctgttgt ctacgttaac    900

tttggttcca ccactgttat gtccttggaa gatatgactg aatttggttg ggtttggct     960

aactctaacc actacttctt atggatcatc agatctaact tggtcattgg tgaaaacgcc   1020

gttttgcctc cagaattgga agaacacatc aagaagagag gtttcattgc ttcctggtgt   1080

tctcaagaaa aggtcttgaa gcacccatct gttggtggtt tcttgaccca ctgtggttgg   1140

ggttccacca ttgaatccct atctgctggt gttccaatga tctgttggcc atactcctgg   1200

gaccaattga ctaactgtcg ttacatctgt aaggaatggg aagttggttt ggaaatgggt   1260

actaaggtca agagagatga agtcaagaga ttagtccaag aattgatggg tgaaggtggt   1320

cacaagatga gaaacaaagc caaggactgg aaggaaaagg ccagaattgc tattgctcca   1380

aacggttctt cctccttgaa catcgataaa atggttaagg aaatcactgt cttggctcga   1440

aac                                                                 1443


<210> SEQ ID NO 55
<211> LENGTH: 301
```

<212> TYPE: DNA
<213> ORGANISM: Artificial sequence
<220> FEATURE:
<223> OTHER INFORMATION: Sc TDH1 terminator

<400> SEQUENCE: 55
aataaagcaa tcttgatgag gataatgatt ttttttgaa tatacataaa tactaccgtt 60
tttctgctag attttgtgaa gacgtaaata agtacatatt actttttaag ccaagacaag 120
attaagcatt aactttaccc ttttctcttc taagtttcaa tactagttat cactgtttaa 180
aagttatggc gagaacgtcg gcggttaaaa tatattaccc tgaacgtggt gaattgaagt 240
tctaggatgg tttaaagatt tttcctttt gggaaataag taaacaatat attgctgcct 300
t 301

<210> SEQ ID NO 56
<211> LENGTH: 1000
<212> TYPE: DNA
<213> ORGANISM: Artificial sequence
<220> FEATURE:
<223> OTHER INFORMATION: Kl prom 2 promoter

<400> SEQUENCE: 56
gagcctgtcc aagcaaatgc cttctcataa atggtgccaa agacccgcaa gcccaaagca 60
attacccccc aaaaagaaat gatatagtgc aagatacgta tatgaccatg acttgactag 120
gtgaaacagt gcagaaacag ccgcacaaaa gcagccctaa ccctcagagt cgattttact 180
ctttcaggta ataaagcctc gacatcaatt ttagacagaa gccaggctgg cctcgagatt 240
atagccatag gcaagcaaga ggagagaagg ggaggccccc catggggggc ctcccccccg 300
ctgtcaaggt ttggcagaac ctagcttcat taggccacta gcccagccta aaacgtcaac 360
gggcaggagg aacactccca caagacggcg tagtattctc gattcataac cattttctca 420
atcgaattac acagaacaca ccgtacaaac ctctctatca taactactta atagtcacac 480
acgtactcgt ctaaatacac atcatcgtcc tacaagttca tcaaagtgtt ggacagacaa 540
ctataccagc atggatctct tgtatcggtt cttttctccc gctctctcgc aataacaatg 600
aacactgggt caatcatagc ctacacaggt gaacagagta gcgtttatac agggtttata 660
cggtgattcc tacggcaaaa atttttcatt tctaaaaaaa aaaagaaaaa tttttctttc 720
caacgctaga aggaaaagaa aaatctaatt aaattgattt ggtgattttc tgagagttcc 780
ctttttcata tatcgaattt tgaatataaa aggagatcga aaaaattttt ctattcaatc 840
tgttttctgg ttttatttga tagtttttt gtgtattatt attatggatt agtactggtt 900
tatatgggtt tttctgtata acttcttttt attttagttt gtttaatctt attttgagtt 960
acattatagt tccctaactg caagagaagt aacattaaaa 1000

<210> SEQ ID NO 57
<211> LENGTH: 1380
<212> TYPE: DNA
<213> ORGANISM: Stevia rebaudiana

<400> SEQUENCE: 57
atggctgaac aacaaaagat caagaaatct ccacacgtct tgttgattcc attcccattg 60
caaggtcaca tcaacccatt catccaattc ggtaagagat tgatttccaa gggtgtcaag 120
accactttag tcaccactat tcacacttta aactccactt taaaccactc taacactact 180
accacctcta ttgaaatcca agccatttct gacggttgtg acgaaggtgg tttcatgtct 240

-continued

```
gctggtgaat cttacttgga aactttcaag caagtcggtt ccaagtcttt ggctgatttg    300
atcaagaaat tgcaatccga aggtactacc atcgatgcta tcatctacga ctccatgact    360
gaatgggttt tggatgttgc cattgaattt ggtattgacg gtggttcttt cttcacccaa    420
gcctgtgttg ttaactcttt gtactaccac gtccacaagg gtttgatctc tctaccatta    480
ggtgaaaccg tttccgtccc aggtttccca gtcttgcaaa gatgggaaac tccattgatc    540
ttacaaaacc atgaacaaat ccaatctcca tggtcccaaa tgttgtttgg tcaattcgct    600
aacattgacc aagctagatg ggttttcacc aactctttct acaagttgga agaagaagtc    660
attgaatgga ccagaaagat ctggaacttg aaggttatcg gtccaactct accatccatg    720
tacttggaca agagattgga tgacgacaag gacaacggtt tcaacttgta caaggctaac    780
catcacgaat gtatgaactg gttggatgac aagccaaagg aatctgttgt ttacgttgct    840
ttcggttctt tggtcaagca tggtccagaa caagttgaag aaatcaccag agctttgatt    900
gactccgatg ttaacttctt atgggttatc aagcacaagg aagaaggtaa attgccagaa    960
aacttgtctg aagttatcaa gaccggtaag ggtttgattg ttgcttggtg taagcaattg   1020
gatgttttgg ctcacgaatc cgtcggttgt ttcgtcactc actgtggttt caactctact   1080
ttggaagcta tctccttggg tgttccagtt gttgccatgc ctcaattctc tgaccaaacc   1140
accaacgcca aattgttgga tgaaatcttg ggtgtcggtg tccgtgtcaa ggctgatgaa   1200
aacggtattg ttagaagagg taacttagct tcctgtatca agatgatcat ggaagaagaa   1260
cgtggtgtca ttatcagaaa gaatgctgtc aaatggaagg acttggctaa ggttgctgtc   1320
cacgaaggtg gttcctctga caatgacatt gttgaatttg tctctgaatt gatcaaagcg   1380
```

<210> SEQ ID NO 58
<211> LENGTH: 1374
<212> TYPE: DNA
<213> ORGANISM: Stevia rebaudiana

<400> SEQUENCE: 58

```
atggaaaaca agactgaaac cactgttaga agaagaagaa gaatcatctt attcccagtt     60
ccattccaag gtcacattaa cccaatcttg caattggcta acgtcttata ctccaagggt    120
ttctccatca ccatcttcca caccaacttc aacaaaccta aaacttccaa ctacccacac    180
ttcaccttca gatttatctt ggacaacgac ccacaagatg aaagaatttc taacttgcca    240
acccatggtc cattggccgg tatgagaatt ccaatcatca acgaacacgg tgctgacgaa    300
ttgagaagag aattggaatt gttgatgttg gcttctgaag aagatgaaga agtctcttgt    360
ttgatcactg atgctttatg gtactttgct caatctgttg ctgactcttt gaacttgaga    420
agattagtct tgatgacctc ttctttgttc aacttccacg ctcacgtttc tctaccacaa    480
tttgatgaat tgggttactt ggacccagat gacaagacca gattggaaga acaagcctcc    540
ggtttcccaa tgttgaaggt caaggatatc aagtctgcct actccaactg gcaaatcttg    600
aaggaaattt tgggtaagat gatcaagcaa accaaggctt cttctggtgt catctggaac    660
tccttcaagg aattggaaga atctgaattg gaaaccgtca tcagagaaat tccagctcca    720
tctttcttga ttccattacc aaagcatttg actgcttcct cctcttctct attggaccac    780
gacagaactg ttttccaatg gttggaccaa caaccaccat cttccgtctt atacgtttcc    840
tttggttcca cttctgaagt tgacgaaaag gacttcttgg aaattgctcg tggtttggtt    900
gactccaagc aatctttctt atgggttgtc agaccaggtt tcgtcaaggg ttccacctgg    960
gttgaacctt tgccagacgg tttcttgggt gaaagaggta gaattgtcaa atgggttcca   1020
```

caacaagaag ttttggctca cggtgccatt ggtgctttct ggactcactc tggttggaac 1080
tctactttgg aatccgtttg tgaaggtgtt ccaatgattt tctctgactt cggtttggac 1140
caaccattga atgctcgtta catgtccgat gttttgaagg ttggtgtcta cttggaaaac 1200
ggttgggaac gtggtgaaat tgctaacgcc atcagaagag tcatggtcga tgaagaaggt 1260
gaatacatca gacaaaatgc tcgtgtcttg aaacaaaagg ctgatgtttc tttgatgaag 1320
ggtggttctt cttacgaatc tttggaatct ttggtttcct acatctccag tctc 1374

<210> SEQ ID NO 59
<211> LENGTH: 602
<212> TYPE: DNA
<213> ORGANISM: Artificial sequence
<220> FEATURE:
<223> OTHER INFORMATION: Sc Eno1 terminator

<400> SEQUENCE: 59
aagcttttga ttaagccttc tagtccaaaa aacacgtttt tttgtcattt atttcatttt 60
cttagaatag tttagtttat tcattttata gtcacgaatg ttttatgatt ctatataggg 120
ttgcaaacaa gcatttttca ttttatgtta aaacaatttc aggtttacct tttattctgc 180
ttgtggtgac gcgtgtatcc gcccgctctt ttggtcaccc atgtatttaa ttgcataaat 240
aattcttaaa agtggagcta gtctatttct atttacatac ctctcatttc tcatttcctc 300
caagcttttg attaagcctt ctagtccaaa aaacacgttt ttttgtcatt tatttcattt 360
tcttagaata gtttagttta ttcattttat agtcacgaat gttttatgat tctatatagg 420
gttgcaaaca agcatttttc attttatgtt aaaacaattt caggtttacc ttttattctg 480
cttgtggtga cgcgtgtatc cgcccgctct tttggtcacc catgtattta attgcataaa 540
taattcttaa aagtggagct agtctatttc tatttacata cctctcattt ctcatttcct 600
cc 602

<210> SEQ ID NO 60
<211> LENGTH: 600
<212> TYPE: DNA
<213> ORGANISM: Saccharomyces cerevisiae

<400> SEQUENCE: 60
ccgcggaacc gccagatatt cattacttga cgcaaaagcg tttgaaataa tgacgaaaaa 60
gaaggaagaa aaaaaaagaa aaataccgct tctaggcggg ttatctactg atccgagctt 120
ccactaggat agcacccaaa cacctgcata tttggacgac ctttacttac accaccaaaa 180
accactttcg cctctcccgc ccctgataac gtccactaat tgagcgatta cctgagcggt 240
cctcttttgt ttgcagcatg agacttgcat actgcaaatc gtaagtagca acgtgtcaag 300
gtcaaaactg tatggaaacc ttgtcacctc acttaattct agctagccta ccctgcaagt 360
caagaggtgt ccgtgattcc tagccacctc aaggtatgcc tctccccgga aactgtggcc 420
ttttctggca cacatgatct ccacgatttc aacatataaa tagcttttga taatggcaat 480
attaatcaaa tttattttac ttctttcttg taacatctct cttgtaatcc cttattcctt 540
ctagctattt ttcataaaaa accaagcaac tgcttatcaa cacacaaaca ctaaatcaaa 600

<210> SEQ ID NO 61
<211> LENGTH: 301
<212> TYPE: DNA
<213> ORGANISM: Kluyveromyces lactis

<400> SEQUENCE: 61

```
aattactctt ttaagttaac gaacgctttt gatgagacta acgatatttc aagtgattcc     60
atttttttact tctaagtttt tatcaccttt atcttaacca ttctatgcca gtctttgctt    120
tatggacttt gattcaaatt atgaagggaa gtttttacgc caaataaaaa ctactacaac    180
aaattattaa aaaaaatgac gaataatatg aagtgtctaa cgactgccaa aattattcat    240
tccttttttta tacacataac catttcactt catttactgg tttgagtggt ttattacgtc    300
g                                                                     301
```

<210> SEQ ID NO 62
<211> LENGTH: 803
<212> TYPE: DNA
<213> ORGANISM: Yarrowia lipolytica

<400> SEQUENCE: 62

```
taccaaccac agattacgac ccattcgcag tcacagttca ctagggtttg ggttgcatcc     60
gttgagagtg gtttgttttt aaccttctcc atgtgctcac tcaggttttg ggttcagatc    120
aaatcaaggc gtgaaccact gtttgaggac aaatgtgaca caaccaacca gtgtcagggg    180
caagtccgtg acaaagggga agatacaatg caattactga cagttacgga ctgcctcgat    240
gccctaacct tgccccaaaa taagacaact gtcctcgttt aagcgcaacc ctattcagcg    300
tcacgtcata atagcgtttg gatagcacta gtctatgagg agcgttttat gttgcggtga    360
gggcgattgg tgctcatatg ggttcaattg aggtggtgga acgagcttag tcttcaattg    420
aggtgcgagc gacacaattg ggtgtcacgt ggcctaattg acctcggatc gtggagtccc    480
cagttataca gcaaccacga ggtgcatgag taggagacgt caccagacaa tagggttttt    540
ttggactgga gagggtaggg caaaagcgct caacgggctg tttggggagc tatgggggag    600
gaattggcga tatttgtgag gttgacggct ccgatttgcg tgttttgtcg cttctgcatc    660
tccccatacc catatcttcc ctccccacct ctttccacga taattttacg gatcagcaat    720
aaggttcctt ctcctagttt ccacgtccat atatatctat gctgcgtcgt ccttttcgtg    780
acatcaccaa aacacataca aaa                                            803
```

<210> SEQ ID NO 63
<211> LENGTH: 995
<212> TYPE: DNA
<213> ORGANISM: Yarrowia lipolytica

<400> SEQUENCE: 63

```
ctgtacctgc tgtggaccac gcacggcgga acgtaccgta caaatatttt cttgctcaca     60
tgactctctc tcggccgcgc acgccggtgg caaattgctc ttgcattggc tctgtctcta    120
gacgtccaaa ccgtccaaag tggcagggtg acgtgatgcg acgcacgaag gagatggccc    180
ggtggcgagg aaccggacac ggcgagccgg cgggaaaaaa ggcggaaaac gaaaagcgaa    240
gggcacaatc tgacggtgcg gctgccacca acccaaggag gctattttgg gtcgctttcc    300
atttcacatt cgccctcaat ggccactttg cggtggtgaa catggtttct gaaacaaccc    360
cccagaatta gagtatattg atgtgtttaa gattgggttg ctatttggcc attgtggggg    420
agggtagcga cgtggaggac attccagggc gaattgagcc tagaaagtgg taccattcca    480
accgtctcag tcgtccgaat tgatcgctat aactatcacc tctctcacat gtctacttcc    540
ccaaccaaca tccccaacct cccccacact aaagttcacg ccaataatgt aggcactctt    600
tctgggtgtg ggacagcaga gcaatacgga ggggagatta cacaacgagc cacaattggg    660
```

```
gagatggtag ccatctcact cgacccgtcg acttttggca acgctcaatt acccaccaaa    720

tttgggctgg agttgagggg accgtgttcc agcgctgtag gaccagcaac acacacggta    780

tcaacagcaa ccaacgcccc cgctaatgca cccagtactg cgcaggtgtg ggccaggtgc    840

gttccagatg cgagttggcg aaccctaagc cgacagtgta ctttttggga cgggcagtag    900

caatcgtggg cggagacccc ggtgtatata aaggggtgga gaggacggat tattagcacc    960

aacacacaca cttatactac atgctagcca caaaa                               995
```

<210> SEQ ID NO 64
<211> LENGTH: 1004
<212> TYPE: DNA
<213> ORGANISM: Yarrowia lipolytica

<400> SEQUENCE: 64

```
gtcagaaggg gcagctctaa acgaagaact gcggtcaggt gacacaactt tttccatctc     60

agggtgtgtc gcgtgtgctt catccaaact ttagttgggg ttcgggttcg cgcgagatga    120

tcacgtgccc tgatttggtg tcgtcccccg tcgcgctgcg cacgtgattt atttatttcc    180

ggtggctgct gtctacgcgg ggccttctct gcccttctgt ttcaaccttc gggcggttct    240

cgtaaccagc agtagcaatc catttcgaaa ctcaaagagc taaaaacgtt aaacctcagc    300

agtcgctcga cgaatgggct gcggttggga agcccacgag gcctatagcc agagcctcga    360

gttgacagga gcccagacgc cttttccaac ggcaactttt atataaaatg gcaatgtatt    420

catgcaattg cggccgtgtc aggttggaga cactggacca cactctccat tgcttcctga    480

ggagatggat cattgctagt gcatctacgc gcagcaatcc cgcaagctcg acaaccgtag    540

atgggctttg gtgggccaat caattacgca acccgcacgt taaattgtat gaggaaggaa    600

ggccacggta caaagtgggt ggtcttcacc cagtggttgt tggtggcgtc atgcagacca    660

tgcattgggg atagcacagg gttggggtgt cttgtggact caatgggtga aaggagatgg    720

aaaagggcgg tgaaaagtgg tagaatcgaa atccctgacg tcaatttata aagtaaaatg    780

cgtttctgcc attttgctcc cctccttctt tcgcaatcgc ctccccaaaa gttgtcgtgg    840

cagtacacat gcttgcatac aatgaagcta atccggcttg ctcagtagtt gctatatcca    900

ggcatggtgt gaaacccctc aaagtatata taggagcggt gagccccagt ctggggtctt    960

ttctctccat ctcaaaacta ctttctcaca tgctagccac aaaa                    1004
```

<210> SEQ ID NO 65
<211> LENGTH: 1422
<212> TYPE: DNA
<213> ORGANISM: Yarrowia lipolytica

<400> SEQUENCE: 65

```
atttcttgtg tgtgcggcaa acgtagcaat tgcaactgca taaacgatga ttgtaaaagt     60

atcacacttt gctcagacag gttagattca cctggtacga gggcagtgtc ttaaaggttc    120

catctacctc ggcccttgtt tcttgaagag tggtcaatat gtgttttata cagctgaaat    180

ttcccctgta tgttgagatc gtgtatattg gtcataatct gggctcttta gtcgatccca    240

gttttctcgg gcaagttttt ttctccacaa agtaccgctg gaaaactcta tgtgacttgt    300

tgacagatta cttgggttat ctgcgggata tgtcttggat aggcaaccgg gcatatatca    360

ccgggcggac tgttggttct gtacgtacat acagcacttt gagctcatgt ctcacacgca    420

accatggtgc gtggaggctt tggcatcctt tctacttgta gtggctatag tacttgcagt    480
```

| | |
|---|---|
| ccaagcaaac atgagtatgt gcttgtatgt actgaaaccc gtctacggta atattttaga | 540 |
| gtgtggaact atgggatgag tgctcattcg atactatgtt gtcacccgat ttgccgtttg | 600 |
| cgaggtaaga cacattcggt ggttcaggcg gctacttgta tgtagcatcc acgttcatgt | 660 |
| tttgtggatc agattaatgg tatggatatg cacggggcgt ttccccggta acgtgtaggc | 720 |
| agtccagtgc aacccagaca gctgagctct ctatagccgt gcgtgtgcgg tcatatcacg | 780 |
| ctacacttag ctacagaata aagctcggta gcgccaacag cgttgacaaa tagctcaagg | 840 |
| gcgtggagca cagggtttag gaggttttaa tgggcgagaa ggcgcgtaga tgtagtcttc | 900 |
| ctcggtccca tcggtaatca cgtgtgtgcc gatttgcaag acgaaaagcc acgagaataa | 960 |
| accgggagag gggatggaag tccccgaaca gcaaccagcc cttgccctcg tggacataac | 1020 |
| ctttcacttg ccagaactct aagcgtcacc acggtataca agcgcacgta gaagattgtg | 1080 |
| gaagtcgtgt tggagactgt tgatttgggc ggtggagggg ggtatttgag agcaagtttg | 1140 |
| agatttgtgc cattgagggg gaggttattg tggccatgca gtcggatttg ccgtcacggg | 1200 |
| accgcaacat gcttttcatt gcagtccttc aactatccat ctcacctccc ccaatggctt | 1260 |
| ttaactttcg aatgacgaaa gcacccccct ttgtacagat gactatttgg gaccaatcca | 1320 |
| atagcgcaat tgggtttgca tcatgtataa aaggagcaat cccccactag ttataaagtc | 1380 |
| acaagtatct cagtataccc gtctaaccac acatttatca cc | 1422 |

<210> SEQ ID NO 66
<211> LENGTH: 865
<212> TYPE: DNA
<213> ORGANISM: Yarrowia lipolytica

<400> SEQUENCE: 66

| | |
|---|---|
| atgctcactt tgttgtcct gatgatctcc cgttatttcg ccgctcctct ggaaaccatc | 60 |
| cgcccgcaaa tcccctctgc ccatcttgac aatgcacaat gcatcattct cagcctgcat | 120 |
| gaatgcgaaa gatggcaata ttggtggagg aggcgacggc ggtaaacaat ggagatagag | 180 |
| accacaaaag agacctggag acccaaaatg gactcacgac aactccccca ctcccccact | 240 |
| ccccatctcc ccctgggcat cagttgccca tcggtatctc aactgtcgca ctagttagcg | 300 |
| caaccatcac atactttaga cgccaaacaa tgggacaact catcgcgccg aactatgggc | 360 |
| agattttaac tcgcacaaca ttaccccaac tctaaaaggt aacctcgacc ggaaaacggg | 420 |
| aagacaggat cagcaaccgt gatcgacaga atcttcaggg cactacagtt gatagacata | 480 |
| ggttatgttg gtaggtctag acgggcctcg gggaattgac cccaccagtt gcaagtcacg | 540 |
| tgcccctgat acagctagtt tagcacatct gcccactacg tctggacgca ccatggtggt | 600 |
| gccagtcgcg tgaactcaaa cacccactag cctcgggaag gattcagtta aatccgcacc | 660 |
| ttatttccaa cacaaagaag cggttggcgg acaaagaaca tgtcctttct ggggcactgt | 720 |
| acattccagg actctgttca aggtcaaata tacaaaacac agatagagaa acatagacag | 780 |
| ctgcggcctt ataaatacct gggcgcactt ctctcttttt ccctcctcat cacacattcg | 840 |
| ttcaccacta agtcactcgt tcaaa | 865 |

<210> SEQ ID NO 67
<211> LENGTH: 880
<212> TYPE: DNA
<213> ORGANISM: Yarrowia lipolytica

<400> SEQUENCE: 67

| | |
|---|---|
| aaacaaaaga gctgaaatca tatccttcag tagtagtata gtcctgttat cacagcatca | 60 |

```
attacccccg tccaagtaag ttgattggga tttttgttta cagatacagt aatatacttg    120

actatttctt tacaggtgac tcagaaagtg catgttggaa atgagccaca gaccaagaca    180

agatatgaca aaattgcact attcgatgca gaattcgacg gtgtttccat tggtgttatg    240

acattcatct gcattcatac aaaaaagtct tggtagtggt acttttgcgt tattacctcc    300

gatatctacg caccccccaa cccccctgct acagtaaaga gtgtgagtct actgtacatg    360

cttactaaac cacctactgt acagcgaaac ccctcagcaa aatcacacaa tcagctcatt    420

acaacacacc caatgacctc accacaaatt ctatacgcct tttgacgcca ttattacagt    480

agcttgcaac gccgttgtct taggttccat ttttagtgct ctattacctc acttaacccg    540

tataggcaga tcaggccatg gcactaagtg tagagctaga ggttgatatc gccacgagtg    600

ctccatcagg gctagggtgg ggttagaaat acagtccgtg cgcactcaaa aggcgtccgg    660

gttagggcat ccgataatat cgcctggact cggcgccata ttctcgactt ctgggcgcgt    720

tgtattcatc tcctccgctt cccaacactt ccacccgttt ctccatccca accaatagaa    780

tagggtaacc ttattcggga cactttcgtc atacatagtc agatatacaa gcaatgtcac    840

tctccttcgt actcgtacat acaacacaac tacattcaaa                          880
```

<210> SEQ ID NO 68
<211> LENGTH: 1000
<212> TYPE: DNA
<213> ORGANISM: Yarrowia lipolytica

<400> SEQUENCE: 68

```
caattcatgt atcgtgtcaa ttcatgtatc gtgtcaattc atgtatcgtg tcaatactta     60

tatctcaagt ggttgcatcg caaacagcca tcgcatactc cactctactc tcactgagtt    120

cactcttacc cggctccacc ttctagaagc caccaccgat ccaccgacga tgatcagtcc    180

accacttgct ctgaatgtgc gttggagctg caccatgatt gatgacgtca ccgccattca    240

gatagggcaa aagacgagcg ccaatcgcaa caatgggcga gtgtcgacga ctcccccgct    300

ctctgcggtt tcagcgactc caaccgtcgc caaaagaccg tcattttcgt ctaaagcgca    360

gcccagccca tctcttctaa aagattccag aaagataggg ttcaccaact acgcaccaat    420

atgtacagta tcgtagctac tccggcttgg ctgatctgag agatagagat ggctccgaaa    480

cgcggaaaac ggcggggtcg gaccgatcac gtgacacgta ctcatccgtc gcgccccgag    540

cgccatttca acaccaaata ctcccggtca cgtgccaccc cgcccgctct acccacgaga    600

tgtttctaca ctatacactg ccacgccgtc atacctgcag ctaggttaac attcgattaa    660

ttagtggagt caccagtgta caggactatg gcggaaaccg ggttacacaa accggcccgg    720

aatagcagca ttataccgct ggacgagatc accgtcaata aattgcgtcg ttactcggga    780

caaccattgc tcctccggct acacctgctc aaaggacttg ttccacactc ttccccagct    840

ctcccacgca aacaaagaga gcaaccttaa gtggacagct catgagcact cccctcgttt    900

gctgcccacg ctcgattata taaagaccag cggatcccct tctatttgga cttgcatcaa    960

ccaaccacaa cccacaccaa gcacacaaag cacaagaaca                         1000
```

<210> SEQ ID NO 69
<211> LENGTH: 127
<212> TYPE: DNA
<213> ORGANISM: Yarrowia lipolytica

<400> SEQUENCE: 69

-continued

```
aattaacaga tagtttgccg gtgataattc tcttaacctc ccacactcct ttgacataac     60

gatttatgta acgaaactga aatttgacca gatattgttg taaatagaaa atctggcttg    120

taggtgg                                                              127


<210> SEQ ID NO 70
<211> LENGTH: 200
<212> TYPE: DNA
<213> ORGANISM: Yarrowia lipolytica

<400> SEQUENCE: 70

gtttttgat caatgatcca atggctttca catacccccc cacgcctata attaaaacac     60

agagaaatat aatctaactt aataaatatt acggagaatc tttcgagtgt tcagcagaaa    120

tatagccatt gtaacaaaag ccggctatcg accgctttat cgaagaatat ttcccgcccc    180

ccagtggcca aacgatatcg                                                200


<210> SEQ ID NO 71
<211> LENGTH: 200
<212> TYPE: DNA
<213> ORGANISM: Yarrowia lipolytica

<400> SEQUENCE: 71

ctatccgaag atcaagagcg aagcaagttg taagtccagg acatgtttcc cgcccacgcg     60

agtgatttat aacacctctc ttttttgaca cccgctcgcc ttgaaattca tgtcacataa    120

attatagtca acgacgtttg aataacttgt cttgtagttc gatgatgatc atatgattac    180

attaatagta attactgtat                                                200


<210> SEQ ID NO 72
<211> LENGTH: 200
<212> TYPE: DNA
<213> ORGANISM: Yarrowia lipolytica

<400> SEQUENCE: 72

acttcgagct aatccagtag cttacgttac ccaggggcag gtcaactggc tagccacgag     60

tctgtcccag gtcgcaattt agtgtaataa acaatatata tattgagtct aaagggaatt    120

gtagctattg tgattgtgtg attttcgtct tgctggttct tattgtgtcc cattcgtttc    180

atcctgatga ggacccctgg                                                200


<210> SEQ ID NO 73
<211> LENGTH: 200
<212> TYPE: DNA
<213> ORGANISM: Yarrowia lipolytica

<400> SEQUENCE: 73

gctatttaca gcatgtgtaa tgaggaatat aacgttgatt gaattgtttg tgaaaaatgt     60

agaaaatttc agtgaagttg tgttttctat atagtaagca cttttggtac aagtatctgc    120

acatccctgc atgttacaag cctgatcatg cagggcaata ttctgactat aaatatacct    180

cgatatttta gcaagctata                                                200


<210> SEQ ID NO 74
<211> LENGTH: 300
<212> TYPE: DNA
<213> ORGANISM: Yarrowia lipolytica

<400> SEQUENCE: 74

atgtggtgat tgctgttgtg caagcctttg ctcgttttct gctgtatgta atttaaagaa     60
```

cgattgtatg aatcgaagtc aaggtgagtg tagtttgaga agtgtaaccc cagtgtcata 120
gctgtgtact ccattcattg aagggtgtag tcgtgtttta ttgcatgagc gcctattact 180
cgtataagta actgttttgt aacacttcat gaacggagat ggtatgaaca gaagtaataa 240
tatcctggaa gtcagctgtg cccagaggtg tgtgtgggtg tggcatactt tgggacaaca 300

<210> SEQ ID NO 75
<211> LENGTH: 1503
<212> TYPE: DNA
<213> ORGANISM: Artificial sequence
<220> FEATURE:
<223> OTHER INFORMATION: tHMG CpO for Yarrowia lipolitica

<400> SEQUENCE: 75
atgacccagt ctgtgaaggt ggttgagaag cacgttccta tcgtcattga gaagcccagc 60
gagaaggagg aggacacctc ttctgaagac tccattgagc tgactgtcgg aaagcagccc 120
aagcccgtga ccgagacccg ttctctggac gacttggagg ctatcatgaa ggcaggtaag 180
accaagctcc tggaggacca cgaggttgtc aagctctctc tcgaaggcaa gctccctttg 240
tatgctcttg agaagcagct tggtgacaac acccgagctg ttggcatccg acgatctatc 300
atctcccagc agtctaatac caagactctt gagacctcaa agctccctta cctgcactac 360
gactacgacc gtgtttttgg agcctgttgc gagaacgtta ttggttacat gcctctcccc 420
gttggtgttg ctggccccat gaacattgat ggcaagaact accacattcc tatggccacc 480
actgagggtt gtcttgttgc ctcaaccatg cgaggttgca aggccatcaa cgccggtggc 540
ggtgttacca ctgtgcttac tcaggacggt atgacacgag gtccttgtgt ttccttcccc 600
tctctcaagc gggctggagc cgctaagatc tggcttgatt ccgaggaggg tctcaagtcc 660
atgcgaaagg ccttcaactc cacctctcga tttgctcgtc tccagtctct tcactctacc 720
cttgctggta acctgctgtt tattcgattc cgaaccacca ctggtgatgc catgggcatg 780
aacatgatct ccaagggcgt cgaacactct ctggccgtca tggtcaagga gtacggcttc 840
cctgatatgg acattgtgtc tgtctcgggt aactactgca ctgacaagaa gcccgcagcg 900
atcaactgga tcgaaggccg aggcaagagt gttgttgccg aagccaccat ccctgctcac 960
attgtcaagt ctgttctcaa aagtgaggtt gacgctcttg ttgagctcaa catcagcaag 1020
aatctgatcg gtagtgccat ggctggctct gtgggaggtt tcaatgcaca cgccgcaaac 1080
ctggtgaccg ccatctacct tgccactggc caggatcctg ctcagaatgt cgagtcttcc 1140
aactgcatca cgctgatgag caacgtcgac ggtaacctgc tcatctccgt ttccatgcct 1200
tctatcgagg tcggtaccat tggtggaggt actattttgg agccccaggg tgctatgctg 1260
gagatgcttg gcgtgcgagg tcctcacatc gagacccccg gtgccaacgc ccaacagctt 1320
gctcgcatca ttgcttctgg agttcttgca gcggagcttt cgctgtgttc tgctcttgct 1380
gccggccatc ttgtgcaaag tcatatgacc cacaaccgtt cccaggctcc tactccggcc 1440
aagcagtctc aggccgatct gcagcgtctc caaaacggtt cgaatatctg cattcggtca 1500
tag 1503

<210> SEQ ID NO 76
<211> LENGTH: 984
<212> TYPE: DNA
<213> ORGANISM: Artificial sequence
<220> FEATURE:
<223> OTHER INFORMATION: GGS CpO for Yarrowia lipolitica

<400> SEQUENCE: 76
atggattata acagcgcgga tttcaaggag atctggggca aggccgccga caccgcgctg 60
ctgggaccgt acaactacct cgccaacaac cggggccaca acatcagaga acacttgatc 120
gcagcgttcg gagcggttat caaggtggac aagagcgatc tcgaaaccat ttcgcacatc 180
accaagattt tgcataactc gtcgctgctt gttgatgacg tggaagacaa ctcgatgctc 240
cgacgaggcc tgccggcagc ccattgtctg tttggagtcc cccaaaccat caactccgcc 300
aactacatgt actttgtggc tctgcaggag gtgctcaagc tcaagtctta tgatgccgtc 360
tccattttca ccgaggaaat gatcaacttg catagaggtc agggtatgga tctctactgg 420
agagaaacac tcacttgccc ctcggaagac gagtatctgg agatggtggt gcacaagacc 480
ggaggactgt ttcggctggc tctgagactt atgctgtcgg tggcatcgaa acaggaggac 540
catgaaaaga tcaactttga tctcacacac cttaccgaca cactgggagt catttaccag 600
attctggatg attacctcaa cctgcagtcc acggaattga ccgagaacaa gggattctgc 660
gaagatatca gcgaaggaaa gttttcgttt ccgctgattc acagcatccg gaccaacccg 720
gataaccacg agattctcaa cattctcaaa cagcgaacaa gcgacgcttc actcaaaaag 780
tacgccgtgg actacatgag aacagaaacc aagagtttcg actactgcct caagagaatc 840
caggccatgt cactcaaggc aagttcgtac attgatgatc tcgcagcagc cggccacgat 900
gtctccaagt tgcgagccat tttgcattat tttgtgtcca cctctgactg tgaggagaga 960
aagtactttg aggatgcgca gtga 984

<210> SEQ ID NO 77
<211> LENGTH: 1446
<212> TYPE: DNA
<213> ORGANISM: Artificial sequence
<220> FEATURE:
<223> OTHER INFORMATION: UGT1 CpO for Yarrowia lipolitica

<400> SEQUENCE: 77
atggacgcca tggccaccac cgagaagaag ccccacgtca tcttcatccc cttccccgcc 60
cagtcccaca tcaaggccat gctcaagctc gcccagctcc tccaccacaa gggcctccag 120
atcacctttg tcaacaccga cttcatccac aaccagttcc tcgagtcctc cggcccccac 180
tgtctggacg gtgctcccgg tttccgattt gagactatcc ccgatggtgt ctcccactcc 240
cccgaggcct ccatccccat ccgagagtct ctgctccgat ccattgagac taacttcctc 300
gaccgattca ttgatctcgt caccaagctc cccgatcctc ccacctgtat catctccgac 360
ggtttcctgt ccgttttcac cattgatgct gccaagaagc tcggtatccc cgtcatgatg 420
tactggactc tggctgcctg tggtttcatg ggtttctacc acatccactc tctgatcgag 480
aagggctttg ctcctctcaa ggacgcctcc tacctcacca acggttacct cgacaccgtc 540
attgactggg tccccggtat ggagggtatc cgactcaagg acttcccccct cgactggtcc 600 accgacctca acgacaaggt tctcatgttc accaccgagg ctccccagcg atcccacaag 660
gtttcccacc acatcttcca caccttcgac gagctcgagc cctccatcat caagactctg 720
tctctgcgat acaaccacat ctacaccatt ggcccccctcc agctcctcct cgaccagatc 780
cccgaggaga agaagcagac cggtatcacc tctctgcacg gctactctct cgtcaaggaa 840
gagcccgagt gcttccagtg gctccagtcc aaggagccca actccgttgt ctacgtcaac 900
tttggctcca ccaccgtcat gtctctcgag gacatgaccg agtttggctg gggtctggcc 960
aactccaacc actacttcct gtggatcatc cgatccaacc tcgtcattgg cgagaacgcc 1020

-continued

```
gttctgcctc ccgagctcga ggagcacatc aagaagcgag gcttcattgc ctcttggtgc   1080

tcccaggaga aggttctcaa gcacccctcc gtcggtggtt tcctgaccca ctgcggctgg   1140

ggctccacca ttgagtctct gtccgctggt gtccccatga tctgctggcc ctactcctgg   1200

gaccagctca ccaactgccg atacatctgc aaggagtggg aggttggtct ggagatgggt   1260

accaaggtca agcgagatga ggtcaagcga ctcgtccagg agctcatggg cgagggtggt   1320

cacaagatgc gaaacaaggc caaggactgg aaggagaagg cccgaattgc cattgccccc   1380

aacggctctt cttctctcaa cattgacaag atggtcaagg agatcactgt tctcgctcga   1440

aactaa                                                              1446
```

<210> SEQ ID NO 78
<211> LENGTH: 1383
<212> TYPE: DNA
<213> ORGANISM: Artificial sequence
<220> FEATURE:
<223> OTHER INFORMATION: UGT3 CpO for Yarrowia lipolitica

<400> SEQUENCE: 78

```
atggccgagc agcagaagat caagaagtct ccccacgttc tgctcatccc cttccctctg     60

cagggccaca tcaacccctt catccagttc ggcaagcgac tcatctccaa gggtgtcaag    120

accactctgg tcaccaccat ccacaccctc aactccactc tcaaccactc caacaccacc    180

accacctcca tcgagatcca ggccatctcc gacggctgtg acgagggtgg tttcatgtct    240

gctggtgagt cttacctcga gactttcaag caggtcggtt ccaagtctct ggctgacctc    300

atcaagaagc tccagtccga gggtaccacc attgacgcca tcatctacga ctccatgacc    360

gagtgggttc tcgatgtcgc catcgagttt ggtattgacg gtggctcctt cttcacccag    420

gcctgtgtcg tcaactctct ctactaccac gtccacaagg gtctgatctc tctgcccctc    480

ggcgagactg tctccgtccc cggtttcccc gttctgcagc gatgggagac tcctctcatt    540

ctccagaacc acgagcagat ccagtccccc tggtcccaga tgctcttcgg ccagttcgcc    600

aacattgacc aggcccgatg ggttttcacc aactccttct acaagctcga ggaagaggtc    660

attgagtgga cccgaaagat ctggaacctc aaggtcattg gccccaccct cccctccatg    720

tacctcgaca agcgactcga tgacgacaag gacaacggtt tcaacctcta caaggccaac    780

caccacgagt gcatgaactg gctcgacgac aagcccaagg agtccgttgt ctacgttgcc    840

tttggctctc tggtcaagca cggccccgag caggttgagg agatcacccg agctctgatt    900

gactccgatg tcaacttcct gtgggtcatc aagcacaagg aagagggtaa gctccccgag    960

aacctgtccg aggtcatcaa gaccggcaag ggcctcattg ttgcctggtg caagcagctc   1020

gacgttctcg cccacgagtc cgtcggctgc tttgtcaccc actgcggttt caactccacc   1080

ctcgaggcta tctctctcgg tgtccccgtt gttgccatgc cccagttctc cgaccagacc   1140

accaacgcca agctcctcga tgagattctc ggtgtcggtg tccgagtcaa ggctgacgag   1200

aacggtattg tccgacgagg taacctggct tcttgtatca agatgatcat ggaggaagag   1260

cgaggtgtca tcatccgaaa gaacgccgtc aagtggaagg atctggccaa ggttgctgtc   1320

cacgagggtg gctcttccga caacgacatt gtcgagtttg tctccgagct catcaaggcc   1380

taa                                                                 1383
```

<210> SEQ ID NO 79
<211> LENGTH: 1377
<212> TYPE: DNA

-continued

<213> ORGANISM: Artificial sequence
<220> FEATURE:
<223> OTHER INFORMATION: UGT4 CpO for Yarrowia lipolitica

<400> SEQUENCE: 79

```
atggagaaca agaccgagac taccgtccga cgacgacgac gaatcattct cttccccgtc     60
cccttccagg gccacatcaa ccccattctg cagctcgcca acgttctgta ctccaagggc    120
ttctccatca ccatcttcca caccaacttc aacaagccca agacctccaa ctaccccccac    180
ttcactttcc gattcatcct cgacaacgac ccccaggacg agcgaatctc caacctgccc    240
acccacggtc ctctggctgg tatgcgaatc cccatcatca acgagcacgg tgctgacgag    300
ctccgacgag agctcgagct gctcatgctc gcctccgaag aggacgagga agtctcctgt    360
ctgatcaccg atgctctgtg gtactttgcc cagtccgtcg ccgactctct caacctgcga    420
cgactcgttc tcatgacctc ctctctgttc aacttccacg cccacgtttc tctgccccag    480
tttgacgagc tcggttacct cgaccccgat gacaagaccc gactcgagga gcaggcttcc    540
ggtttcccca tgctcaaggt caaggacatc aagtccgcct actccaactg gcagattctc    600
aaggagattc tcggcaagat gatcaagcag accaaggcct cctccggtgt catctggaac    660
tccttcaagg agctcgagga gtccgagctc gagactgtca tccgagagat ccccgctccc    720
tctttcctca tcccccctgcc caagcacctc accgcttcct cctcttctct gctcgaccac    780
gaccgaaccg tctttcagtg gctcgaccag cagcccctt cctccgtcct ctacgtttcc    840
ttcggctcca cctccgaggt cgacgagaag gacttcctcg agattgctcg aggcctcgtt    900
gactccaagc agtccttcct gtgggttgtc cgacccggct ttgtcaaggg ctccacctgg    960
gttgagcccc tgcccgatgg tttcctcggt gagcgaggcc gaattgtcaa gtgggtcccc   1020
cagcaggaag ttctggccca cggtgccatt ggtgccttct ggacccactc cggctggaac   1080
tccactctcg agtccgtctg cgagggtgtc cccatgatct tctccgactt tggcctcgac   1140
cagcccctca acgcccgata catgtccgat gttctcaagg tcggtgtcta cctcgagaac   1200
ggctgggagc gaggtgagat tgccaacgcc atccgacgag tcatggtcga cgaggaaggt   1260
gagtacatcc gacagaacgc ccgagtcctc aagcagaagg ccgatgtctc tctcatgaag   1320
ggtggttctt cttacgagtc tctcgagtct ctcgtttcct acatctcttc tttgtaa      1377
```

<210> SEQ ID NO 80
<211> LENGTH: 2232
<212> TYPE: DNA
<213> ORGANISM: Artificial sequence
<220> FEATURE:
<223> OTHER INFORMATION: tCPS_SR CpO for Yarrowia lipolitica

<400> SEQUENCE: 80

```
atgtgcaagg ctgtttccaa ggagtactcc gatctgctcc agaaggacga ggcctctttc     60
accaagtggg acgacgacaa ggtcaaggac cacctcgaca ccaacaagaa cctctacccc    120
aacgacgaga tcaaggagtt tgtcgagtcc gtcaaggcca tgttcggctc catgaacgac    180
ggcgagatta atgtctctgc ttacgacacc gcctgggttg ctctggtcca ggatgtcgac    240
ggttccggct ctcctcagtt cccttcctct ctcgagtgga tcgccaacaa ccagctgtcc    300
gacggttctt ggggtgacca cctgctcttc tctgctcacg accgaatcat caacaccctg    360
gcctgtgtca ttgctctgac ctcttggaac gtccacccct ccaagtgcga gaagggtctg    420
aacttcctcc gagagaacat ctgcaagctc gaggacgaga acgccgagca catgcccatt    480
ggcttcgagg tcaccttccc ctctctgatt gacattgcca agaagctcaa cattgaggtc    540
```

```
cccgaggaca cccccgctct caaggagatc tacgctcgac gagacatcaa gctcaccaag    600
atccccatgg aggttctcca caaggtcccc accactctcc tccactctct cgagggtatg    660
cccgatctcg agtgggagaa gctgctcaag ctgcagtgca aggacggctc tttcctcttc    720
tcccccctctt ccactgcctt cgccctcatg cagaccaagg acgagaagtg tctccagtac    780
ctcaccaaca ttgtcaccaa gttcaacggt ggtgtcccca acgtctaccc cgttgacctc    840
tttgagcaca tctgggttgt tgaccgactc cagcgactcg gtatcgcccg atacttcaag    900
tccgagatca aggactgtgt cgagtacatc aacaagtact ggaccaagaa cggtatctgc    960
tgggcccgaa acacccacgt ccaggacatt gacgacaccg ccatgggctt ccgagttctg   1020
cgagcccacg gctacgatgt cacccccgat gtctttcgac agtttgagaa ggacggcaag   1080
tttgtctgtt tcgccggtca gtccacccag gccgtcaccg gtatgttcaa cgtctaccga   1140
gcttctcaga tgctcttccc cggtgagcga atcctcgagg acgccaagaa gttctcctac   1200
aactacctca aggagaagca gtccaccaac gagctgctcg acaagtggat cattgccaag   1260
gatctgcccg gtgaggttgg ctacgccctc gacatcccct ggtacgcctc tctgccccga   1320
ctggagactc gatactacct cgagcagtac ggtggtgagg acgatgtctg gatcggtaag   1380
accctgtacc gaatgggcta cgtttccaac aacacctacc tcgagatggc caagctcgac   1440
tacaacaact acgttgccgt cctccagctc gagtggtaca ccatccagca gtggtacgtc   1500
gacattggta tcgagaagtt cgagtccgac aacatcaagt ccgtccttgt ctcctactac   1560
ctcgctgctg cctccatctt cgagcccgag cgatccaagg agcgaattgc ctgggccaag   1620
accaccatcc tcgtcgacaa gatcacctcc atcttcgact cctcccagtc ctccaaggaa   1680
gatatcaccg ccttcattga caagttccga aacaagtcct cctccaagaa gcactccatc   1740
aacggcgagc cctggcacga ggtcatggtt gctctcaaga aaactctcca cggctttgcc   1800
ctcgacgctc tgatgaccca ctctcaggac atccaccccc agctccacca ggcctgggag   1860
atgtggctca ccaagctcca ggacggtgtt gatgtcactg ctgagctcat ggtccagatg   1920
atcaacatga ccgccggccg atgggtttcc aaggagctcc tcacccaccc ccagtaccag   1980
cgactctcca ctgtcaccaa ctctgtctgc cacgacatca ccaagctcca caacttcaag   2040
gagaactcca ccaccgtcga ctccaaggtc caggagctgg tccagctcgt tttctccgac   2100
acccccgatg atctcgacca ggacatgaag cagaccttcc tgactgtcat gaaaactttc   2160
tactacaagg cctggtgcga ccccaacacc atcaacgacc acatctccaa ggtctttgag   2220
attgtgattt aa                                                       2232
```

```
<210> SEQ ID NO 81
<211> LENGTH: 2274
<212> TYPE: DNA
<213> ORGANISM: Artificial sequence
<220> FEATURE:
<223> OTHER INFORMATION: tKS-SR CpO for Yarrowia lipolitica

<400> SEQUENCE: 81

atgacctccc acggcggcca gaccaacccc accaacctca tcattgacac caccaaggag     60
cgaatccaga agcagttcaa gaacgtcgag atctccgttt cctcctacga caccgcctgg    120
gtcgccatgg tcccctctcc caactccccc aagtctccct gcttccccga gtgtctcaac    180
tggctcatca acaaccagct caacgacggc tcttggggtc tggtcaacca cacccacaac    240
cacaaccacc ccctcctcaa ggactctctc tcttccactc tcgcctgcat tgttgctctc    300
```

-continued

```
aagcgatgga acgttggcga ggaccagatc aacaagggtc tgtctttcat tgagtccaac    360

ctcgcctccg ccaccgagaa gtcccagccc tcccccattg gctttgatat catcttcccc    420

ggtctgctcg agtacgccaa gaacctcgat atcaacctgc tctccaagca gaccgacttc    480

tctctcatgc tgcacaagcg agagctcgag cagaagcgat gccactccaa cgagatggac    540

ggctacctgg cctacatttc cgagggtctg ggtaacctct acgactggaa catggtcaag    600

aagtaccaga tgaagaacgg ttccgttttc aactccccct ctgccaccgc tgctgccttc    660

atcaaccacc agaaccccgg ctgtctcaac tacctcaact ctctgctcga caagtttggt    720

aacgccgtcc ccactgtcta cccccacgat ctcttcatcc gactctccat ggtcgacacc    780

attgagcgac tcggtatttc ccaccacttc cgagtcgaga tcaagaacgt tctcgatgag    840

acttaccgat gctgggttga gcgagatgag cagatcttca tggacgttgt cacctgtgct    900

ctggccttcc gactcctccg aatcaacggt tacgaggttt cccccgaccc cctcgccgag    960

atcaccaacg agctggctct caaggacgag tacgccgccc tcgagactta ccacgcttct   1020

cacattctgt accaagagga tctgtcctcc ggcaagcaga ttctcaagtc cgccgacttc   1080

ctcaaggaga tcatctccac tgactccaac cgactctcca agctcatcca caaggaagtc   1140

gagaacgctc tcaagttccc catcaacacc ggtctggagc gaatcaacac ccgacgaaac   1200

atccagctct acaacgtcga caacacccga attctcaaga ccacctacca ctcttccaac   1260

atctccaaca ccgactacct gcgactcgcc gtcgaggact tctacacctg ccagtccatc   1320

taccgagagg agctcaaggg tctggagcga tgggttgtcg agaacaagct cgaccagctc   1380

aagtttgccc gacaaaagac tgcctactgc tacttctccg ttgctgccac cctctcttct   1440

cccgagctct ccgacgcccg aatctcttgg gccaagaacg gtatcctgac cactgttgtc   1500

gacgacttct ttgacattgg tggcaccatt gacgagctga ccaacctcat ccagtgcgtc   1560

gagaagtgga acgtcgacgt tgacaaggac tgttgttccg agcacgtccg aatcctcttc   1620

ctggctctca aggacgccat ctgctggatc ggtgacgagg ccttcaagtg gcaggctcga   1680

gatgtcactt cccacgtcat ccagacctgg ctcgagctca tgaactccat gctgcgagag   1740

gccatctgga cccgagatgc ctacgtcccc accctcaacg agtacatgga gaacgcctac   1800

gtcagctttg ctctcggtcc cattgtcaag cccgccatct actttgtcgg tcccaagctg   1860

tccgaggaga ttgtcgagtc ctccgagtac cacaacctct tcaagctcat gtccacccag   1920

ggccgactcc tcaacgatat ccactccttc aagcgagagt tcaaggaagg taagctcaac   1980

gccgttgctc tgcacctgtc caacggtgag tccggcaagg tcgaggaaga ggtcgtcgag   2040

gagatgatga tgatgatcaa gaacaagcga aaggagctca tgaagctcat cttcgaggag   2100

aacggctcca ttgtcccccg agcctgcaag gacgccttct ggaacatgtg ccacgtcctc   2160

aacttcttct acgccaacga cgacggtttc accggcaaca ccattctcga caccgtcaag   2220

gacatcatct acaaccctct ggttctggtc aacgagaacg aggagcagag gtaa         2274
```

<210> SEQ ID NO 82
<211> LENGTH: 1578
<212> TYPE: DNA
<213> ORGANISM: Artificial sequence
<220> FEATURE:
<223> OTHER INFORMATION: KAH_4 CpO for Yarrowia lipolitica

<400> SEQUENCE: 82

```
atggagtctc tggttgtcca caccgtcaac gccatctggt gcattgtcat tgtcggtatc     60

ttctccgtcg gctaccacgt ctacggccga gctgttgtcg agcagtggcg aatgcgacga    120
```

-continued

```
tctctcaagc tccagggtgt caagggtcct cctccctcca tcttcaacgg taacgtttcc    180

gagatgcagc gaatccagtc cgaggccaag cactgctccg gtgacaacat catctcccac    240

gactactctt cttctctgtt cccccacttt gaccactggc gaaagcagta cggccgaatc    300

tacacctact ccactggcct caagcagcac ctctacatca accaccccga gatggtcaag    360

gagctctccc agaccaacac cctcaacctc ggccgaatca cccacatcac caagcgactc    420

aaccccattc tcggtaacgg tatcatcacc tccaacggcc cccactgggc ccaccagcga    480

cgaatcattg cctacgagtt cacccacgac aagatcaagg gtatggtcgg tctgatggtc    540

gagtccgcca tgcccatgct caacaagtgg gaggagatgg tcaagcgagg tggtgagatg    600

ggctgtgaca tccgagtcga cgaggacctc aaggatgtct ccgctgacgt cattgccaag    660

gcctgtttcg gctcttcctt ctccaagggc aaggccatct tctccatgat ccgagatctg    720

ctcaccgcca tcaccaagcg atccgtcctc ttccgattca acggtttcac cgacatggtt    780

ttcggctcca agaagcacgg tgacgttgac attgacgctc tcgagatgga gctcgagtcc    840

tccatctggg agactgtcaa ggagcgagag attgagtgca aggacaccca caagaaggac    900

ctcatgcagc tcattctcga gggtgccatg cgatcttgtg acggtaacct gtgggacaag    960

tctgcttacc gacgattcgt tgtcgacaac tgcaagtcca tctactttgc cggccacgac   1020

tccaccgccg tttccgtttc ttggtgcctc atgctgctcg ctctcaaccc ctcttggcag   1080

gtcaagatcc gagatgagat tctgtcctcc tgcaagaacg gtatccccga cgccgagtcc   1140

atccccaacc tcaagaccgt caccatggtc atccaggaga ctatgcgact ctaccctccc   1200

gctcccattg tcggccgaga ggcctccaag gacattcgac tcggtgatct ggttgtcccc   1260

aagggtgtct gtatctggac cctcatcccc gctctgcacc gagatcccga gatctggggt   1320

cccgacgcca acgacttcaa gcccgagcga ttctccgagg gtatctccaa ggcctgcaag   1380

tacccccagt cctacatccc ctttggcctc ggcccccgaa cctgtgtcgg caagaacttt   1440

ggtatgatgg aggtcaaggt cctcgtttct ctgattgtct ccaagttctc cttcactctg   1500

tctcccacct accagcactc tccctcccac aagctgctcg tcgagcccca gcacggtgtt   1560

gtcatccgag ttgtataa                                                 1578


<210> SEQ ID NO 83
<211> LENGTH: 1578
<212> TYPE: DNA
<213> ORGANISM: Artificial sequence
<220> FEATURE:
<223> OTHER INFORMATION: KO_Gib CpO for Yarrowia lipolitica

<400> SEQUENCE: 83

atgtccaagt ccaactccat gaactccacc tcccacgaga ctctcttcca gcagctcgtt     60

ctcggcctcg accgaatgcc cctcatggac gtccactggc tcatctacgt tgcctttggt    120

gcctggctct gctcctacgt catccacgtt ctgtcctctt cctccactgt caaggtcccc    180

gtcgtcggtt accgatccgt tttcgagccc acctggctcc tccgactgcg attcgtctgg    240

gagggtggtt ccatcattgg ccagggctac aacaagttca aggactccat cttccaggtc    300

cgaaagctcg gtaccgacat tgtcatcatc cctcccaact acattgacga ggtccgaaag    360

ctctcccagg acaagacccg atccgtcgag cccttcatca acgactttgc cggccagtac    420

acccgaggta tggtctttct gcagtccgat ctccagaacc gagtcatcca gcagcgactc    480

acccccaagc ttgtctctct caccaaggtc atgaaggaag agctcgacta cgctctgacc    540
```

-continued

```
aaggagatgc ccgacatgaa gaacgacgag tgggttgagg tcgacatctc ttccatcatg    600

gtccgactca tctctcgaat ctccgcccga gttttcctcg gccccgagca ctgccgaaac    660

caggagtggc tcaccaccac cgccgagtac tccgagtctc tcttcatcac cggcttcatc    720

ctccgagttg tcccccacat tctccgaccc ttcattgctc ctctgctgcc ctcttaccga    780

accctgctgc gaaacgtttc ttccggccga cgagtcattg gtgatatcat ccgatcccag    840

cagggtgacg gtaacgagga catcctctct tggatgcgag atgctgccac tggtgaggag    900

aagcagatcg acaacattgc ccagcgaatg ctcattctgt ctctcgcctc catccacacc    960

accgccatga ccatgaccca cgccatgtac gatctgtgtg cctgccccga gtacattgag   1020

cccctccgag atgaggtcaa gtccgtcgtt ggtgcttctg gctgggacaa gaccgctctc   1080

aaccgattcc acaagctcga ctctttcctc aaggagtccc agcgattcaa ccccgttttc   1140

ctgctcacct tcaaccgaat ctaccaccag tccatgaccc tctccgatgg taccaacatc   1200

ccctccggta cccgaattgc tgtcccctct cacgccatgc tccaggactc cgcccacgtc   1260

cccggtccca ctcctcccac tgagttcgac ggtttccgat actccaagat ccgatccgac   1320

tccaactacg cccagaagta cctcttctcc atgaccgact cttccaacat ggcctttggc   1380

tacggtaagt acgcctgccc cggccgattc tacgcctcca acgagatgaa gctgactctg   1440

gccattctgc tcctccagtt tgagttcaag ctccccgacg gtaagggccg accccgaaac   1500

atcaccatcg actccgacat gatccccgac ccccgagctc gactctgtgt ccgaaagcga   1560

tctctgcgtg acgagtaa                                                 1578
```

<210> SEQ ID NO 84
<211> LENGTH: 2133
<212> TYPE: DNA
<213> ORGANISM: Artificial sequence
<220> FEATURE:
<223> OTHER INFORMATION: CPR_3 CpO for Yarrowia lipolitica

<400> SEQUENCE: 84

```
atgtcctcct cttcttcttc ttccacctcc atgattgatc tcatggctgc catcatcaag     60

ggtgagcccg tcattgtctc cgaccccgcc aacgcctccg cctacgagtc cgttgctgcc    120

gagctgtcct ccatgctcat cgagaaccga cagtttgcca tgatcgtcac cacctccatt    180

gctgttctca ttggctgcat tgtcatgctc gtctggcgac gatctggctc cggtaactcc    240

aagcgagtcg agcccctcaa gcccctggtc atcaagcccc gagaagagga gatcgacgac    300

ggccgaaaga aggtcaccat cttctttggc acccagaccg gtactgctga gggcttcgcc    360

aaggctctcg gtgaggaagc caaggctcga tacgaaaaga cccgattcaa gattgtcgac    420

ctcgatgatt acgctgccga tgacgacgag tacgaggaga agctcaagaa agaggacgtt    480

gccttcttct tcctcgccac ctacggtgac ggtgagccca ccgacaacgc tgcccgattc    540

tacaagtggt tcaccgaggg taacgaccga ggcgagtggc tcaagaacct caagtacggt    600

gttttcggtc tgggcaaccg acagtacgag cacttcaaca aggttgccaa ggttgtcgac    660

gacatcctcg tcgagcaggg tgcccagcga ctcgtccagg tcggcctcgg tgatgatgac    720

cagtgcatcg aggacgactt cactgcctgg cgagaggctc tgtggcccga gctcgacacc    780

attctgcgag aggaaggtga caccgccgtt gccaccccct acaccgccgc cgtcctcgag    840

taccgagtct ccatccacga ctccgaggat gccaagttca acgacatcaa catggccaac    900

ggtaacggct acaccgtctt tgacgcccag cacccctaca aggccaacgt cgccgtcaag    960

cgagagctcc acacccccga gtccgaccga tcttgtatcc acctcgagtt tgacattgct   1020
```

-continued

```
ggttccggtc tgacctacga gactggtgac cacgttggtg tcctctgtga caacctgtcc   1080
gagactgtcg acgaggctct gcgactcctc gacatgtccc ccgacactta cttctctctg   1140
cacgccgaga aagaggacgg tactcccatc tcttcttctc tgccccctcc cttccctccc   1200
tgcaacctgc gaaccgctct gacccgatac gcctgcctcc tctcttctcc caagaagtct   1260
gctctcgttg ctctggccgc ccacgcctcc gaccccaccg aggctgagcg actcaagcac   1320
ctcgcctctc ccgctggcaa ggacgagtac tccaagtggg ttgtcgagtc ccagcgatct   1380
ctgctcgagg tcatggccga gttcccctcc gccaagcccc ctctcggtgt tttcttcgcc   1440
ggtgttgctc cccgactcca gccccgattc tactccatct cctcttcccc caagatcgcc   1500
gagactcgaa tccacgttac ctgtgctctg gtctacgaga agatgcccac cggccgaatc   1560
cacaagggtg tctgctccac ctggatgaag aacgccgttc cctacgagaa gtccgagaac   1620
tgttcctctg ctcccatctt tgtccgacag tccaacttca agctcccctc cgactccaag   1680
gtccccatca tcatgattgg ccccggtacc ggcctcgccc ccttccgagg cttcctgcag   1740
gagcgactcg ccctcgtcga gtccggtgtc gagctcggcc cctccgtcct cttctttggc   1800
tgccgaaacc gacgaatgga cttcatctac gaagaggagc tccagcgatt cgtcgagtcc   1860
ggtgctctcg ccgagctctc cgttgccttc tcccgagagg gtcccaccaa ggagtacgtc   1920
cagcacaaga tgatggacaa ggcctccgac atctggaaca tgatctccca gggcgcctac   1980
ctctacgtct gcggtgacgc caagggtatg gcccgagatg tccaccgatc tctgcacacc   2040
attgcccagg agcagggctc catggactcc accaaggccg agggtttcgt caagaacctc   2100
cagacctccg gccgatacct ccgagatgtc tgg                                2133
```